US008535897B2

(12) United States Patent
Stockwell

(10) Patent No.: US 8,535,897 B2
(45) Date of Patent: Sep. 17, 2013

(54) ASSAYS FOR NON-APOPTOTIC CELL DEATH AND USES THEREOF

(75) Inventor: Brent R. Stockwell, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 587 days.

(21) Appl. No.: 12/308,593

(22) PCT Filed: Jun. 19, 2007

(86) PCT No.: PCT/US2007/014360
§ 371 (c)(1),
(2), (4) Date: Jul. 28, 2010

(87) PCT Pub. No.: WO2007/149476
PCT Pub. Date: Dec. 27, 2007

(65) Prior Publication Data
US 2011/0008803 A1 Jan. 13, 2011

Related U.S. Application Data

(60) Provisional application No. 60/814,864, filed on Jun. 19, 2006, provisional application No. 60/817,665, filed on Jun. 30, 2006, provisional application No. 60/861,560, filed on Nov. 29, 2006.

(51) Int. Cl.
*C12Q 1/00* (2006.01)
*G01N 33/574* (2006.01)

(52) U.S. Cl.
USPC .................... 435/7.23; 435/4; 435/7.1

(58) Field of Classification Search
None
See application file for complete search history.

(56) References Cited

U.S. PATENT DOCUMENTS
2004/0220257 A1   11/2004   Cesura et al.

OTHER PUBLICATIONS

Azoulay-Zohar et al Biochem., 377:347-355, 2004.*
Lemarsters et al Biochemi Biophy Act 1762:181-190, 2005.*
Liu et al Oncogene 25:419-429, Jan. 2006.*
Balnes et al, Nature 434: 658-662, 2005.*
Protocol of Molecule Probe, invitrogen, Jan. 2006.*
Shinohara et al, Eur J Blochem 267: 6067-6073, 2000.*
Shawver, et al. "A. Smart drugs: tyrosine kinase inhibitors in cancer therapy," Cancer Cell. 1: 117-23. (2002).
Capdeville, et al. "Glivec (STI571, imatinib), a rationally developed, targeted anticancer drug," Nat Rev Drug Discov. 1: 493-502. (2002).
Mokbel, et al. "From HER2 to herceptin," Curr Med Res Opin. 17: 51-9. (2001).
Downward "Targeting RAS signalling pathways in cancer therapy," Nat Rev Cancer. 3: 11-22 (2003).
Kaelin "The concept of synthetic lethality in the context of anticancer therapy," Nat Rev Cancer. 5: 689-98 (2005).
Shi, et al. "Enhanced sensitivity of multiple myeloma cells containing PTEN mutations to CCI-779," Cancer Res. 62: 5027-34. (2002).
Druker, et al. "Effects of a selective inhibitor of the Abl tyrosine kinase on the growth of Bcr-Abl positive cells," Nat Med. 2: 561-6. (1996).
Dolma, et al. "Identification of genotype-selective antitumor agents using synthetic lethal chemical screening in engineered human tumor cells," Cancer Cell. 3: 285-96 (2003).
Bailey, et al. "Microarrays of Small Molecules Embedded in Biodegradable Polymers for Use in Mammalian Cell-Based Screens," Proc Natl Acad Sci U S A. 101: 16144-16149 (2004).
Torrance, et al. "Use of isogenic human cancer cells for high-throughput screening and drug discovery," Nat Biotechnol. 19: 940-5. (2001).
Colicelli, "Human RAS superfamily proteins and related GTPases," Sci STKE. 2004: RE13 (2004).
Walker, et al. "Targeting Ras and Rho GTPases as opportunities for cancer therapeutics," Curr Opin Genet Dev. 15: 62-8 (2005).
Schreiber, S. L. "Chemical genetics resulting from a passion for synthetic organic chemistry," Bioorg. Med. Chem. 6: 1127-1152 (1998).
Schreiber, S. L. "Target-oriented and diversity-oriented organic synthesis in drug discovery," Science. 287: 1964-9. (2000).
Schreiber, S. L. "The small-molecule approach to biology: Chemical genetics and diversity-oriented organic synthesis make . . . ," Chem &. Eng. News. 81: 51-61 (2003).
Stockwell, B. R. "Chemical genetics: ligand-based discovery of gene function," Nat Rev Genet. 1: 116-25. (2000).
Stockwell, B. R. "Frontiers in chemical genetics," Trends Biotechnol. 18: 449-55. (2000).
Stockwell, B. R. "Chemical genetic screening approaches to neurobiology," Neuron. 36: 559-62 (2002).
Stockwell, B. R. "Exploring biology with small organic molecules," Nature. 432: 846-54 (2004).
Smukste, et al. "Advances in chemical genetics," Annu Rev Genomics Hum Genet. 6: 261-86 (2005).
Brown, et al. "A mammalian protein targeted by G1-arresting rapamycin-receptor complex," Nature. 369: 756-758 (1994).
Sabatini, et al. "RAFT1: a mammalian protein that binds to FKBP12 in a rapamycin-dependent fashion and is homologous to yeast TORs," Cell. 78: 35-43. (1994).
Khersonsky, et al. "Facilitated forward chemical genetics using a tagged triazine library and zebrafish embryo screening," J Am Chem Soc. 125: 11804-5 (2003).
Williams, et al. "Identification of compounds that bind mitochondrial F1F0 ATPase by screening a triazine library for correction of albinism," Chem Biol. 11: 1251-9 (2004).
Wan, et al. "Synthesis and target identification of hymenialdisine analogs," Chem Biol. 11: 247-59 (2004).
Oda, et al. "Quantitative chemical proteomics for identifying candidate drug targets," Anal Chem. 75: 2159-65 (2003).

(Continued)

*Primary Examiner* — Lei Yao
(74) *Attorney, Agent, or Firm* — Bryan Cave LLP

(57) ABSTRACT

The invention relates to methods for identifying agents, which induce oxidative cell death in a tumor cell. The invention further relates to methods for identifying tumor cells, which are sensitive to agents that induce oxidative cell death. The invention also relates to methods for identifying subjects who are suffering from tumors, which are sensitive to agents that induce oxidative cell death.

12 Claims, 40 Drawing Sheets

(56) References Cited

OTHER PUBLICATIONS

Parsons, et al. "Integration of chemical-genetic and genetic interaction data links bioactive compounds to cellular target pathways," Nat Biotechnol. 22: 62-69 (2003).
Hsiang, et al. "Identification of mammalian DNA topoisomerase I as an intracellular target of the anticancer drug camptothecin," Cancer Res. 48: 1722-6. (1988).
Eng, et al. "Evidence that DNA topoisomerase I is necessary for the cytotoxic effects of camptothecin," Mol Pharmacol. 34: 755-60. (1988).
Madden, et al. "Overexpression of human topoisomerase I in baby hamster kidney cells: hypersensitivity of clonal isolates to camptothecin," Cancer Res. 52: 525-32. (1992).
Andoh, et al. "Characterization of a mammalian mutant with a camptothecin-resistant DNA topoisomerase I," Proc Natl Acad Sci U S A. 84: 5565-9. (1987).
Bjornsti, et al. Expression of human DNA topoisomerase I in yeast cells lacking yeast DNA topoisomerase I: restoration of sensitivity . . ., Cancer Res. 49: 6318-23. (1989).
Champoux, "Structure-based analysis of the effects of camptothecin on the activities of human topoisomerase I," Ann N Y Acad Sci. 922: 56-64 (2000).
Liu, et al. "Mechanism of action of camptothecin," Ann N Y Acad Sci. 922: 1-10. (2000).
D'Arpa, et al. "Involvement of nucleic acid synthesis in cell killing mechanisms of topoisomerase poisons," Cancer Res. 50: 6919-24. (1990).
Hsiang, et al. "Arrest of replication forks by drug-stabilized topoisomerase I-DNA cleavable complexes as a mechanism of cell killing . . . ," Cancer Res. 49: 5077-82 (1989).
Tsao, et al. "Interaction between replication forks and topoisomerase I-DNA cleavable complexes: studies in a cell-free SV40 DNA..," Cancer Res. 53: 5908-14 (1993).
Traganos, et al. "Induction of apoptosis by camptothecin and topotecan," Ann N Y Acad Sci. 803: 101-10. (1996).
Prestwich, et al. "Benzophenone photoprobes for phosphoinositides, peptides and drugs," Photochem Photobiol. 65: 222-34 (1997).
Olszewski, et al. "Tethered benzophenone reagents for the synthesis of photoactivatable ligands," Bioconjug Chem. 6: 395-400 (1995).
Dorman, et al. "Benzophenone photophores in biochemistry," Biochemistry. 33: 5661-73 (1994).
Chen, et al. "Identification of an 11-kDa FKBP12-rapamycin-binding domain within the 289-kDa FKBP12-rapamycin-associated protein..," Proc Natl Acad Sci U.S A. 92: 4947-51 1995.
Stan, et al. Interaction between FKBP12-rapamycin and TOR involves a conserved serine residue. J. Biol. Chem. 269: 32027-32030 (1994).
Harvey, "An Unidentified VirUs Which Causes the Rapid Production of Tumours in Mice," Nature. 204: 1104-5 (1964).
Kirsten, et al. "Morphological responses to a murine erythroblastosis virus," J. Natl. Cancer Inst. 39: 311-335 (1967).
Barbacid, "Ras genes," Annu Rev Biochem. 56: 779-827 (1987).
Bos, "Ras oncogenes in human cancer: a review," Cancer Res. 49: 4682-9 (1989).
Guerra, et al. "Tumor induction by an endogenous K-ras oncogene is highly dependent on cellular context," Cancer Cell. 4: 111-20 (2003).
Jackson, et al. "Analysis of lung tumor initiation and progression using conditional expression of oncogenic K-ras," Genes Dev. 15: 3243-8 (2001).
Johnson, et al. "Somatic activation of the K-ras oncogene causes early onset lung cancer in mice," Nature. 410: 1111-6 (2001).
Meuwissen, et al. "Mouse model for lung tumorigenesis through Cre/lox controlled sporadic activation of the K-Ras oncogene," Oncogene. 20: 6551-8 (2001).
Malumbres, "RAS oncogenes: the first 30 years," Nat Rev Cancer. 3: 459-65 (2003).
Coleman, et al. "RAS and RHO GTPases in G1-phase cell-cycle regulation," Nat Rev Mol Cell Biol. 5: 355-66 (2004).
Hahn, "Immortalization and transformation of human cells," Mol Cells. 13: 351-61. (2002).

Hahn, et al. "Creation of human tumour cells with defined genetic elements," Nature. 400: 464-8. (1999).
Hahn, et al. "Enumeration of the simian virus 40 early region elements necessary for human cell transformation," Mol Cell Biol. 22: 2111-23. (2002).
Hahn, "Modelling the molecular circuitry of cancer," Nat Rev Cancer. 2: 331-41. (2002).
Hahn, et al. "Rules for making human tumor cells," N Engl J Med. 347: 1593-603. (2002).
Lessnick, at al. "The Ewing's sarcoma oncoprotein EWS/FLI induces a p53-dependent growth arrest in primary human fibroblasts," Cancer Cell. 1: 393-401. (2002).
Rostovtseva, et al. "On the Role of VDAC in Apoptosis: Fact and Fiction," J Bioenerg Biomembr. 37: 129-42 (2005).
Rahmani, et al. "Isolation of a novel human voltage-dependent anion channel gene," Eur J Hum Genet. 6: 337-40 (1998).
Graham, et al. "Genetic approaches to analyzing mitochondrial outer membrane permeability," Curr Top Dev Biol. 59: 87-118 (2004).
Anflous, et al. "Altered mitochondrial sensitivity for ADP and maintenance of creatine-stimulated respiration in oxidative striated muscles.," J Biol Chem. 276: 1954-60 (2001).
Sampson, et al. "Immotile sperm and infertility in mice lacking mitochondrial voltage-dependent anion channel type 3," J Biol Chem. 276: 39206-12 (2001).
Forte, et al. "Molecular genetics of the VDAC ion channel: structural model and sequence analysis," J Bioenerg Biomembr. 19: 341-50 (1987).
Shao, et al. "Circular dichroism studies of the mitochondrial channel, VDAC, from *Neurospora crassa*," Biophys J. 71: 778-86 (1996).
Kmita, et al. "Modulation of the voltage-dependent anion-selective channel by cytoplasmic proteins from wild type and the channel depleted." Acta Biochim Pol. 50: 415-24 (2003).
Mannella, "Minireview: on the structure and gating mechanism of the mitochondrial channel, VDAC," J Bioenerg Biomembr. 29: 525-31 (1997).
Thomas, et al. "Mapping of residues forming the voltage sensor of the voltage-dependent anion-selective channel," Proc Natl Acad Sci U S A. 90: 5446-9 (1993).
Stanley, et al. "Peptide-specific antibodies as probes of the topography of the voltage-gated channel in the mitochondrial outer membrane.," J Biol Chem. 270: 16694-700 (1995).
Casadio, et al. "A 3D model of the voltage-dependent anion channel (VDAC)," FEBS Lett. 520: 1-7 (2002).
Chandra, et al. "Bax-dependent regulation of Bak by voltage-dependent anion channel 2," J Biol Chem. 280: 19051-61 (2005).
Baker, et al. "VDAC1 is a transplasma membrane NADH-ferricyanide reductase," J Biol Chem. 279: 4811-9 (2004).
Thinnes, "Evidence for extra-mitochondrial localization of the VDAC/porin channel in eucaryotic cells," J Bioenerg Biomembr. 24: 71-5 (1992).
Dermietzel, et al. Cloning and in situ localization of a brain-derived porin that constitutes a large-conductance anion channel.., Proc Natl Acad Sci U S A. 91: 499-503 1994.
Thinnes, et al. Studies on human porin XXI: gadolinium opens Up cell membrane standing porin channels making way for the osmolytes.., Mol Genet Metab. 69: 240-51 (2000).
Buettner, et al. "Evidence for secretory pathway localization of a voltage-dependent anion channel isoform," Proc Natl Acad Sci U S A. 97: 3201-6 (2000).
Gonzalez-Gronow, et al. "The voltage-dependent anion channel is a receptor for plasminogen kringle 5 on human endothelial cells," J Biol Chem. 278: 27312-8 (2003).
Bahamonde, et al. "Plasma membrane voltage-dependent anion channel mediates antiestrogen-activated maxi Cl- currents in C1300..," J Biol Chem. 278: 33284-9 (2003).
Bahamonde, et al. "Voltage-dependent anion channel localises to the plasma membrane and peripheral but not perinuclear mitochondria," Pflugers Arch. 446: 309-13 (2003).
Fiek, ,et al. "Evidence for identity between the hexokinase-binding protein and the mitochondrial porin in the outer membrane..," Biochim Biophys Acta. 688: 429-40 (1982).
Crompton, "The mitochondrial permeability transition pore and its role in cell death," Biochem J. 341 (Pt 2): 233-49 (1999).

Brdiczka, "Contact sites between mitochondrial envelope membranes. Structure and function in energy- and protein-transfer," Biochim Biophys Acta. 1071: 291-312 (1991).
Krimmer, et al. Biogenesis of porin of the outer mitochondrial membrane involves an import pathway via receptors and the general import..., J Cell Biol. 152: 289-300 (2001).
Linden, et al, "Identification of porin as a binding site for MAP2," Biochem Biophys Res Commun. 218: 833-6 (1996).
Madesh, et al."VDAC-dependent permeabilization of the outer mitochondrial membrane by superoxide induces rapid and massive cytochrome c release," JCell Biol. 155: 1003-15 2001.
Tsujimoto, et al. "VDAC regulation by the Bcl-2 family of proteins," Cell Death Differ. 7: 1174-81 (2000).
Shimizu, et al. "Bcl-2 family proteins regulate the release of apoptogenic cytochrome c by the mitochondrial channel VDAC," Nature. 399: 483-7 (1999).
Averet, et al. "NADH is specifically channeled through the mitochondrial porin channel in *Saccharomyces cerevisiae*," J Bioenerg Biomembr. 34: 499-506 (2002).
Vander Heiden, et al. "Outer mitochondrial membrane permeability can regulate coupled respiration and cell survival," Proc Natl Acad Sci U S A. 97: 4666-71 (2000).
Leist, et al. "Four deaths and a funeral: from caspases to alternative mechanisms," Nat Rev Mol Cell Biol. 2: 1-10 (2001).
Majno, et al. "Apoptosis, oncosis, and necrosis. An overview of cell death," Am J Pathol. 146: 3-15. (1995).
Kerr, et al. "Apoptosis: a basic biological phenomenon with wide-ranging implications in tissue kinetics," Br J Cancer. 26: 239-57 (1972).
Baehrecke, "Autophagic programmed cell death in *Drosophila*," Cell Death Differ. 10: 940-5 (2003).
Syntichaki, et al. "The biochemistry of neuronal necrosis: rogue biology?," Nat Rev Neurosci. 4: 672-84 (2003).
Jagtap, et al. " Poly(ADP-ribose) polymerase and the therapeutic effects of its inhibitors," Nat Rev Drug Discov. 4: 421-40 (2005).
Blankenberg, "Recent advances in the imaging of programmed cell death," Curr Pharm Des. 10: 1457-67 (2004).
Danial, et al. "Cell death: critical control points," Cell. 116: 205-19 (2004).
Sgonc, et al. "Apoptosis detection: an overview," Exp Gerontol. 33: 525-33 (1998).
Walker, et al. "Patterns of cell death," Methods Achiev Exp Pathol. 13: 18-54 (1988).
Boyce, et al. "Caspases: an ancient cellular sword of Damocles," Cell Death Differ. 11: 29-37 (2004).
Zhivotovsky, "Apoptosis, necrosis and between," Cell Cycle. 3: 64-6 (2004).
Ohsumi, Y. Molecular dissection of autophagy: two ubiquitin-like systems. Nat Rev Mol Cell Biol. 2: 211-6. (2001).
Abeliovich, et al. "Chemical genetic analysis of Apg1 reveals a non-kinase role in the induction of autophagy," Mol Biol Cell. 14: 477-90 (2003).
Broker, et al. "Cell death independent of caspases: a review," Clin Cancer Res. 11: 3155-62 (2005).
Chen, et al. "Living T9 glioma cells expressing membrane macrophage colony-stimulating factor produce..," Blood. 100: 1373-80 (2002).
Fombonne, et al. "A novel paraptosis pathway involving LEI/L-DNaseII for EGF-induced cell death in somato-lactotrope pituitary cells," Apoptosis. 367-75 (2006).
Franklin, et al. "Mortality in cultures of the dinoflagellate Amphidinium carterae during culture senescence and darkness," Proc Biol Sci. 271: 2099-107 (2004).
Adus, et al. "Human U251MG glioma cells expressing the membrane form of macrophage colony-stimulating..," Cancer Gene Ther. 10: 411-20 (2003).
Schneider, et al. "Intracellular acidification by inhibition of the Na+/H+-exchanger leads to caspase-independent death..," Cell Death Differ. 11: 760-70 (2004).
Sperandio, et al. "Paraptosis: mediation by MAP kinases and inhibition by AIP-1/Alix," Cell Death Differ. 11: 1066-75 (2004).
Wang, Y. et al. "An alternative form of paraptosis-like cell death, triggered by TAJ/TROY and enhanced by PDCD5 overexpression," J Cell Sci. 117: 1525-32 (2004).
Root, et al. "Biological mechanism profiling using an annotated compound library," Chem Biol. 10: 881-92 (2003).
Blanchard, et al. "Eliminating membrane depolarization caused by the Alzheimer peptide Abeta(1-42, aggr.)," Biochem Biophys Res Commun. 293: 1204-8 (2002).
Lunn, et al. "Indoprofen upregulates the survival motor neuron protein through a cyclooxygenase-independent mechanism," Chemistry & Biology. 11: 1489-1493 (2004).
Stegmaier, et al. "Gene expression-based high-throughput screening(GE-HTS) and application to leukemia differentiation," Nat Genet. 36: 257-63 (2004).
Pollitt, et al. "A rapid cellular FRET assay of polyglutamine aggregation identifies a novel inhibitor," Neuron. 40: 685-94 (2003).
Blanchard, et al. "Efficient reversal of Alzheimer's disease fibril formation and elimination of neurotoxicity by a small molecule," Proc Natl Acad Sci 101: 14326-32 (2004).
Root, et al. "Detecting spatial patterns in biological array experiments," J Biomol Screen. 8: 393-8 (2003).
Root, et al. "Global analysis of large-scale chemical and biological experiments," Curr Opin Drug Discov Devel. 5: 355-60 (2002).
Kelley, et al. PathBLAST: a tool for alignment of protein interaction networks. Nucleic Acids Res. 32: W83-8 (2004).
Kelley, et al. "Conserved pathways within bacteria and yeast as revealed by global protein network alignment," Proc Natl Acad Sci U S A. 100: 11394-9 (2003).
Kelley, et al. "A Flexible Data Analysis Tool for Chemical Genetic Screens," Chemistry & Biology. 11: 1495-1503 (2004).
Moffat, et al. "A lentiviral RNAi library for human and mouse genes applied to an arrayed viral high-content screen," Cell. 124: 1283-98 (2006).
Lunn, et al. "Indoprofen upregulates the survival motor neuron protein through a cyclooxygenase-independent mechanism," Chem Biol. 11: 1489-93 (2004).
Kelley, et al. "A flexible data analysis tool for chemical genetic screens," Chem Biol. 11: 1495-503 (2004).
Smukste, et al. "Using small molecules to overcome drug resistance induced by a viral oncogene," Cancer Cell. 9: 133-46 (2006).
Dorman, et al. "Using photolabile ligands in drug discovery and development," Trends Biotechnol. 18: 64-77 (2000).
Weber, et al. "Comparison of the photochemical behavior of four different photoactivatable probes," J Pept Res. 49: 375-83 (1997).
Pestic-Dragovich, et al. "A myosin I isoform in the nucleus," Science. 290: 337-41 (2000).
Nociari, et al. "A novel one-step, highly sensitive fluorometric assay to evaluate cell-mediated cytotoxicity," J. Immunol. Methods. 13: 157-167 (1998).
Wang, et al. "A new microcellular cytotoxicity test based on calcein AM release," Hum. Immunol. 37: 264-270 (1993).
Testa, et al. "SV40 and cell cycle perturbations in malignant mesothelioma," Semin Cancer Biol. 11: 31-8. (2001).
Bosch, et al. Prevalence of human papillomavirus in cervical cancer: a worldwide perspective. International . . . , J Natl Cancer Inst. 87: 796-802 (1995).
Elenbaas, et al. "Human breast cancer cells generated by oncogenic transformation of primary mammary epithelial cells," Genes Dev. 15: 50-65. (2001).
Perez-Stable, et al. "A. Prostate cancer progression, metastasis, and gene expression in transgenic mice," Cancer Res. 57: 900-6. (1997).
Rich, et al. "A genetically tractable model of human glioma formation," Cancer Res. 61: 3556-60. (2001).
Chan, et al. "Caspase inhibitors promote the survival of avulsed spinal motoneurons in neonatal rats," Neuroreport. 12: 541-545 (2001).
Makin, "Targeting apoptosis in cancer chemotherapy," Expert Opin Ther Targets. 6: 73-84. (2002).
Ho, et al. "Detection of antimycin-binding subunits of complex III by photoaffinity-labeling with an azido derivative of antimycin," J Bioenerg Biomembr. 17: 269-82 (1985).

Von Jagow, et al. "Inhibition of electron transfer from ferrocytochrome b to ubiquinone, cytochrome c1..," Biochim Biophys Acta. 387: 409-24 (1975).

Huang, et al. "Superoxide dismutase as a target for the selective killing of cancer cells," Nature. 407: 390-5 (2000).

Wood, et al. Inhibition of superoxide dismutase by 2-methoxyoestradiol analogues . . . , Anticancer Drug Des. 16: 209-15 (2001).

Gilad, et al. "Melatonin is a scavenger of peroxynitrite," Life Sci. 60: PL169-74 (1997).

Plattner, et al. "Differential contribution of the ERK and JNK mitogen-activated protein kinase cascades..," Oncogene. 18: 1807-17 (1999).

Davies, et al. "Mutations of the BRAF gene in human cancer," Nature. 417: 949-54 (2002).

Patton, et al. "Activation of the ras-mitogen-activated protein kinase pathway and phosphorylation . . . ," Cancer Res. 58: 2253-9 (1998).

Beck, et al. "Mechanisms of resistance to drugs that inhibit DNA topoisomerases," Semin Cancer Biol. 2: 235-44 (1991).

Shimizu, et al. "BH4 domain of antiapoptotic Bcl-2 family members closes voltage-dependent anion channel..," Proc Natl Acad Sci U S A. 97: 3100-5 (2000).

Rahmani, et al. "Hepatitis B virus X protein colocalizes to mitochondria with a human voltage-dependent..," J Virol. 74: 2840-6 (2000).

Koppel, et al. "Bacterial expression and characterization of the mitochondrial outer membrane channel. Effects of n-terminal modifications," J Biol Chem. 273: 13794-800 (1998).

Xu, et al. "Mouse VDAC isoforms expressed in yeast: channel properties and their roles in mitochondrial outer membrane permeability," J Membr Biol. 170: 89-102 (1999).

Navratilova, et al. "Solubilization, stabilization, and purification of chemokine receptors using biosensor technology," Anal Biochem. 339: 271-81 (2005).

Stenlund, et al. "Capture and reconstitution of G protein-coupled receptors on a biosensor surface," Anal Biochem. 316: 243-50 (2003).

Cliff, et.al. "A survey of the year 2003 literature on applications of isothermal titration calorimetry," J Mol Recognit. 17: 513-23 (2004).

Leavitt, et al. "Direct measurement of protein binding energetics by isothermal titration calorimetry," Curr Opin Struct Biol. 11: 560-6 (2001).

Rostovtseva, et al. "VDAC channels mediate and gate the flow of ATP: implications for the regulation of mitochondrial function," Biophys J. 72: 1954-62 (1997).

Montal, "Formation of bimolecular membranes from lipid monolayers and a study of their electrical properties," Proc Natl Acad Sci U S A. 69: 3561-6 (1972).

Stewart, et al. "Lentivirus-delivered stable gene silencing by RNAi in primary cells," Rna. 9: 493-501 (2003).

Lee, et al. "Beta-NADH decreases the permeability of the mitochondrial outer membrane to ADP by a factor of 6," J Biol Chem. 269: 30974-80 (1994).

Zizi, et al. "NADH regulates the gating of VDAC, the mitochondrial outer membrane channel," J Biol Chem. 269: 1614-6 (1994).

Mannella, "Conformational changes in the mitochondrial channel protein, VDAC, and their functional implications," J Struct Biol. 121: 207-18 (1998).

Giepmans, et al. "The fluorescent toolbox for assessing protein location and function. Science," 312: 217-24 (2006).

Mannella, "Structural analysis of mitochondrial pores," Experientia. 46: 137-45 (1990).

Peng, et al. "Large scale rearrangement of protein domains is associated with voltage gating of the VDAC channel," Biophys J. 62: 123-31; discussion 131-5 (1992).

Peng, et al. "Determination of the number of polypeptide subunits in a functional VDAC channel from *Saccharomyces cerevisiae*," J Bioenerg Biomembr. 24: 27-31 (1992).

Johnson, et al. "Mitogen-activated protein kinase pathways mediated by ERK, JNK, and p38 protein kinases," Science. 298: 1911-2 (2002).

Inoue, et al. "Isolation and characterization of mitochondrial DNA-less lines from various mammalian..," Biochem Biophys Res Commun. 239: 257-60 (1997).

Noue, et al. "Isolation of mitochondrial DNA-less mouse cell lines and their application for trapping . . . ," J Biol Chem. 272: 15510-5 (1997).

Chrzanowska-Lightowlers, et al. "A microtiter plate assay for cytochrome c oxidase in permeabilized whole cells," Anal Biochem. 214: 45-9 (1993).

Schriner, et al. "Extension of murine life span by overexpression of catalase targeted to mitochondria," Science. 308: 1909-11 (2005).

Levi, et al. "Mitochondrial ferritin," Int J Biochem Cell Biol. 36: 1887-9 (2004).

He, et al. "Identification of potent water soluble purine-scaffold inhibitors of the heat shock protein 90," J Med Chem. 49: 381-90 (2006).

Fury, et al. "A phase I clinical pharmacologic study of pralatrexate in combination with probenecid in adults..," Cancer Chemother Pharmacol. 57: 671-7 (2006).

Frost, et al. "Simian virus 40 small t antigen cooperates with mitogen-activated kinases to stimulate AP-1 activity," Mol Cell Biol 14, 6244-52 (1994).

Cheng, et al. "VDAC2 inhibits BAK activation and mitochondrial apoptosis," Science 301, 513-7 (2003).

Poyurovsky, et al. "Nucleotide binding by the Mdm2 RING domain facilitates Arf-independent Mdm2 nucleolar localization," Mol Cell 12, 875-87 (2003).

Zhen, Y. et al. "Development of an LC-MALDI method for the analysis of protein complexes," J Am Soc Mass Spectrom 15, 803-22 (2004).

Sage, et al. "Acute mutation of retinoblastoma gene function is sufficient for cell cycle re-entry," Nature 424, 223-8 (2003).

Le Mellay, et al. "Negative regulation of mitochondrial VDAC channels by C-Raf kinase," BMC Cell Biol. 3:14 (2002).

Velde, et al. "BNIP3 and Genetic Control of Necrosis-Like Cell Death through the Mitochondrial..," Molecular and Cellular Biology 20(15):5454-5468 (Aug. 2000).

Shinohara et al. "Characterization of porin isoforms expressed in tumor cells," European Journal of Biochemistry 267(19):6067-6073 (2000).

Gard et al. "Oxidative stress causes ERK phosphorylation and cell death in cultured retinal pigment epithelium..," BMC. Ophthalmology 3(5):1-15 (2003).

Vial et al. "ERK-MAPK signaling coordinately regulates activity of Rac1 and RhoA for tumor cell motility," Cancer Cell vol. 4, 67-79 (2003).

Scorrano et al. "Arachidonic Acid Causes Cell Death through the Mitochondrial Permeability Transition," JBC 276(15):12035-12040 (2001).

Antos et al. "Under Conditions of Insufficient Permeability of VDAC1 External NADH May..," Journal of Bioenergetics and Biomembranes 33(2):119-126 (2001).

Pavlov et al. "A novel, high conductance channel of mitochondria linked to apoptosis..," The Journal of Cell Biology 155(5):725-731 (2001).

Zalk et al. "Oligomeric states of the voltage-dependent anion channel and cytochrome c release from mitochondria," Biochem. J. 386(Pt 1):73-83 (2005).

Stockwell et al. High-throughput screening of small molecules in . . . assays involving post-translational modifications, Chemistry & Biology, (1999) vol. 6, pp. 71-83.

* cited by examiner

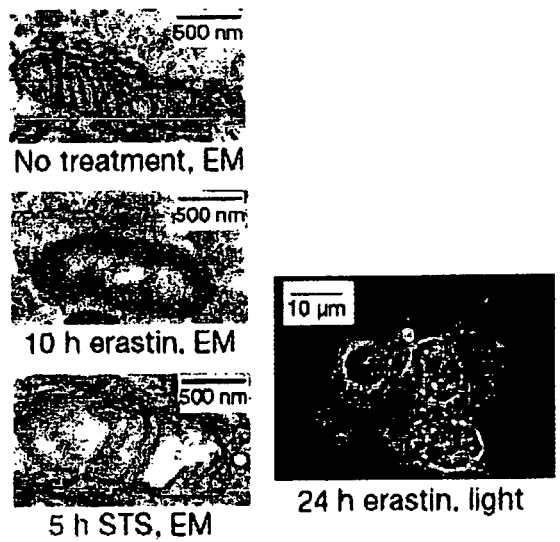
Figure 19 (con't)

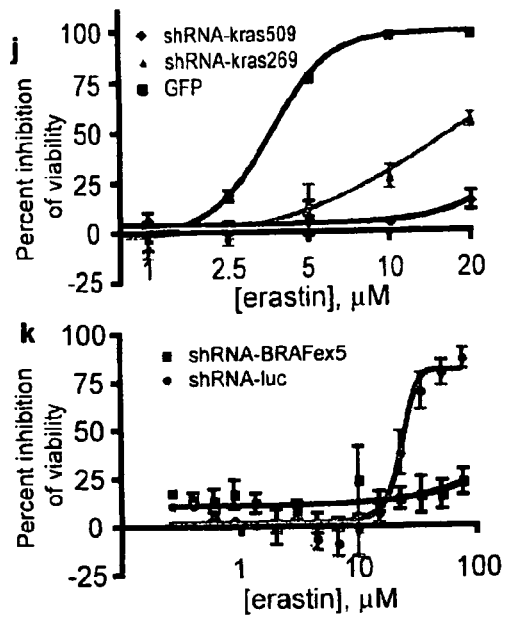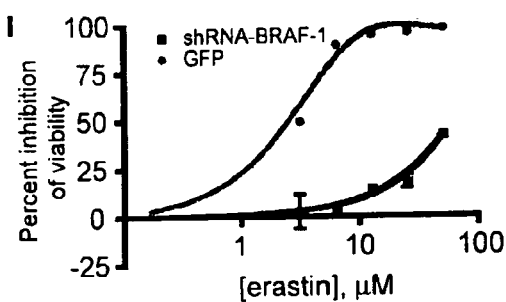
Figure 20 (con't)
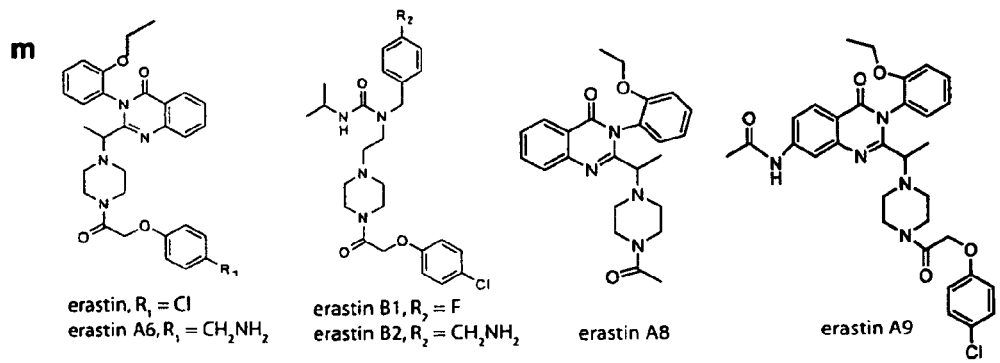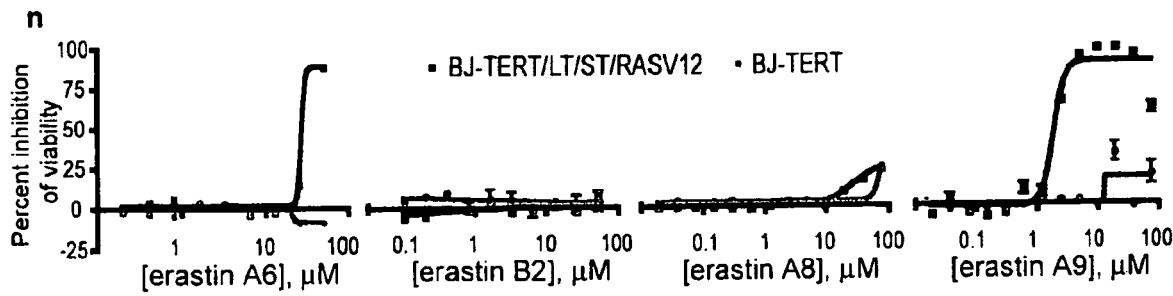

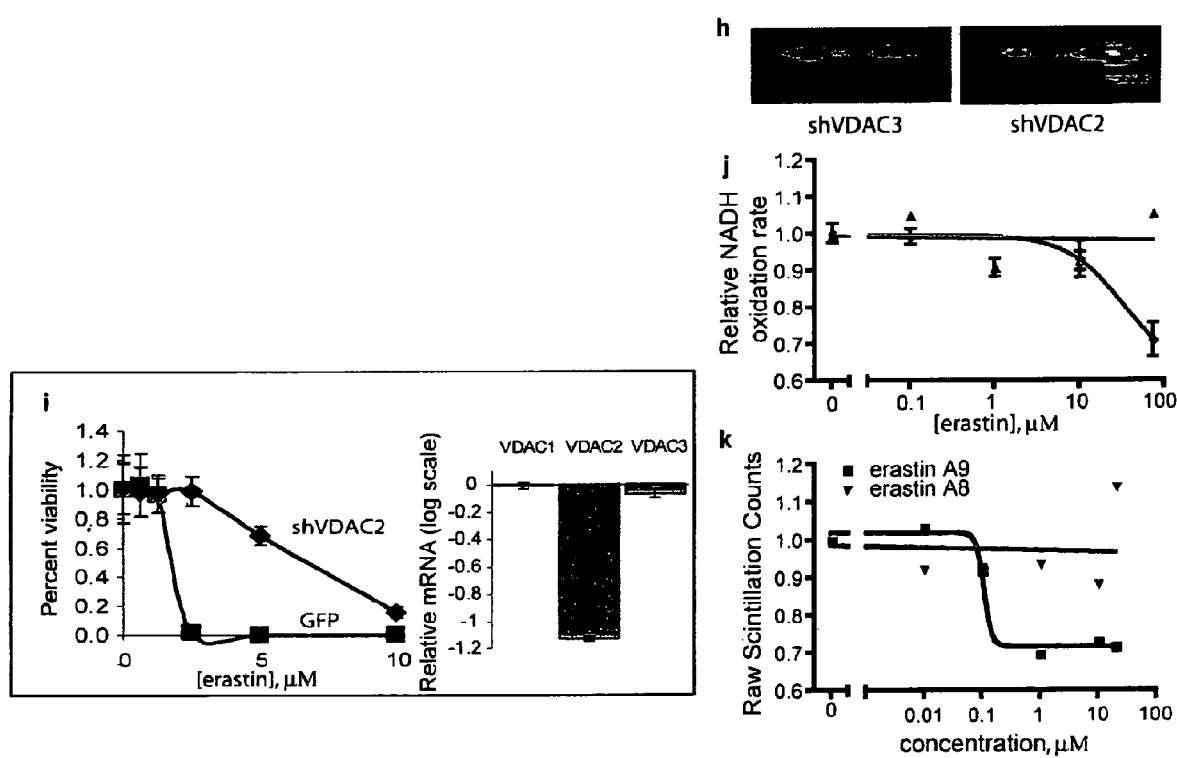
Figure 21 (con't)

| | No Inhibitor | U0126 | MEK Inh I | MEK1/2 Inh | PD98059 | MEK Inh II |
|---|---|---|---|---|---|---|
| IC50 : | | | | | | |
| BJELR | 0.8 | 31.2 | 2.6 | 2.0 | 0.9 | 0.9 |
| HT1080 | 0.5 | 3.4 | 2.5 | 6.0 | 1.0 | 1.3 |
| IC50/IC50 no inh : | | | | | | |
| BJELR | 1.0 | 39.4 | 3.3 | 2.5 | 1.2 | 1.1 |
| HT1080 | 1.0 | 6.4 | 4.8 | 11.3 | 1.9 | 2.4 |
| P-value | | | | | | |
| BJELR | | <0.0001 | <0.0001 | <0.0001 | 0.8262 | 0.6952 |
| HT1080 | | 0.0182 | 0.0014 | 0.0002 | 0.0083 | 0.0104 |

Deferoxamine (DFO)

2-hydroxy-1-naphthylaldehyde
isonicotinoyl hydrazone
(311)

MEK Inh. I

U0126

MEK1/2 Inh.

FIG. 37

PASSIVE

Necrosis

Alberts et al.
Molecular Biology
of the Cell, 4th Ed.

Mitotic
catastrophe

Proc. Natl. Acad. Sci.
USA (2005) 102, 1065-
1070

Others
Dark cell death
oncosis

ACTIVE

Type I
(nuclear, apoptosis)

Type II
(autophagic cell death)
Proc Natl Acad Sci U S A. 2004
Dec 28;101(52):18030-5

Type III
(cytoplasmic, paraptosis)

Cancer Gene Therapy
2003, 10 (5) 411-420

Schweichel and Merker (1973) Teratology 7: 253-266)

ASSAYS FOR NON-APOPTOTIC CELL DEATH AND USES THEREOF

CLAIM TO BENEFIT

This applications claims the benefit of U.S. Provisional Application No. 60/814,864, filed Jun. 19, 2006, U.S. Provisional Application No. 60/817,665, filed Jun. 29, 2006, and U.S. Provisional Application No. 60/861,560, filed Nov. 29, 2006, each of which is incorporated by reference as if recited in full herein.

GOVERNMENT FUNDING

The work described herein was funded, in whole or in part, by National Cancer Institute Grant R01CA097061. The United States government may have certain rights in the invention.

FIELD OF THE INVENTION

The invention is directed to, inter alia, a non-apoptotic mechanism and assays for cell death induced by genotype-selective anti-tumor drugs. The invention is further directed to uses of assays of non-apoptotic cell death to identify agents which are genotype-selective anti-tumor drugs.

BACKGROUND

Molecularly targeted therapeutics represent a promising approach to cancer drug discovery[1]; examples include Gleevec (imatinib mesylate)[2], and Herceptin (trastuzumab)[3]. A limitation of this approach is that some oncogenic proteins are not amenable to inhibition with a small molecule. For example, the RAS oncoproteins are implicated in the genesis of numerous human tumors, but have been difficult to target effectively with small molecules[4]. The first rat sarcoma (RAS) oncogene was discovered as a genetic element from the Harvey and Kirsten rat sarcoma viruses with the ability to immortalize mammalian cells[45-47]. Mutated RAS oncogenes (i.e. HRAS, NRAS and KRAS) are found in 10-20% of all human cancers: KRAS mutations are found in >90% of pancreatic cancers, 50% of colon cancers and 25% of lung adenocarcinomas; NRAS mutations are found in 30% of liver cancers and 15% of melanomas, and HRAS mutations are found in 10% of kidney and bladder cancers[48]. Mice with a KRAS$^{G12V}$ knock-in allele develop bronchiolo-alveolar adenomas[49-52]; mice expressing KRAS$^{G12V}$ and CDK4$^{R24C}$ develop sarcomas and pre-neoplastic lesions of the pancreas[49].

RAS proteins are guanine-nucleotide-binding proteins with GTPase activity and are associated with the plasma membrane. In the GTP-bound form, RAS proteins are mitogenic. Mutation of glycine-12 to other amino acids (including valine, i.e. RAS$^{G12V}$) results in an oncogenic allele with constitutive mitogenic, transforming activity and reduced GTPase activity[53]. Four downstream pathways activated by RAS proteins are (i) the RAF/MEK/ERK pathway, which regulates cell-cycle progression, (ii) the PI3K/PDK/AKT pathway, which regulates cell survival, (iii) the RalGDS pathway, which regulates membrane trafficking and vesicle formation, and (iv) the PLC-gamma/PKC pathway, which regulates Ca$^{++}$ signaling[4, 53, 54]. Small molecules that activate the GTPase activity of RAS proteins might also be developed, although such an approach may be challenging to realize[4]. Alternative approaches, such as inhibiting RAS lipidation and processing, have been pursued[4, 13].

A complementary strategy involves searching broadly for oncogenic-RAS-selective lethal compounds that kill tumor cells only in the presence of oncogenic RAS[5]. This genotype-selective approach can be applied to oncogenes such as those of the RAS gene family, whose gene products cannot be easily inhibited by a small molecule drug[12]. Such oncogene-selective compounds may target novel proteins in oncoprotein-linked signaling networks. Compounds reported to display oncogene-dependent lethality include (1) the rapamycin analog CCI-779 in myeloma cells lacking PTEN[6], (2) Gleevec in BCR-ABL-transformed cells[7], and (3) other less well-characterized compounds[8-11].

Therefore, there remains a need to identify compounds that selectively target and inhibit growth of tumor cells.

SUMMARY OF THE INVENTION

In certain aspects, the invention provides methods for identifying an agent, which induces oxidative cell death in tumor cells, the method comprising: determining VDAC level in a tumor cell, contacting the tumor cell with an agent, and determining whether the tumor cell dies via oxidative cell death, and wherein a tumor cell which dies via oxidative death indicates that the agent induces oxidative cell death. In certain embodiments, oxidative cell death is defined by the presence of oxidative species, and/or decreased protein level of VDAC1, VDAC 2, VDAC 3 or any combination thereof. In other embodiments, oxidative cell death is defined by the presence of oxidative species, and/or decreased protein level of VDAC1, VDAC 2, VDAC 3 or any combination thereof, and the absence of any one of a number of molecular markers which are associated with cell death mechanisms such as apoptosis, necrosis, autophagy, and so forth. Determining of VDAC level can be done by any suitable known method in the art.

In other aspects, the invention provides methods for identifying an agent, which induces oxidative cell death in tumor cells, the method comprising: increasing VDAC level in a cell, contacting the cell with an agent, and determining whether the cell dies via oxidative cell death, wherein a cell which dies via oxidative death indicates that the agent induces oxidative cell death. In certain embodiments, the method increases the expression of VDAC1, VDAC 2, VDAC 3 or any combination thereof. In certain embodiments, VDAC expression can be increased by any suitable method known in the art, including nucleofection with vector carrying nucleic acid encoding VDAC, stable transfection with nucleic acid encoding VDAC, treatment with any suitable agent which increases VDAC expression. In some embodiments, such agents can upregulate VDAC expression by targeting or downregulating inhibitors of VDAC expression. In other embodiments, such agents can target upstream effectors of VDAC function and expression.

In other aspects, the invention provides a method for identifying an agent which induces oxidative cell death in tumor cells, the method comprising: providing a tumor cell, contacting the tumor cell with an agent, and determining whether the tumor cell dies via oxidative cell death, wherein oxidative cell death is determined by (I) detecting: (i) an increased level of oxidative species in the cell; or (ii) a decreased level of VDAC expression in the cell, and (II) identifying one or more of: (i) a lack of caspase 3 cleavage or activation; (ii) a lack of cytochrome C release; (iii) a lack of PARP cleavage or activation; (iv) a lack of Annexin V staining; (v) lack of alterations in chromatin morphology; (vi) a lack of nuclear DNA laddering; (vii) a lack of TUNEL staining of nuclear DNA; (viii) a lack of depletion of ATP levels.

In certain embodiments, the methods of the present invention can be optionally performed in the presence or absence of a second agent selected from the group consisting of: inhibitors of mitochondria-generated oxidative species, iron chelators, and anti-oxidants. In certain embodiments of the methods of the present invention, determining cell viability compares viability in the presence or absence of the second agent, wherein loss of cell viability in the absence of the second agent is indicative of an agent which induces oxidative cell death. An agent which induces cell death only in the absence of inhibitors of mitochondria-generated oxidative species, iron chelators, and anti-oxidants, is indicative of an agent which induces oxidative cell death.

In certain embodiments, the methods of the present invention further comprise determining whether mitochondrial morphology is altered, wherein altered mitochondrial morphology is indicative of an agent which induced an oxidative cell death. In certain embodiments, altered morphology can be detected when mitochondria are enlarged, or fused.

In other aspects, the present invention provides methods for identifying an agent which induces oxidative cell death in tumor cells, the method comprising: providing isolated mitochondria expressing VDAC protein, wherein VDAC protein is VDAC1, VDAC2, or VDAC3, or any isoform thereof, or any combination thereof; contacting the cellular fraction with an agent; and determining whether the agent alters permeability of the outer mitochondrial membrane, wherein an increase in the permeability of the outer mitochondrial membrane is indicative of an agent which induces a non-apoptotic oxidative cell death. In certain embodiments, the isolated mitochondria are in a cellular fraction comprising mitochondria. In other embodiments, the isolated mitochondria are purified mitochondria in a lipid bi-layer. In certain embodiments, determining whether the agent alters permeability of the outer mitochondrial membrane is done by measuring the levels NADH transport. In other embodiments, whether the agent alters permeability of the outer mitochondrial membrane is done by measuring the levels ATP transport.

In other aspects, the invention provides methods for identifying an agent which induces oxidative cell death in tumor cells, the method comprising: providing a tumor cell expressing a fluorescently labeled VDAC protein, wherein the VDAC protein is VDAC1, VDAC2, or VDAC3, or any isoform thereof, or any combination thereof; contacting the tumor cell with an agent; determining cell viability, and measuring the fluorescent signal due to the fluorescently labeled VDAC protein, wherein a decrease in cell viability and a decrease in fluorescence due to the fluorescently labeled VDAC protein is indicative of an agent which induces an oxidative cell death.

In other aspects, the invention provides methods for identifying an agent which induces oxidative cell death in tumor cells, the method comprising: providing a tumor cell expressing a fluorescently labeled VDAC protein comprising two different fluorescent labels, wherein the labeled VDAC protein exhibits fluorescent emission at a first and second wavelength when the channel is open, or a first, second and third (FRET) wavelength when the channel is closed; contacting the tumor cell with an agent; determining cell viability, and measuring the fluorescent signal due to the fluorescently labeled VDAC protein, wherein a decrease in cell viability and a decrease in fluorescence due to FRET in the labeled VDAC protein is indicative of an agent which induces an oxidative cell death. In certain embodiments, the fluorescently labeled VDAC protein is VDAC1, VDAC 2, or VDAC3, or any isoform thereof, or any combination thereof.

In certain aspects, the present invention provides methods for determining susceptibility of a tumor cell to an agent which induces an oxidative cell death, the method comprising: providing a tumor cell and a syngeneic non-tumor cell, and measuring a level of VDAC in the tumor cell and the non-tumor cell, wherein an increase in the level of VDAC in the tumor cell compared to the VDAC level in the non-tumor cell is indicative of a tumor cell, which is susceptible to an agent that induces oxidative cell death. In certain embodiments, VDAC protein level is measured by any suitable method known in the art. In another embodiment, VDAC mRNA level is measured by any suitable method known in the art. In certain embodiments, VDAC protein is VDAC1, VDAC2 or VDAC3, or any isoform, or any combination thereof.

In another aspect, the present invention provides methods for determining susceptibility of a tumor cell to an agent, which induces non-apoptotic oxidative cell death, the method comprising: providing a tumor cell and a syngeneic non-tumor cell, and determining the phosphorylation level of ERK1/2, wherein the presence of a phosphorylated form of ERK1/2 and/or the presence of an increased level of phosphorylated form of ERK1/2 is indicative of a tumor cell which is susceptible to an agent that induces non-apoptotic cell death. In certain embodiments, the tumor cell and the syngeneic cell are derived from a subject suffering from a tumor.

In other aspects, the invention provides methods for identifying novel RAS-selective lethal compounds. The invention provides compounds with increased lethality in oncogenic-RAS-expressing tumor cells. In certain embodiments the compound is erastin. In certain aspects the invention provides methods for identifying cellular proteins which interact with erastin. In certain embodiments, a cellular target protein which interacts with erastin is a VDAC protein, for example, but not limited to, VDAC1, 2, or 3. In other aspects, the invention provides a method for selectively eliminating tumor cells with activated RAS-RAF-MEK-MAPK, for example, signaling by administering genotype-specific anti-tumor compounds, such as but not limited to, erastin. In other aspects, the invention provides that erastin is lethal to tumor cells by a mechanism of non-apoptotic, oxidative cell death. In certain embodiments, the oxidative cell death can be determined by measuring the level of oxidative species.

In certain aspects, the invention is directed to small-molecule-induced, RAS-RAF-MEK-dependent oxidative cell death involving voltage dependent anion channels. Small molecules with oncogene-selective lethality reveal novel functions of oncoproteins and enable creation of tumor selective drugs (Kaelin, W. G. The concept of synthetic lethality in the context of anticancer therapy. *Nat Rev Cancer.* 5: 689-98 (2005). The invention describes the mechanism of action of a novel RAS-RAF-MEK-pathway selective anti-tumor agent. The agent, herein referred to as erastin was discovered in a screen for small molecules that are preferentially lethal to oncogenic-RAS-expressing tumor cells. In certain embodiments, the invention provides that erastin exhibits greater lethality in tumor cells harboring oncogenic mutations in HRAS, KRAS or BRAF. In non-limiting examples, affinity purification and mass spectrometry were used to identify cellular components, including but not limited to proteins, that interact with erastin. In certain aspects, the invention provides that erastin acts through mitochondrial voltage-dependent anion channels (VDACs). In certain embodiments, erastin causes the appearance of oxidative species in cells with oncogenic RAS or RAF. In certain embodiments, cells with oncogenic RAS or RAF die through an oxidative, non-apoptotic death mechanism.

In certain embodiments, down regulation of VDAC activity or protein levels, a non-limiting example of VDAC down regulation is RNA interference-mediated knockdown of VDAC2 or VDAC3, caused resistance to erastin. In certain embodiments, VDAC2 and 3 isoforms of VDAC are implicated in erastin's mechanism of action. In other embodiments, wherein purified mitochondria expressing VDAC3 were used, erastin increased the permeability of the outer mitochondrial membrane, demonstrating that erastin acts through a gain-of-function mechanism, by opening VDAC2 and VDAC3 channels.

In certain embodiments, a screen of ~24,000 compounds, identified erastin, which induces rapid death in engineered tumor cells (BJ-TERT/LT/ST/RAS$^{V12}$ cells (Hahn, W. C. et al. Creation of human tumour cells with defined genetic elements. Nature. 400: 464-8. (1999) with oncogenic HRAS$^{V12}$, but not in isogenic, non-tumorigenic cells lacking oncogenic RAS (BJ-TERT/LT/ST cells). In certain embodiments, the selective cell death was not dependent on the rate of cell division or idiosyncratic to this cell line. In certain embodiments, erastin-treated cells did not display changes in nuclear morphology. In certain embodiments, imaging by electron microscopy revealed changes in mitochondrial morphology, such as enlargement and fusion of mitochondria. These mitochondrial morphological changes were not observed in response to staurosporine, hydrogen peroxide or rapamycin, compounds that induce cell death through apoptosis, necrosis and autophagy, respectively.

In certain aspects, the invention provides methods to identify the mechanism of erastin's action. Such methods can include, but are not limited to, methods involving a chemical suppressor screen to identify known compounds that prevent erastin-induced cell death. Other methods can include an affinity purification approach to identify direct targets of erastin. A suppressor screen using a library of ~2,000 biologically active compounds (Root, D. E., Flaherty, S. P., Kelley, B. P. & Stockwell, B. R. Biological mechanism profiling using an annotated compound library. Chem. Biol. 10: 881-92 (2003) identified antioxidants, including but not limited to alpha-tocopherol, butylated hydroxytoluene and beta-carotene, as a class of compounds which prevent erastin-induced death.

In certain aspects, the invention provides that oxidizing species are formed and detected in response to erastin treatment. In certain embodiments, oxidizing species are detected using dihydrodichlorofluorescein in BJ-TERT/LT/ST/RAS$^{V12}$ cells, but not in isogenic BJ-TERT cells. In certain embodiments, there is a modestly increased sensitivity to erastin in the presence of the Small T oncoprotein (ST), perhaps because ST moderately activates the RAS-RAF-MEK-MAPK pathway. (Frost, J. A. et al. Simian virus 40 small t antigen cooperates with mitogen-activated kinases to stimulate AP-1 activity. Mol Cell Biol 14, 6244-52 (1994).) In certain embodiments, the BJ-TERT cell line was used as a comparison cell line because it lacks both oncogenic HRAS and ST. In certain embodiments, iron chelators, for example but not limited to desferrioxamine, any one of the compounds presented in FIG. 30, suppress erastin-induced lethality via oxidative cell death. Suppression of erastin-induced lethality by an iron chelator, suggests that iron-based Fenton chemistry is involved in this erastin-induced oxidative death. In certain aspects, the invention provides that tumor cells other than BJ-TERT/LT/ST/RASV12 die through this oxidative mechanism. In certain embodiments, erastin induces cell death in HT1080 fibrosarcoma cells. In certain embodiments, erastin-induced cell death in HT1080 cells is suppressed by anti-oxidants.

In certain aspects, the invention provides that the oxidizing species generated in the presence of erastin does not cause PARP1 cleavage, caspase-3 cleavage or cytochrome c release, all hallmarks of apoptosis, indicating this oxidative death is distinct from the oxidative species that appear during some forms of apoptosis due to loss of mitochondrial membrane potential. Indeed, loss of mitochondrial membrane potential only occurred when the cells had died, after 13 hours of erastin treatment.

In certain aspects, the invention provides that erastin does not induce other hallmarks of apoptosis, which is a stereotypical form of programmed cell death activated by many anti-tumor agents (Dolma, S., Lessnick, S. L., Hahn, W. C. & Stockwell, B. R. Identification of genotype-selective antitumor agents using synthetic lethal chemical screening in engineered human tumor cells. Cancer Cell. 3: 285-96 (2003); Wyllie, A. H. Glucocorticoid-induced thymocyte apoptosis is associated with endogenous endonuclease activation. Nature. 284: 555-6 (1980); Kerr, J. F., Wyllie, A. H. & Currie, A. R. Apoptosis: a basic biological phenomenon with wide-ranging implications in tissue kinetics. Br J Cancer. 26: 239-57 (1972); Martin, S. J. et al. Early redistribution of plasma membrane phosphatidylserine is a general feature of apoptosis regardless of the initiating stimulus: inhibition by overexpression of Bcl-2 and Abl. J Exp Med. 182: 1545-56 (1995); Yuan, J., Shaham, S., Ledoux, S., Ellis, H. M. & Horvitz, H. R. The C. elegans cell death gene ced-3 encodes a protein similar to mammalian interleukin-1 beta-converting enzyme. Cell. 75: 641-52 (1993). Such hallmarks include caspase-3 cleavage and activation, annexin V staining, alterations in chromatin morphology, poly(ADP ribose)polymerase (PARP) cleavage and cytochrome c release from mitochondria (Song, Z. & Steller, H. Death by design: mechanism and control of apoptosis. Trends Cell Biol. 9: M49-52. (1999); Majno, G. & Joris, I. Apoptosis, oncosis, and necrosis. An overview of cell death. Am J Pathol. 146: 3-15. (1995). None of these apoptotic markers were activated by erastin. In addition, there is no DNA ladder formation from erastin treated cells, and there is no suppression of oxidative cell death by pan-caspase inhibitors. Moreover, a classic hallmark of necrotic death, complete depletion of ATP, was not observed in erastin-treated cells. In certain aspects, the invention provides that erastin induces rapid, oxidative, non-apoptotic death in tumor cells with oncogenic HRAS. In other aspects, the invention provides that tumor cells with activating RAS or RAF mutations are sensitized to erastin induced cell death. Erastin induced cell death is not consistent with autophagic cell death or paraptosis. Erastin induced cell death is not suppressed by 3-methyladenine, an inhibitor of autophagic death. EM analysis further confirmed the absence of autophagic vesicles. There is no extensive vacuolation seen as in paraptosis. Erastin induced cell death is non-necrotic. Erastin induced cell death is suppressed by treatment with cycloheximide, which indicates that erastin leads to cell death via an active mechanism. Therefore, erastin induced cell death is an active cell death process, which is different from any of the previously characterized cell death pathways.

The observation that mitochondrial morphology was perturbed upon erastin treatment suggested that erastin-induced oxidative species originate in mitochondria. In certain embodiments, the invention provides that agents which inhibit formation of mitochondria-generated oxidative species suppress erastin-induced cell death. In certain embodiments, antimycin, a mitochondrial complex III inhibitor (Ho, S. H., Das Gupta, U. & Rieske, J. S. Detection of antimycin-binding subunits of complex III by photoaffinity-labeling with an azido derivative of antimycin. J Bioenerg Biomembr. 17: 269-82 (1985); G, V. O. N. J. & Bohrer, C. Inhibition of electron transfer from ferrocytochrome b to ubiquinone, cytochrome c1 and duroquinone by antimycin. Biochim Biophys

*Acta.* 387: 409-24 (1975), and 2-methoxyestradiol, a superoxide dismutase inhibitor (Huang, P., Feng, L., Oldham, E. A., Keating, M. J. & Plunkett, W. Superoxide dismutase as a target for the selective killing of cancer cells. *Nature.* 407: 390-5 (2000); Wood, L. et al. Inhibition of superoxide dismutase by 2-methoxyoestradiol analogues and oestrogen derivatives: structure-activity relationships. *Anticancer Drug Des.* 16: 209-15 (2001), both partially suppress erastin-induced cell death. Both compounds act upstream of mitochondria-generated hydrogen peroxide and hydroxyl radical (potential oxidative species). However, melatonin, a peroxynitrite scavenger (Gilad, E., Cuzzocrea, S., Zingarelli, B., Salzman, A. L. & Szabo, C. Melatonin is a scavenger of peroxynitrite. *Life Sci.* 60: PL169-74 (1997), did not affect erastin-induced cell death, suggesting peroxynitrite is not involved. Therefore, erastin-induced cell death involves oxidative species emanating from mitochondria. Furthermore, gating of mitochondrial outer membrane permeability is a physiologically important process.

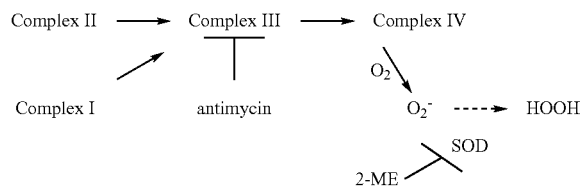

In other aspects, the invention provides that mitochondria, and not peroxisomes, are the source of erastin-induced oxidative species. In certain embodiments, peroxisome proliferators, for example, ciprofibrate, ciglitazone and clofibrate, and xanthine oxidase inhibitors, for example oxypurinol and allopurinol, did not affect erastin-induced cell death. In other embodiments, lipoxygenase inhibitors, prostaglandins, arachidonate esters and acids, and thromboxane receptor antagonists had no effect on erastin-induced cell death, suggesting lipoxygenases and arachidonic acid pathways are not involved. In addition, verapamil, which is a multidrug resistance (MDR) pump inhibitor had no effect on erastin sensitivity, suggesting MDR activity is not involved in the differential sensitivity of cells to erastin. Thus, erastin induces mitochondrial dysfunction in oncogenic RAS-expressing cells, wherein this mitochondrial dysfunction does not result in apoptosis or energy failure.

Erastin was discovered, e.g., in a screen for oncogenic-HRAS-selective lethal compounds. KRAS is more frequently mutated in human cancers than HRAS. Thus, whether erastin is selectively lethal to tumor cells harboring oncogenic KRAS was tested. Calu-1 is a lung carcinoma cell line (Calu-1) with an activating mutation in KRAS. In certain embodiments, Calu-1 cells were sensitive to erastin ($IC_{50}$=5 μM). Two different lentiviral constructs were used to reduce expression of mutant KRAS. Reduction of mutant KRAS levels leads to significant resistance to erastin.

In certain aspects, the invention provides that erastin is lethal to tumor cells with activating mutations in proteins downstream of RAS proteins. Dose-response of 30 tumor cell lines to erastin was measured, and at least 50% inhibition of cell viability in 19 of the 30 tumor cell lines was formed. Numerous sarcoma-derived tumor cell lines were sensitive to erastin, consistent with the fact that erastin was discovered in an engineered tumor cell line created from human fibroblasts. Non-limiting examples include, HT1080 fibrosarcoma cells. HT1080 fibrosarcoma cells, which have a known activating mutation in *NRAS*, (Plattner, R. et al. Differential contribution of the ERK and JNK mitogen-activated protein kinase cascades to Ras transformation of HT1080 fibrosarcoma and DLD-1 colon carcinoma cells. *Oncogene.* 18: 1807-17 (1999), were quite sensitive to erastin. In order to determine whether RAS-activated signaling was modulated in cell lines that respond to erastin, the phosphorylation status of ERK1/2 in 12 sarcoma cell lines with a range of sensitivities to erastin was evaluated. In certain aspects, the invention provides a non-zero correlation, such as for example, a correlation coefficient of 0.41, between ERK1/2 phosphorylation status and erastin sensitivity in these cell lines. This indicates that although ERK1/2 phosphorylation does not directly predict sensitivity to erastin, it may, in some cases, be a proxy for erastin sensitivity.

In certain aspects the invention provides that erastin acts in a manner that is specific to cells with activated RAS-RAF-MAPK pathway signaling. A non-limiting example of a cell line with moderate sensitivity to erastin is A673, which has an activating V600E mutation in BRAF, which is a direct target of RAS proteins (Davies, H. et al. Mutations of the BRAF gene in human cancer. *Nature.* 417: 949-54 (2002). To determine whether the activating mutation in BRAF influences erastin sensitivity, short hairpin RNA-expressing plasmids targeting either BRAF mRNA or, as a control, luciferase (LUC) mRNA were created. Knockdown cell lines containing these constructs were generated, and their sensitivity to erastin was measured. In certain embodiments, the A673 cells containing either of these two different BRAF-targeted shRNAs were resistant to erastin. Knockdown of BRAF was confirmed at the protein level by western blot. In other embodiments, co-expression of a non-targetable V600E mutant BRAF could partially restore sensitivity of these cells to erastin.

In certain aspects, the invention provides that activated RAS-RAF-MEK signaling renders tumor cells sensitive to erastin. In certain embodiments, treatment of tumor cells with different MEK1/2 inhibitors, which block MEK1/2 signaling, lead to loss of erastin sensitivity in tumor cells. In certain embodiments, three different inhibitors caused erastin resistance in both BJ-TERT/LT/ST/RAS$^{V12}$ and HT1080 cells, with activating mutations in HRAS and NRAS, respectively. In certain aspects, the invention provides that erastin selectivity kills cells in which the RAS-RAF-MEK pathway is constitutively activated.

The invention further provides methods to define erastin's mechanism of action. A non-limiting example is a method for affinity-based target identification. In certain embodiments of this method, erastin analogs that could be linked to solid-phase resin for biochemical purification were synthesized. A non-limiting example is an erastin-related compound, erastin B1, with the ability to kill BJ-TERT/LT/ST/RAS$^{V12}$ fibroblasts expressing oncogenic HRAS, but not isogenic BJ-TERT cells lacking oncogenic HRAS and ST ($IC_{50}$=10 μM). Replacement of the p-chloro substituent in erastin, henceforth referred to as erastin A1, with an aminomethyl group resulted in an analog (erastin A3) that retained the ability to kill BJ-TERT/LT/ST/RAS$^{V12}$ cells but not BJ-TERT cells. Replacement of the p-fluoro group in erastin B1 with an aminomethyl group resulted in an analog, referred to as erastin B2, that lacks activity.

Erastin A6, Erastin A3, and erastin B2 were immobilized on solid-phase resins, and proteins that interact with A3 or A6, but not B2 were identified. In certain embodiments, wherein BJ-TERT/LT/ST/RAS$^{V12}$ cell lysates were used, all three isoforms of the human mitochondrial voltage-dependent anion channels (VDAC1, VDAC2 and VDAC3) were identified on the A3 and A6 resins, but only VDAC1 on the B2 resin. In certain embodiments, wherein BJ-TERT cell lysates were used, a small amount of VDAC1 on the A3 and A6 resins was identified, but none of the VDACs were bound on the B2 resin. Thus, it appears that erastin A3 and A6 more efficiently isolate VDAC2 and VDAC3 compared to erastin B2. All three VDACs are identified from the pull-downs performed on BJ-TERT/LT/ST/RAS$^{V12}$ cell lysate, which indicates that VDACs are expressed at a higher level in BJ-TERT/LT/ST/RAS$^{V12}$ cells compared to BJ-TERT cells. Moreover, all three VDACs are identified with higher confidence from the pull-downs performed on BJ-TERT/LT/ST/RAS$^{V12}$ cell lysate with erastin A6 compared to the pulldowns on BJ-TERT cells with erastin A6, suggesting VDACs are more readily purified from BJ-TERT/LT/ST/RAS$^{V12}$ cells compared to BJ-TERT cells.

VDACs, also known as eukaryotic porins, are membrane-spanning channels that facilitate transmembrane transport of ions and metabolites (Graham, B. H. & Craigen, W. J. Genetic approaches to analyzing mitochondrial outer membrane permeability. *Curr Top Dev Biol.* 59: 87-118 (2004); Baker, M. A., Lane, D. J., Ly, J. D., De Pinto, V. & Lawen, A. VDAC1 is a transplasma membrane NADH-ferricyanide reductase *J Biol Chem.* 279: 4811-9 (2004), most notably across the outer mitochondrial membrane (Rostovtseva, T. & Colombini, M. ATP flux is controlled by a voltage-gated channel from the mitochondrial outer membrane. *J Biol Chem.* 271: 28006-8 (1996). There are three human VDAC genes, VDAC1, VDAC2 and VDAC3, of which VDAC1 is the most studied (Graham et al., (2004); Rahmani, Z., Maunoury, C. & Siddiqui, A. Isolation of a novel human voltage-dependent anion channel gene. *Eur J Hum Genet.* 6: 337-40 (1998). The three gene products are ~70% identical and likely have distinct cellular and organismal functions (Graham et al., (2004). Although no atomic-resolution structure of VDAC is available, they have been proposed to adopt a beta barrel fold analogous to the bacterial porins (Casadio, R., Jacoboni, I., Messina, A. & De Pinto, V. A 3D model of the voltage-dependent anion channel (VDAC). *FEBS Lett.* 520:1-7 (2002); Forte, M., Guy, H. R. & Mannella, C. A. Molecular genetics of the VDAC ion channel: structural model and sequence analysis. *J Bioenerg Biomembr.* 19: 341-50 (1987); Shao, L., Kinnally, K. W. & Mannella, C. A. Circular dichroism studies of the mitochondrial channel, VDAC, from *Neurospora crassa. Biophys J.* 71: 778-86 (1996). The finding that erastin pulls down a mitochondrial protein (VDAC) is consistent with the observation that erastin induces a mitochondria-driven oxidative death.

In certain aspects, the invention provides that altered expression of VDACs contributes to erastin sensitivity. To determine whether VDACs are upregulated in response to oncogenic RAS, VDAC abundance was measured, using an antibody that recognizes all three isoforms, in the BJ cell series (primary BJ cells, BJ-TERT cells containing hTERT, BJ-TERT/LT/ST cells containing additionally LT and ST, or BJ-TERT/LT/ST/RAS$^{V12}$ cells containing additionally HRAS$^{G12V}$). In BJ-TERT/LT/ST/RAS$^{V12}$ cells, total VDAC protein is increased relative to these other cell lines.

In other embodiments, after 8 hours of erastin treatment, VDAC3 was no longer detectable, and after 10 hours, VDAC2 also became undetectable. This type of downregulation has also been observed in the case of treatment with camptothecin which targets topoisomerase I. This indicates that erastin acts by a gain-of-function mechanism and that cells with more VDAC protein are more sensitive to erastin. A similar gain-of-function mechanism occurs with doxorubicin and topoisomerase II alpha, and with camptothecin and topoisomerase I (Beck, W. T. & Danks, M. K. Mechanisms of resistance to drugs that inhibit DNA topoisomerases. *Semin Cancer Biol.* 2: 235-44 (1991) suggesting that a cellular response to erastin may be the downregulation of VDAC2/3 after lethal oxidative species have been generated, as occurs with camptothecin and topoisomerase I and DNA damage. The fact that VDAC1 is still present at these later time points suggests that the loss of VDAC2/3 is not simply due to loss of mitochondria.

To test this gain-of-function hypothesis, VDAC protein levels were reduced using a lentiviral shRNA expression system (Moffat et al. 2006). Five shRNA constructs were created targeting each VDAC isoform and their effects on erastin resistance were tested. In certain embodiments, knockdown of VDAC3 caused significant resistance to erastin. In another embodiment, there is a degree of erastin resistance when VDAC2 was knocked down. The isoform specificity of each shRNA reagent was confirmed at the mRNA and protein level. These results are consistent with a gain of function mechanism, such as increasing permeability of the outer mitochondrial membrane. In contrast, overexpression of VDAC3 alone in BJ-TERT cells yielded no increase in sensitivity to erastin, suggesting that other downstream aspects of RAS-RAF-MEK signaling are needed to sensitize cells to erastin, such as increasing rates of glycolysis and respiration. Overall, these results are consistent with a gain of function mechanism involving erastin and VDAC2/3. This effect is specific to erastin, but not other lethal compounds, e.g., VDAC2-deficient embryonic stem cells have been shown to be more sensitive, not less sensitive, to staurosporine and etoposide. (Cheng, E. H., Sheiko, T. V., Fisher, J. K., Craigen, W. J. & Korsmeyer, S. J. VDAC2 inhibits BAK activation and mitochondrial apoptosis. Science 301, 513-7 (2003).)

In certain embodiments, mitochondria can be purified from yeast that had been engineered to express murine or human VDAC3 in place of yeast VDAC. A previous report demonstrated that the rate of NADH uptake through the outer membrane of such mitochondria is dependent on the specific VDAC expressed in yeast, such as for example, murine VDAC3 in these yeast. In certain embodiments, erastin treatment increases the permeability of murine or human VDAC3-expressing mitochondria to NADH, consistent with the proposed gain-of-function mechanism involving channel opening. In other embodiments, erastin treatment increases the permeability of murine or human VDAC3-expressing mitochondria to NADH. Little intrinsic membrane permeability was found with VDAC3, consistent with previous reports that VDAC3 does not gate well in vitro. (Xu, X., Decker, W., Sampson, M. J., Craigen, W. J. & Colombini, M. Mouse VDAC isoforms expressed in yeast: channel properties and their roles in mitochondrial outer membrane permeability. J Membr Biol 170, 89-102 (1999).) An inactive analog of erastin, erastin A8, had no effect on mitochondrial membrane permeability. These results suggest that erastin affects VDAC gating, possibly switching their ion selectivity and allowing cationic species into mitochondria.

Given the interactions between erastin and VDAC using affinity-based target identification and VDAC functional assays, the direct binding of erastin to VDACs was investigated. Using modified versions of previously reported protocols, VDAC2 was isolated from *E. coli* for use in a competition binding experiment using a radioactively labeled analog (erastin A9). (Poyurovsky, M. V. et al. Nucleotide binding by the Mdm2 RING domain facilitates Arf-independent Mdm2 nucleolar localization. Mol Cell 12, 875-87 (2003). Koppel, D. A. et al. Bacterial expression and characterization of the mitochondrial outer membrane channel. Effects of n-terminal modifications. J Biol Chem 273, 13794-800 (1998).) The results demonstrate that the RAS-selective lethal erastin A9 (IC$_{50}$: 1.9 µM, FIG. 20n), unlike inactive erastin analog A8, directly binds to VDAC2 (K$_D$: 112 nM, FIG. 21k), in the process competing off radiolabeled erastin A9.

In certain aspects, the invention provides that erastin interacts with VDAC proteins to induce mitochondrial dysfunction, release of oxidative species and, ultimately, non-apoptotic, oxidative cell death. This process appears to be selective for cells with activated RAS-RAF-MEK signaling. In certain aspects, the invention provides methods to identify oncogene-selective compounds and to use the identified oncogene-selective compounds to illuminate oncogene-related cell death mechanisms.

Unlike bacterial porins, the eukaryotic VDACs are gated by membrane voltage, at least in vitro (Mannella, C. A. Minireview: on the structure and gating mechanism of the mitochondrial channel, VDAC. *J Bioenerg Biomembr.* 29: 525-31 (1997). In the closed state, ions, but not small molecule metabolites, can penetrate through VDAC pores (Mannella, C. A. Minireview: on the structure and gating mechanism of the mitochondrial channel, VDAC. *J Bioenerg Biomembr.* 29: 525-31 (1997). In the open state, both ions and metabolites pass through VDAC channels. The mechanism and frequency of channel gating in vivo is not known, although protein regulators of VDAC gating are reported to exist (Kmita, H., Budzinska, M. & Stobienia, O. Modulation of the voltage-dependent anion-selective channel by cytoplasmic proteins from wild type and the channel depleted cells of *Saccharomyces cerevisiae*. *Acta Biochim Pol.* 50: 415-24 (2003). VDACs have also been reported to interact with BCL proteins and participate in the formation of the mitochondrial permeability transition pore that facilitates release of cytochrome c from mitochondria (Shimizu, S., Narita, M. & Tsujimoto, Y. Bcl-2 family proteins regulate the release of apoptogenic cytochrome c by the mitochondrial channel VDAC. *Nature.* 399: 483-7 (1999); Rostovtseva, T. K., Tan, W. & Colombini, M. On the Role of VDAC in Apoptosis: Fact and Fiction. *J Bioenerg Biomembr.* 37: 129-42 (2005); Chandra, D., Choy, G., Daniel, P. T. & Tang, D. G. Bax-dependent regulation of Bak by voltage-dependent anion channel 2. *J Biol Chem.* 280: 19051-61 (2005). This is a critical event in the intrinsic, mitochondria-driven apoptotic pathway, but does not appear to be involved in erastin's mode of action.

In certain aspects, the invention provides that erastin interacts with VDACs or a VDAC-containing mitochondrial outer membrane complex to induce mitochondrial dysfunction, such as for example, altered mitochondrial morphology, changes in the permeability of the outer mitochondrial membrane, increased respiration, which can be measured by determining oxygen consumption, increased leakage of oxidative species, which can be measured with dihydrodichlorofluorescein or other dyes, release of oxidative species and non-apoptotic cell death. In certain embodiments, oxidative cell death is selective for cells with activated RAS or RAF signaling. Erastin's effect on tumor cells is likely because RAS and RAF proteins upregulate VDACs, and by activating RAF family members, which have been reported to inhibit VDACs (Le Mellay, V., Troppmair, J., Benz, R. & Rapp, U. R. Negative regulation of mitochondrial VDAC channels by C-Raf kinase. *BMC Cell Biol.* 3: 14 (2002). Thus, cells with greater RAS/RAF activity are likely to have an increased pool of latent VDACs and are therefore more susceptible to compounds that disregulated VDAC function. In certain aspects, the invention provides methods to discover oncogene-selective compounds, and the use of such compounds to illuminate novel oncogene-specific cell death mechanisms.

Figure 25:
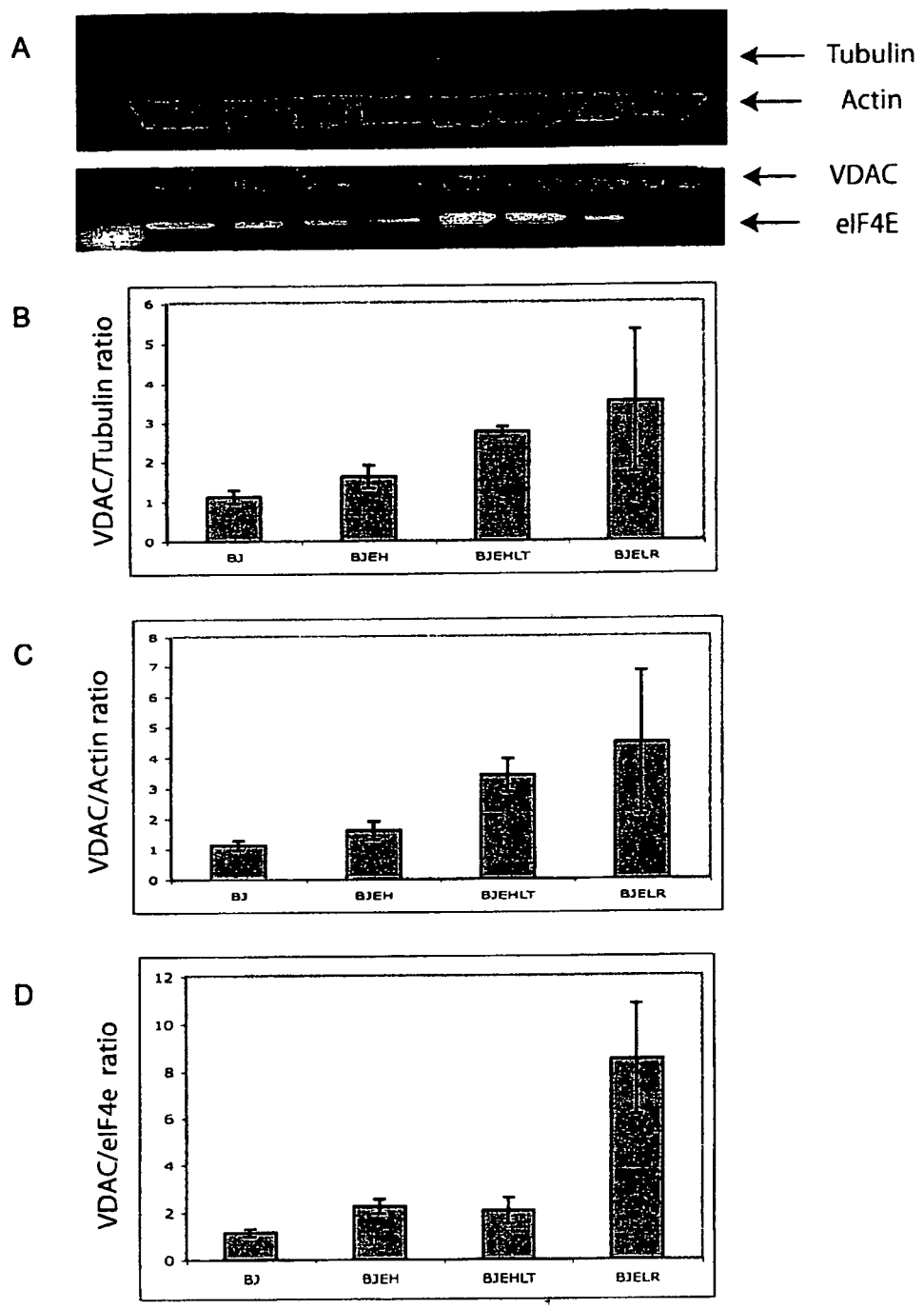

FIG. 25 (panels A-D) shows the levels of VDAC, tubulin, actin and eIF4E were determined in BJ cells, BJEH cells (expressing hTERT), BJEHLT cells (expressing hTERT, and the large and small T oncoproteins from SV40) and BJELR cells (expressing hTERT, and the large and small T oncoproteins from SV40 and oncogenic HRAS). Images were quantified and are plotted as VDAC relative to each control protein. Error bars represent one standard deviation.

Figure 26:
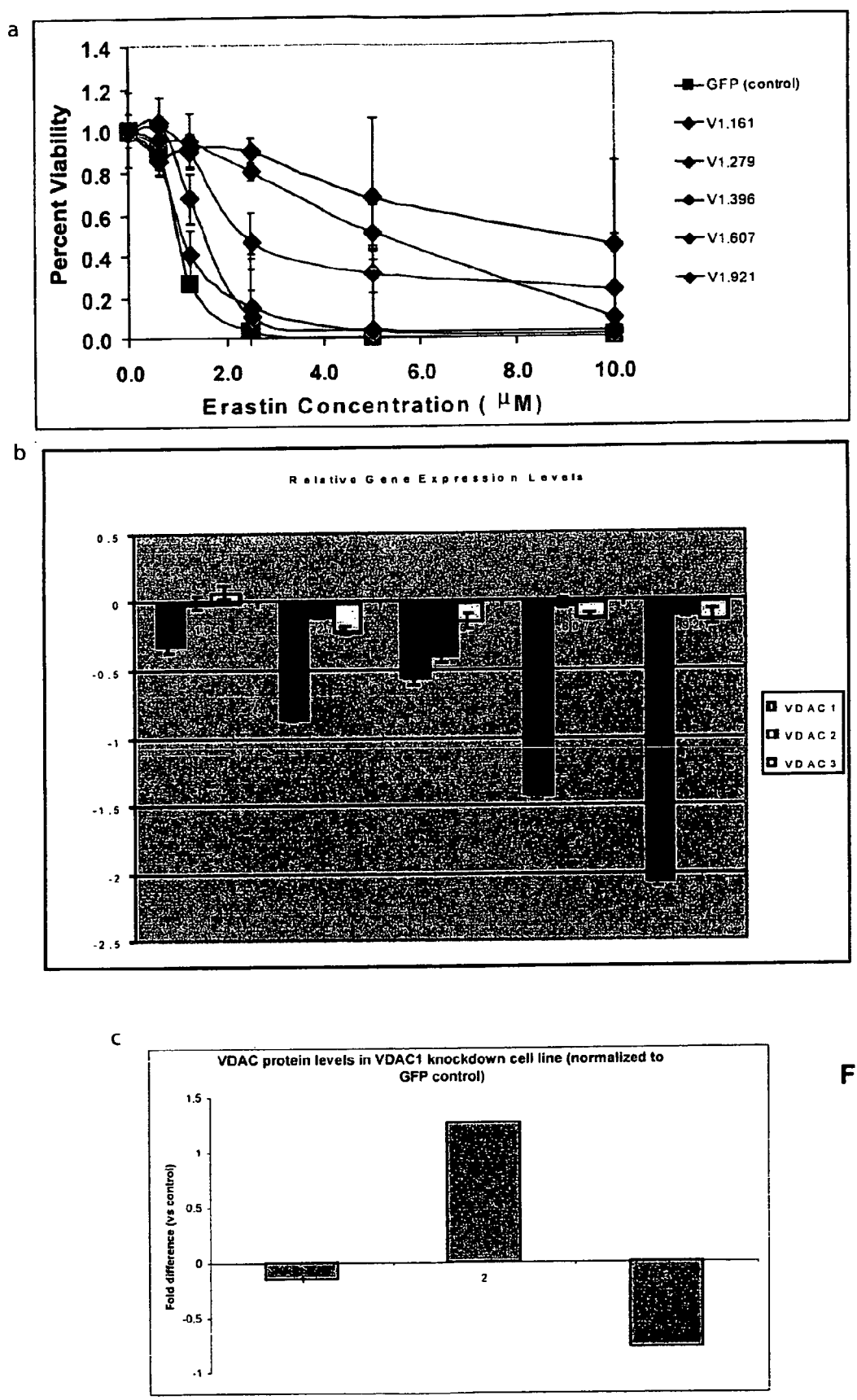

FIG. 26 (panels a-c) shows that transfection with VDAC1 shRNA Protects Viability of Erastin-Treated HT1080 Cells. Briefly, the assay was carried out as follows: Day 1, 293T cells seeded in 10 cm tissue culture dishes ($2 \times 10^6$ cells/dish); Day 2, shRNA-plasmid construct (pLKO.1 vector) introduced to cells using FuGene transfection reagent; Day 3, medium changed; Day 4, supernatant transferred to HT1080 cells in 10 cm tissue culture dishes ($1 \times 10^6$ cells/dish); Day 5, cells transferred to 175 cm$^2$ flasks, medium supplemented with puromycin; Days 6 and 7, medium changed and supplemented with puromycin; Day 8, samples harvested for Western Blot and qRT-PCR, or reseeded in 6-well format ($5 \times 10^5$ cells/well) and treated with erastin dilutions (2-fold, from 10 μM to 625 nM, with no-drug control); Day 9, Vicell analysis performed. Unique VDAC1 shRNAs (V1.161, V1.279, V1.396, V1.607, V1.921), control construct (GFP).

Figure 27:
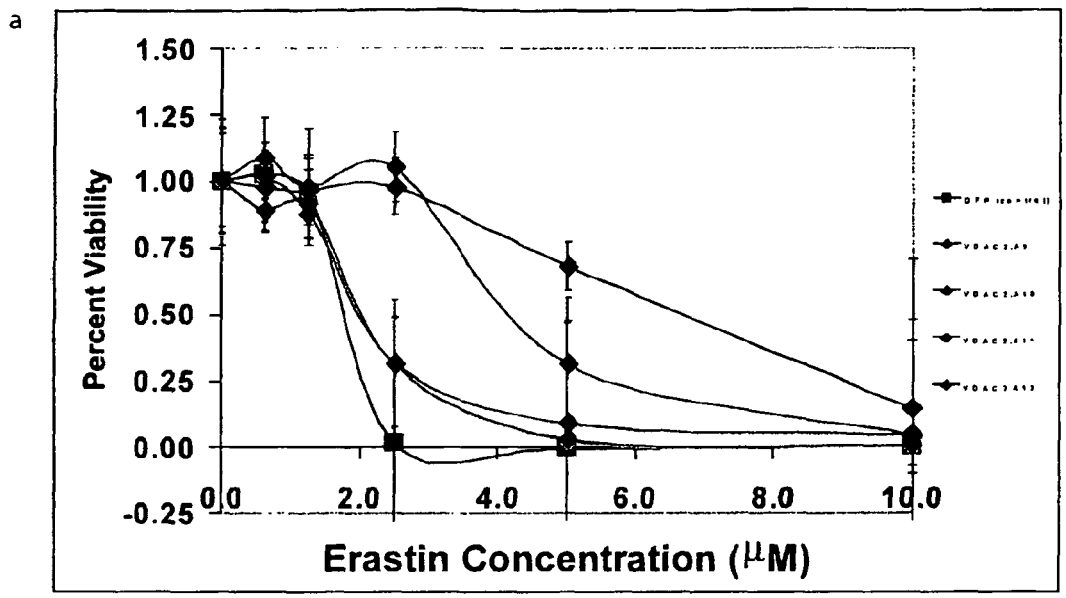
Figure 27:
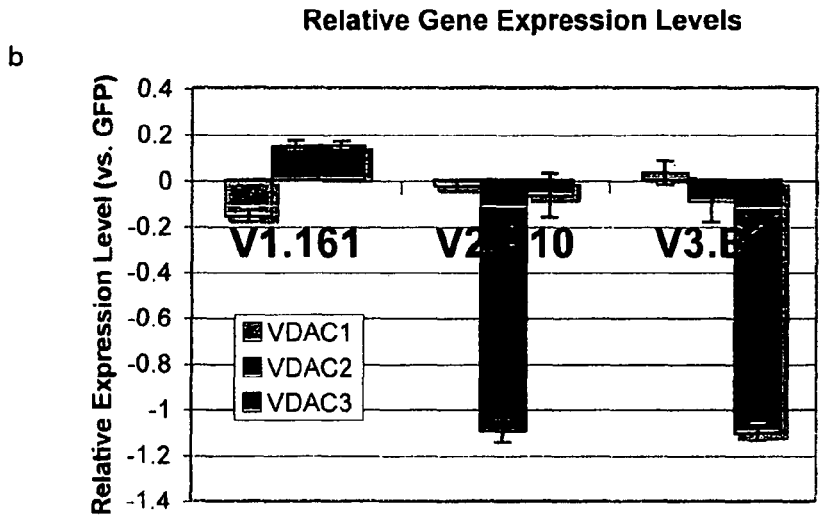
Figure 27:
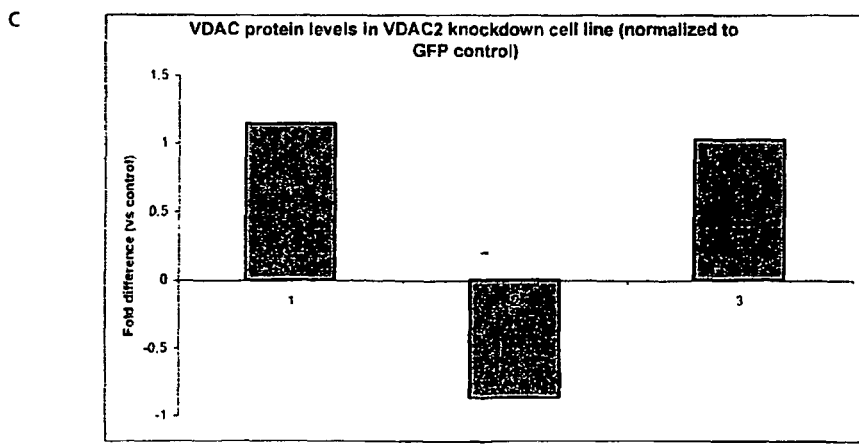

FIG. 27 (panels a-c) shows that transfection with VDAC2 shRNA Protects Viability of Erastin-Treated HT1080 Cells. Briefly, the assay was carried out as follows: Day 1, 293T cells seeded in 10 cm tissue culture dishes ($2 \times 10^6$ cells/dish); Day 2, shRNA-plasmid construct (pLKO.1 vector) introduced to cells using FuGene transfection reagent; Day 3, medium changed; Day 4, supernatant transferred to HT1080 cells in 10 cm tissue culture dishes ($1 \times 10^6$ cells/dish); Day 5, cells transferred to 175 cm$^2$ flasks, medium supplemented with puromycin; Day 6, medium changed and supplemented with puromycin; Day 7, samples harvested for Western Blot and qRT-PCR, or reseeded in E-well format ($5 \times 10^5$ cells/well) and treated with erastin dilutions (2-fold, from 10 μM to 625 nM, with no-drug control). Unique VDAC3 shRNAs (A9, A10, A11, A12), control construct (GFP).

Figure 28:
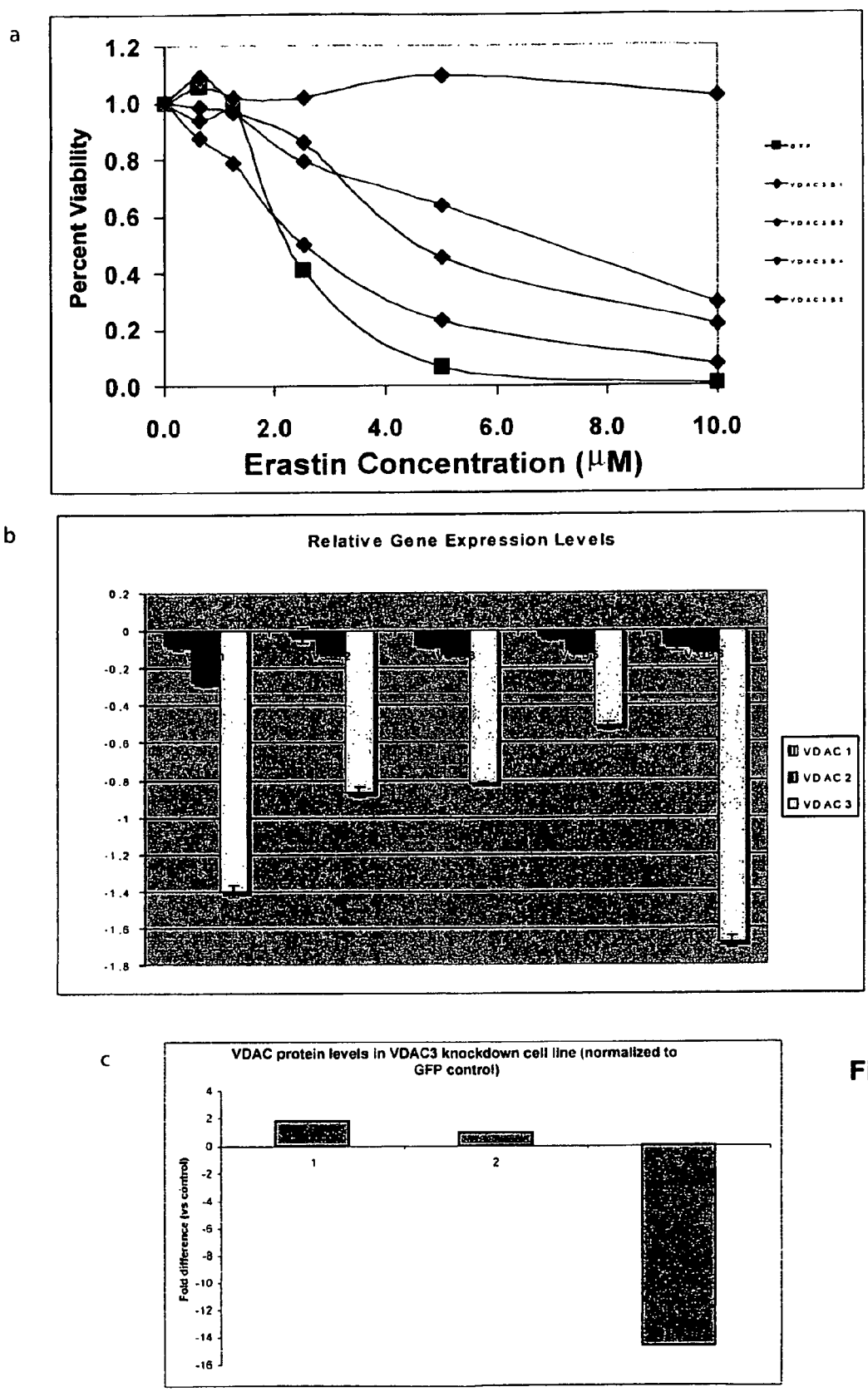

FIG. 28 (panels a-c) shows that transfection with VDAC3 shRNA Protects Viability of Erastin-Treated HT1080 Cells. Briefly, the assay was carried out as follows: Day 1, 293T cells seeded in 10 cm tissue culture dishes ($2 \times 10^6$ cells/dish); Day 2, shRNA-plasmid construct (pLKO.1 vector) introduced to cells using FuGene transfection reagent; Day 3, medium changed; Day 4, supernatant transferred to HT1080 cells in 10 cm tissue culture dishes ($1 \times 10^6$ cells/dish); Day 5, cells transferred to 175 cm$^2$ flasks, medium supplemented with puromycin; Days 6 and 7, medium changed and supplemented with puromycin; Day 8, samples harvested for Western Blot and qRT-PCR, or reseeded in 6-well format ($5 \times 10^5$ cells/well) and treated with erastin dilutions (2-fold, from 10 μM to 625 nM, with no-drug control). Unique VDAC3 shRNAs (B1, B2, B4, B6), control construct (GFP).

Figure 29:
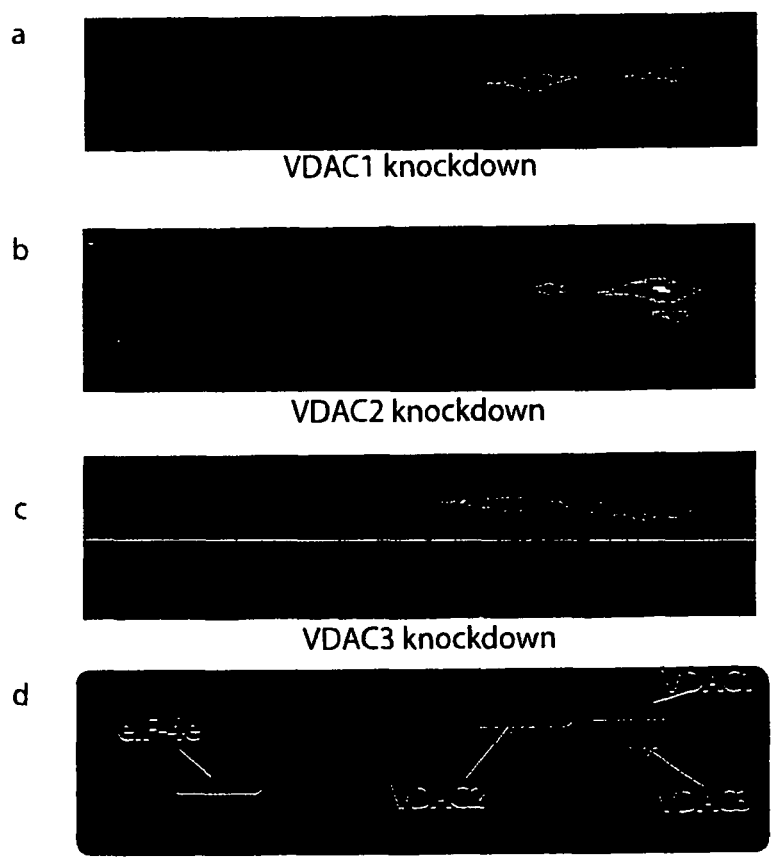

FIG. 29 (panels a-d) shows representative knockdown experiments using pLKO.1 shRNA vector. Briefly, HT0180 cells were infected with a virus expressing a short hairpin RNA (shRNA) to VDAC1, VDAC or VDAC3 and the levels of each VDAC determined by 2D gel and western blotting with a pan-VDAC antibody. The level of eIF4E is shown as a control.

Figure 30:
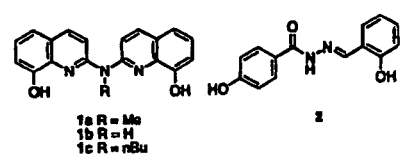
Figure 30:
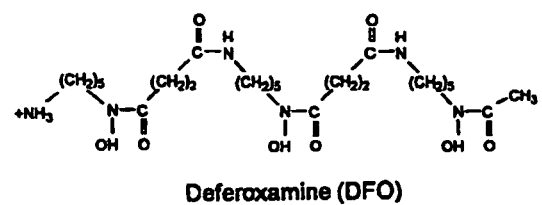
Figure 30:
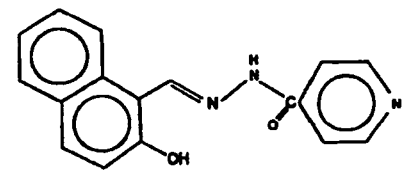

FIG. 30 shows the structures of certain iron chelators used in the present invention.

Figure 31:
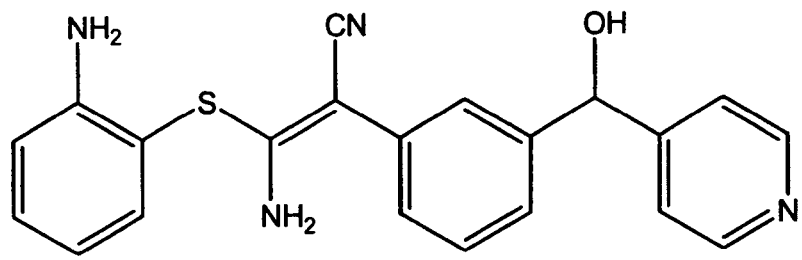
Figure 31:
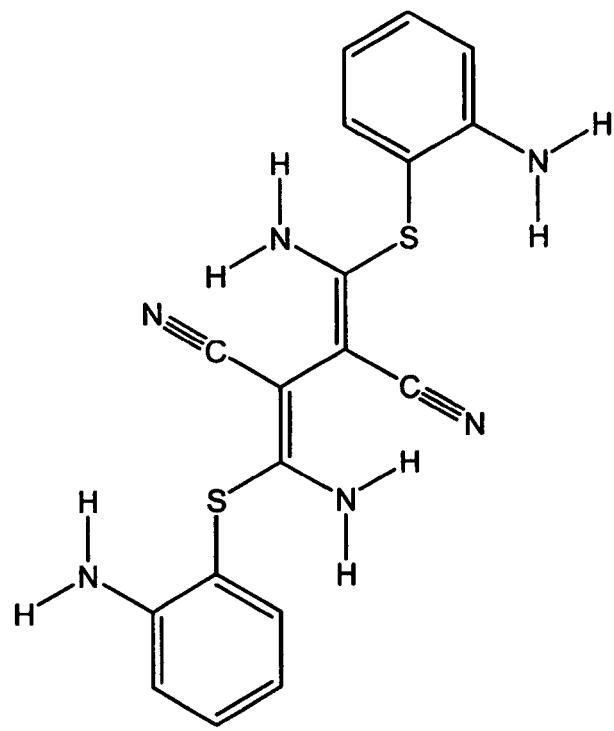
Figure 31:
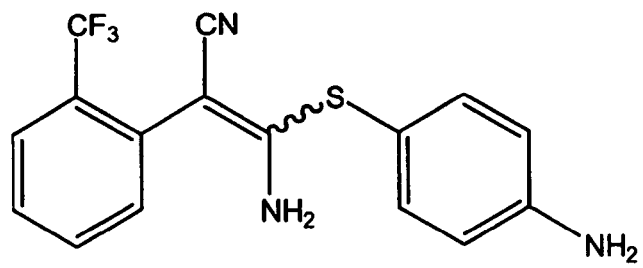

FIG. 31 shows the structures of certain MEK1/2 inhibitors used in the present invention.

Figure 32:
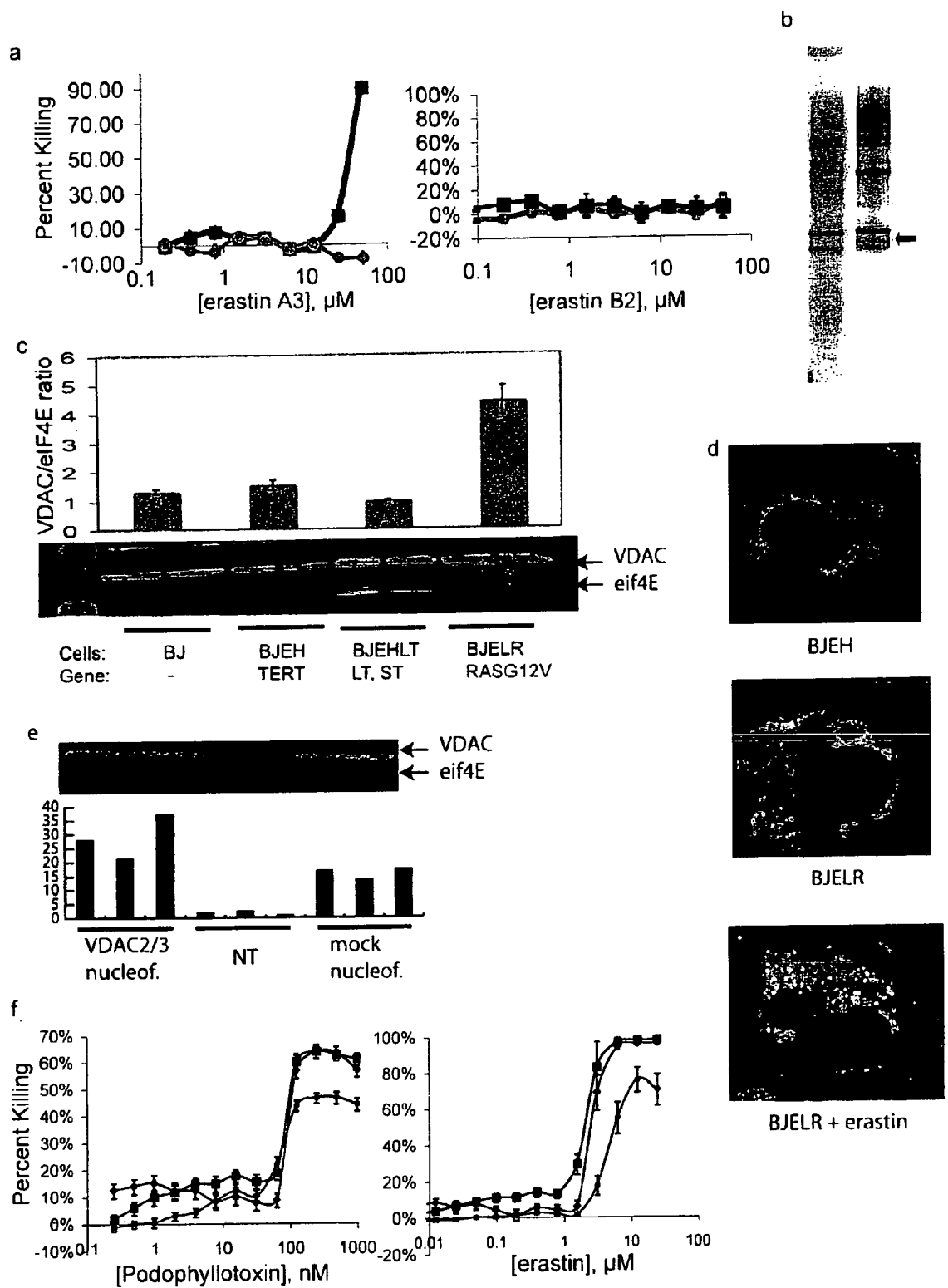

FIG. 32 (panels a-f) shows that erastinA3 and not its analogue, erastinB2, selectively kills tumor cells; immobilized erastin analogues pull down different proteins (b); VDAC protein level is increased in RAS tumors (c); and VDAC protein level in BJELR cells is increased by nucleofection (d). Quantitative western blot showing the ratio of VDACs (top band, green) to eif4E (bottom band, red) (e). Erastin A1 (erastin), but not podophyllotoxin, is more potent (i.e. effective at a lower concentration) in BJELR cells after upregulation of VDACs. Green, untransfected BJELR cells; blue, mock nucleofected BJELR cells; red, VDAC2/3-nucleofected BJELR cells (f).

Figure 33:
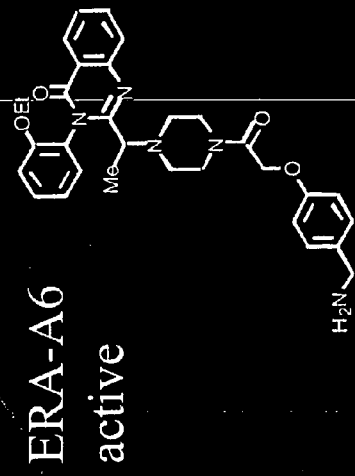
Figure 33:
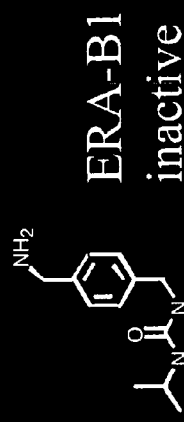
Figure 33:
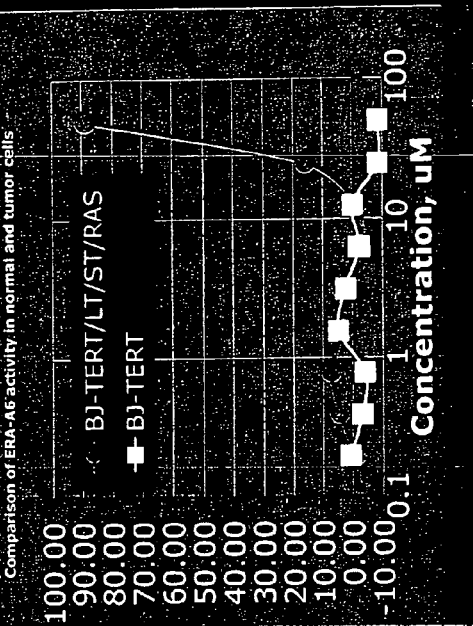
Figure 33:
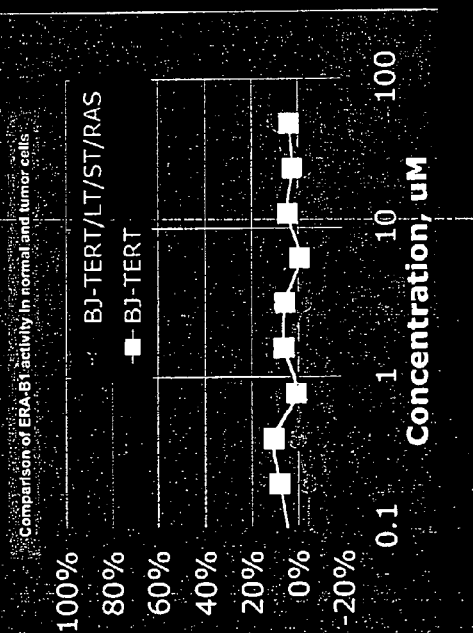

FIG. 33 shows the activity of aminomethyl substituted erastins. ERA-A6, an analog with a p-aminomethyl substituent in place of the p-chloro substituent in erastin, is selectively lethal to RASV12-expressing cells. ERA-B1 is an aminomethyl analog that is inactive and was used as a negative control in pulldown experiments.

Figure 34:
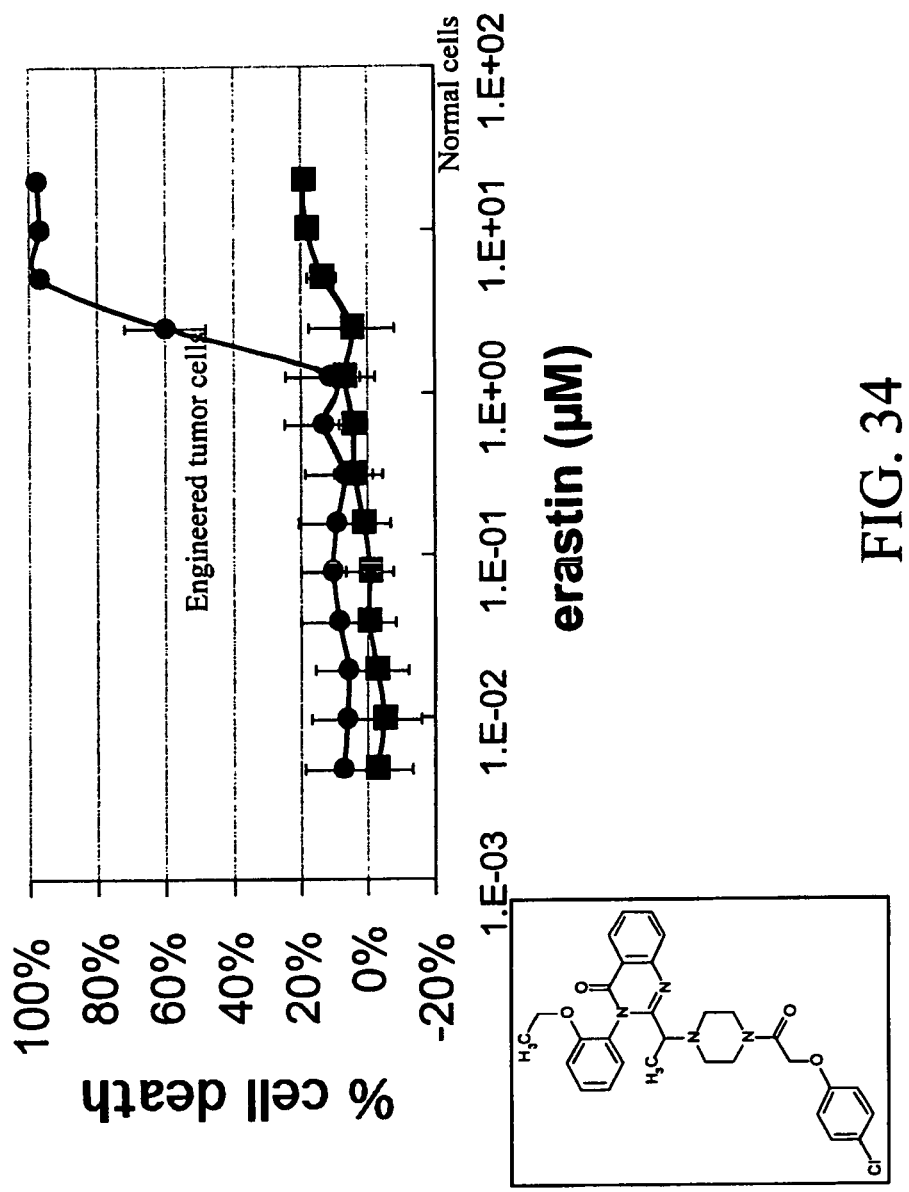

FIG. 34 shows that erastin induces rapid cell death in a RASV12-dependent fashion. Effect of erastin on Alamar Blue viability staining in BJ-TERT (red) and BJ-TERT/LT/ST/RASV12 (blue) cells.

Figure 35:
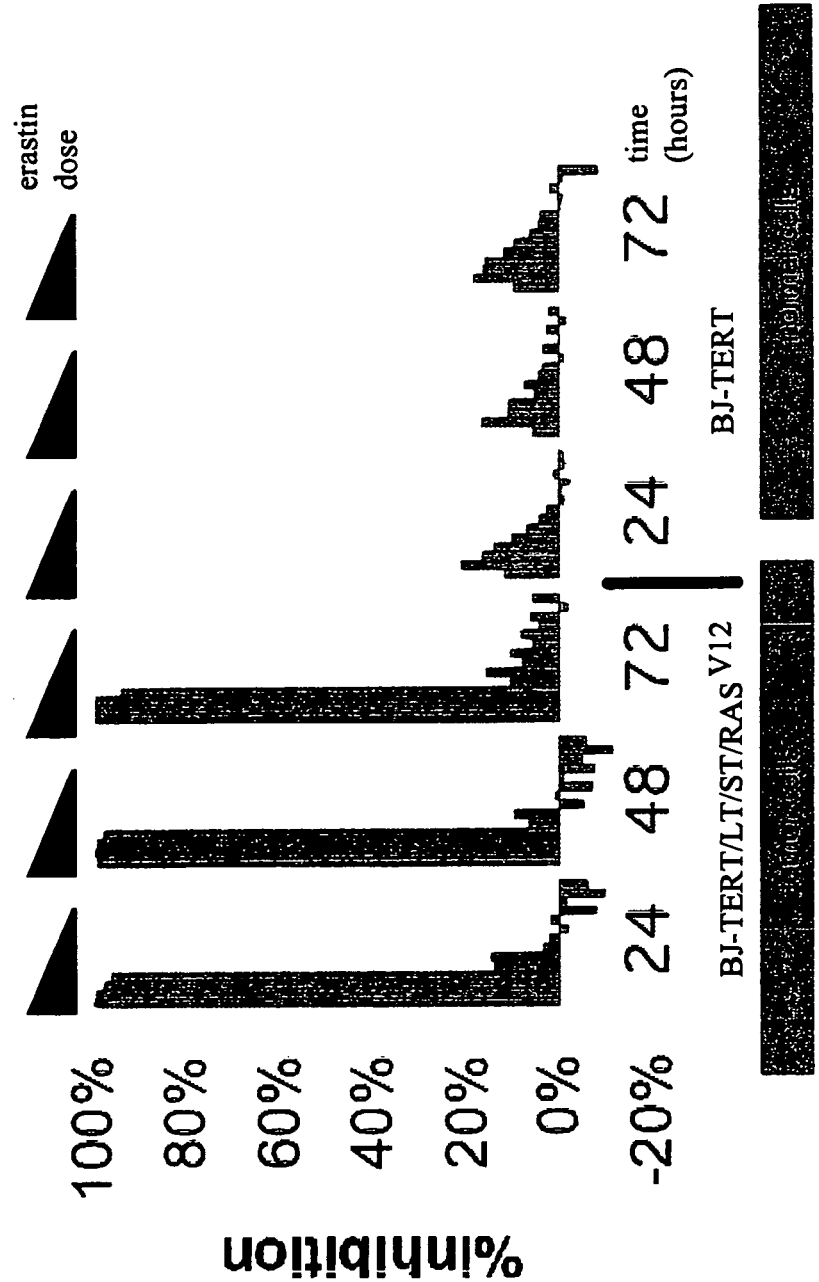

FIG. 35 shows that erastin potency does not increase with longer exposure. A time-dependent effect of erastin on BJ-TERT and BJ-TERT/LT/ST/RASV12 cells. Cells were seeded in 384-well plates in the presence of the indicated concentrations of erastin. Inhibition of cell viability was determined after 24, 48, and 72 hr using calcein AM.

Figure 36:
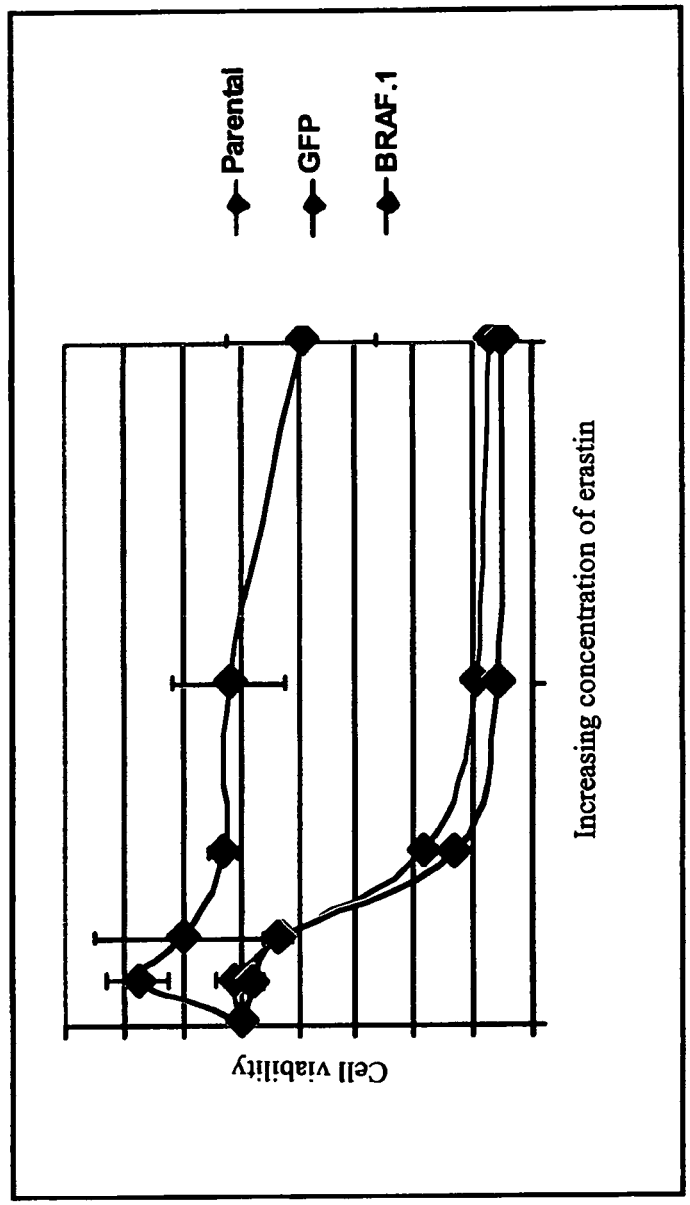

FIG. 36 shows that knockdown of BRAF causes resistance to erastin. A673 Ewing sarcoma cells were infected with a lentivirus encoding an shRNA to BRAF or GFP as a control, or parental uninfected cells. Sensitivity to erastin was measured using Trypan Blue exclusion.

FIG. 37 shows mammalian cell death phenotypes. Mammalian cells die through several different known mechanisms, including apoptosis, necrosis, mitotic catastrophe, autophagic cell death, paraptosis, or the less well defined methods of dark cell death or oncosis.

Figure 38:
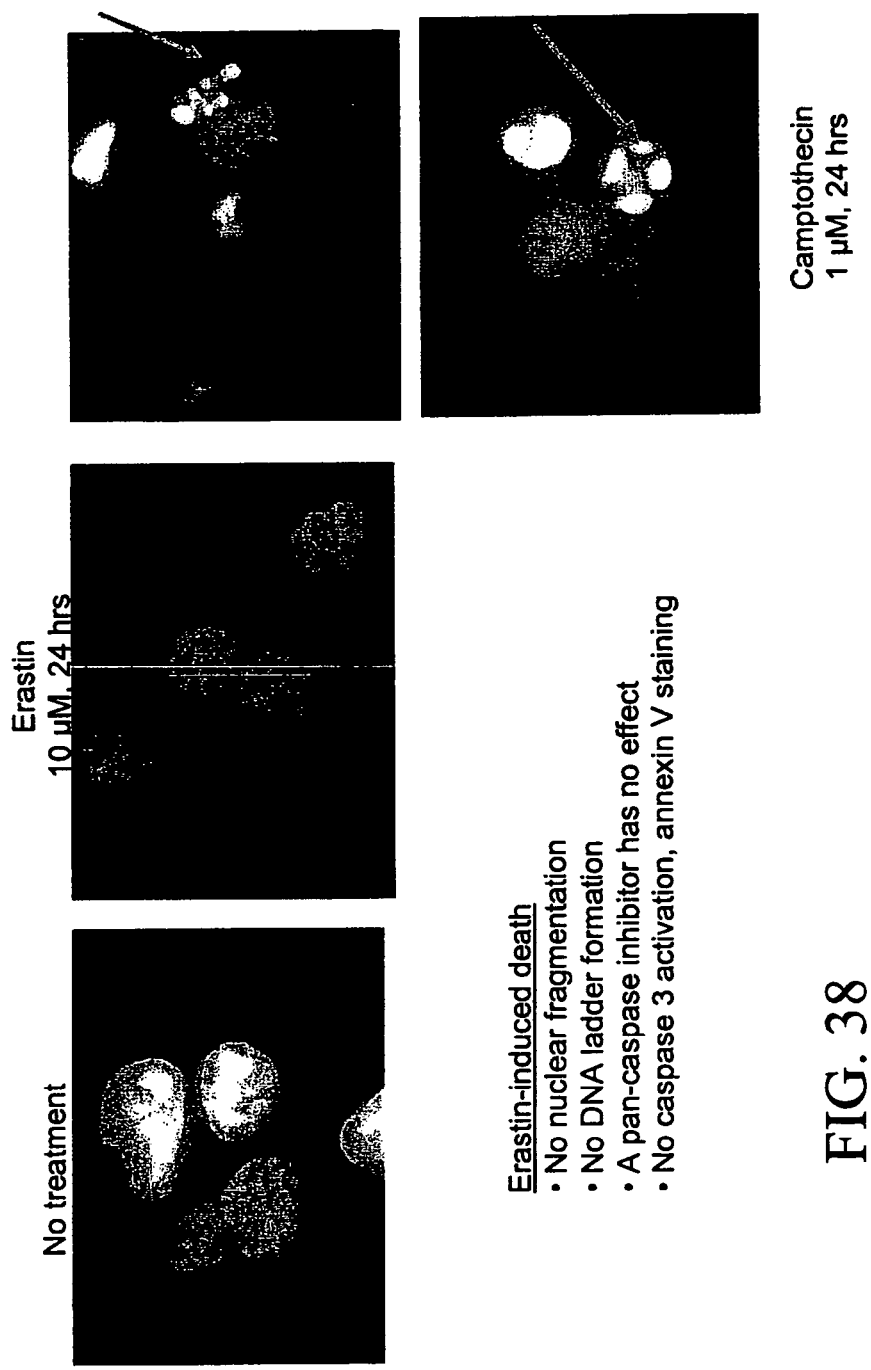

FIG. 38 shows that camptothecin, but not erastin, induces characteristics of apoptosis. Camptothecin-treated, but not erastin-treated, BJ-TERT/LT/ST/RASV12 cells displayed fragmented nuclei (10%-20% of total nuclei, arrows) as shown. DNA was stained used Hoechst 33342.

Figure 39:
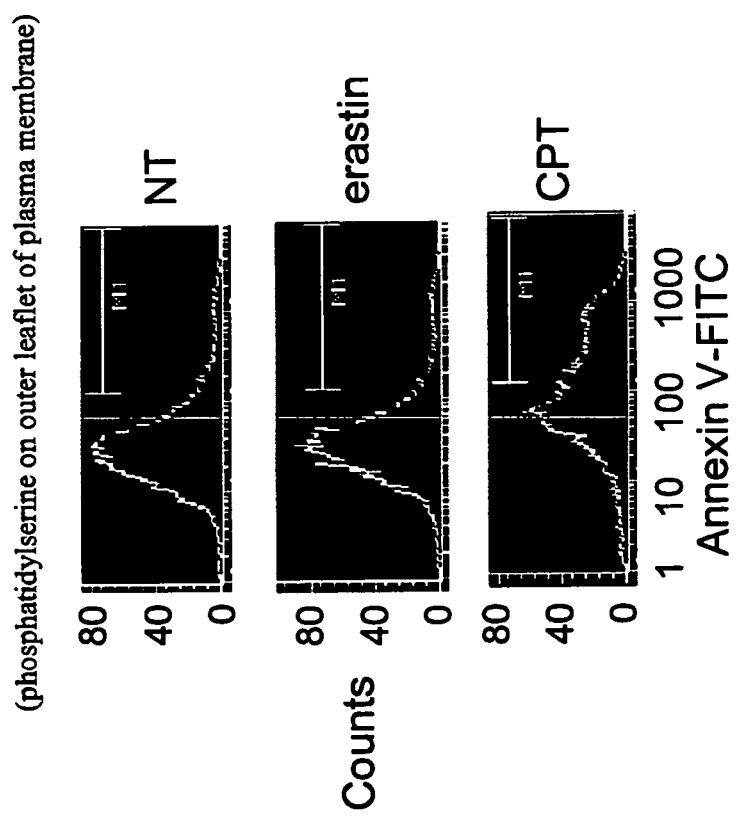

FIG. 39 shows that camptothecin-treated, but not erastin-treated, BJ-TERT/LT/ST/RASV12 cells display Annexin V staining. The percentage of cells in the indicated M1 region were 6%, 6%, and 38% in untreated, erastin-treated (9 μM), and camptothecin-treated (1 μM), respectively.

Figure 40:
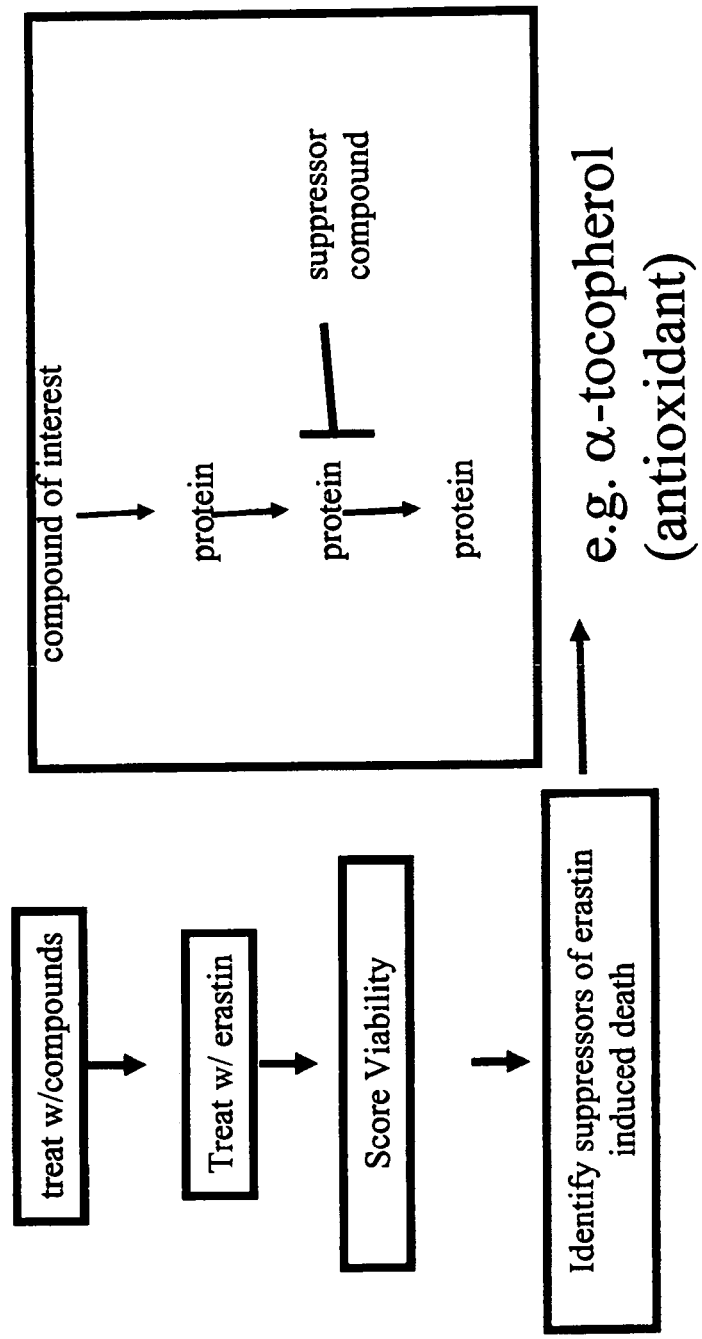

FIG. 40 shows that screens for small molecule suppressors of erastin can reveal the mode of death.

Figure 41:
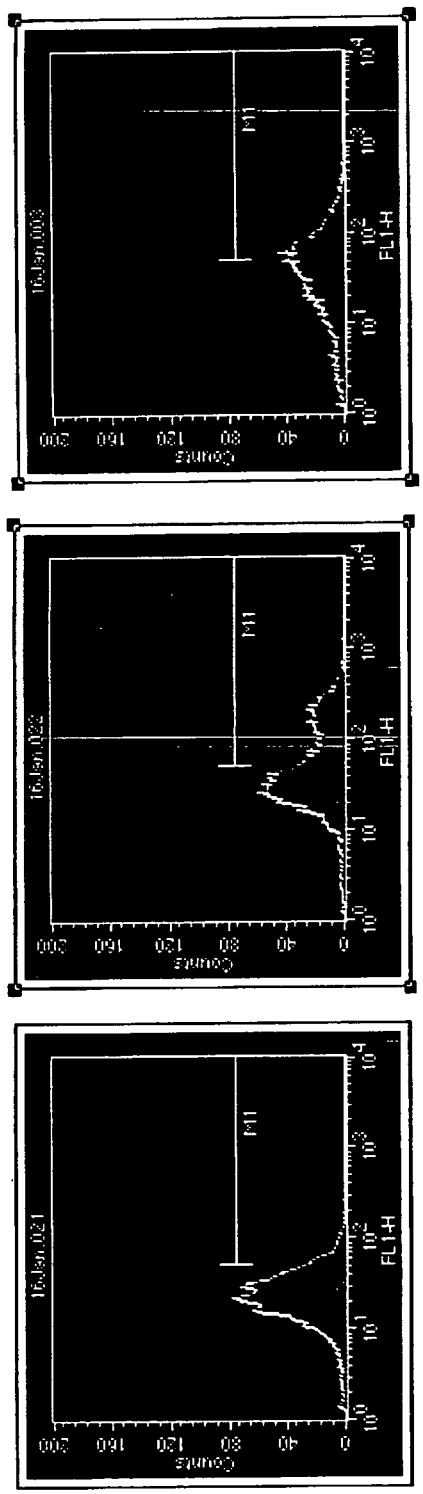
Figure 41:
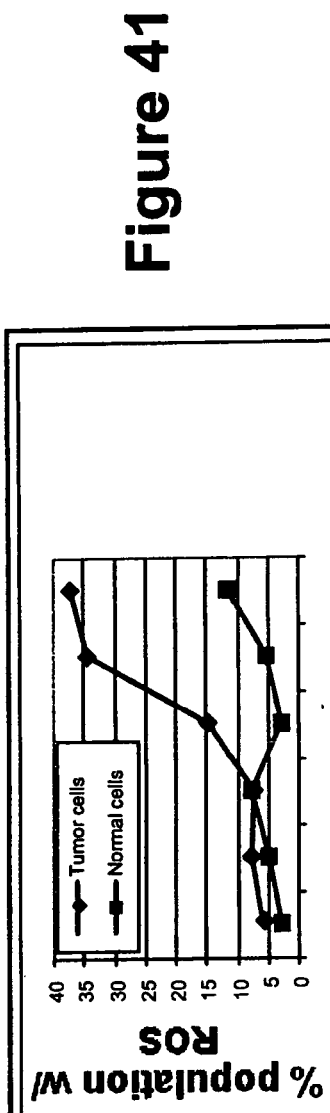

FIG. 41 is a summary of the results from an experiment using flow cytometric analysis using dihydrodichlorofluorescein, which shows that erastin causes the formation of oxidative species. Briefly, cells were treated with erastin for the indicated periods of time and oxidative species determined using dihydrodichlorofluorescein, which becomes more fluorescent upon oxidation. Hydrogen peroxide treatment was used as a control.

Figure 42:
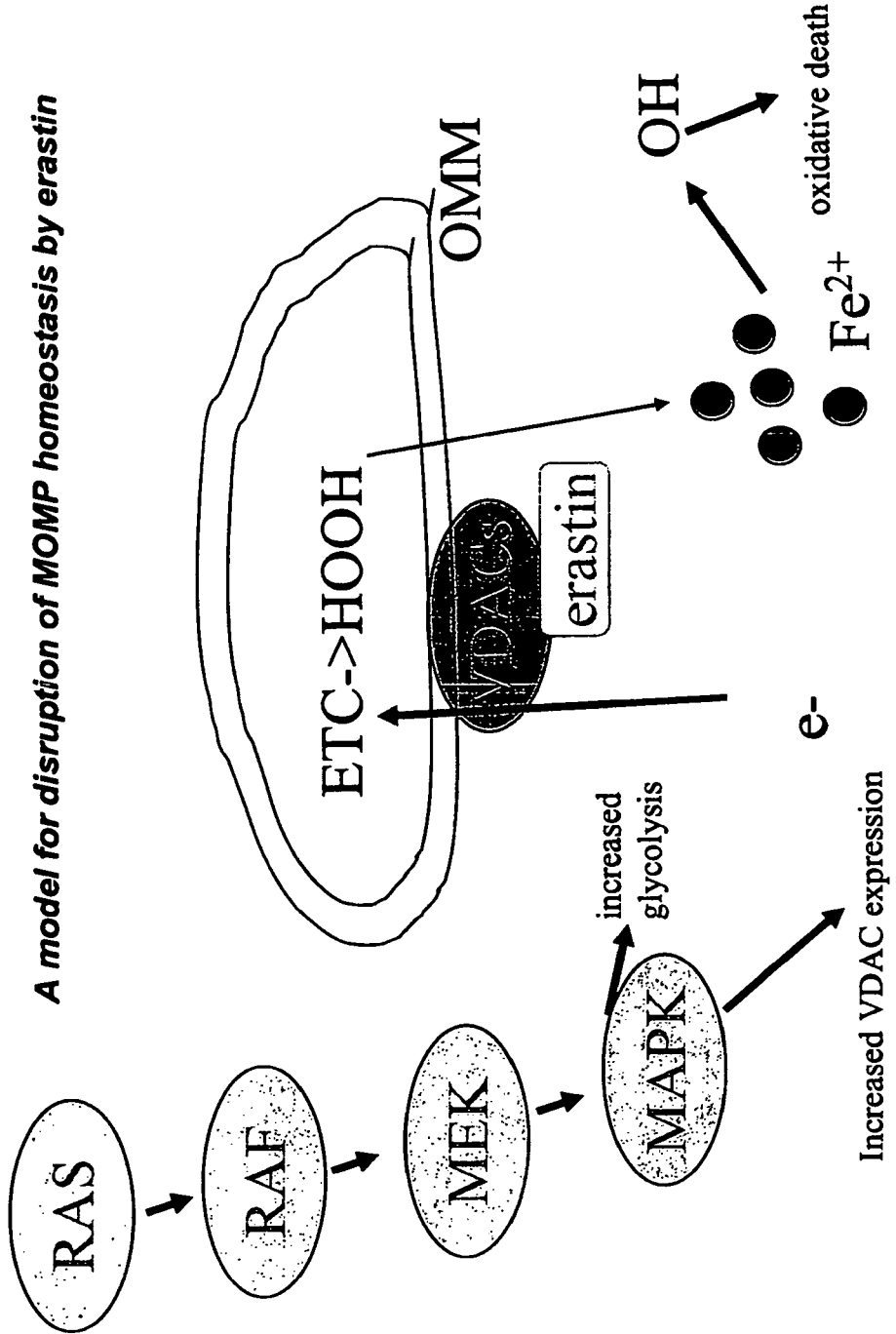

FIG. 42 shows a model for the mechanism of erastin-induced cell death mechanism. RAS-RAF-MEK signaling causes increased glycolysis and increased VDAC expression. Erastin locks VDACs open and causes dysregulated respiration, resulting in oxidative species that react with iron, causing lethal reactive species such as hydroxyl radical.

Figure 43:
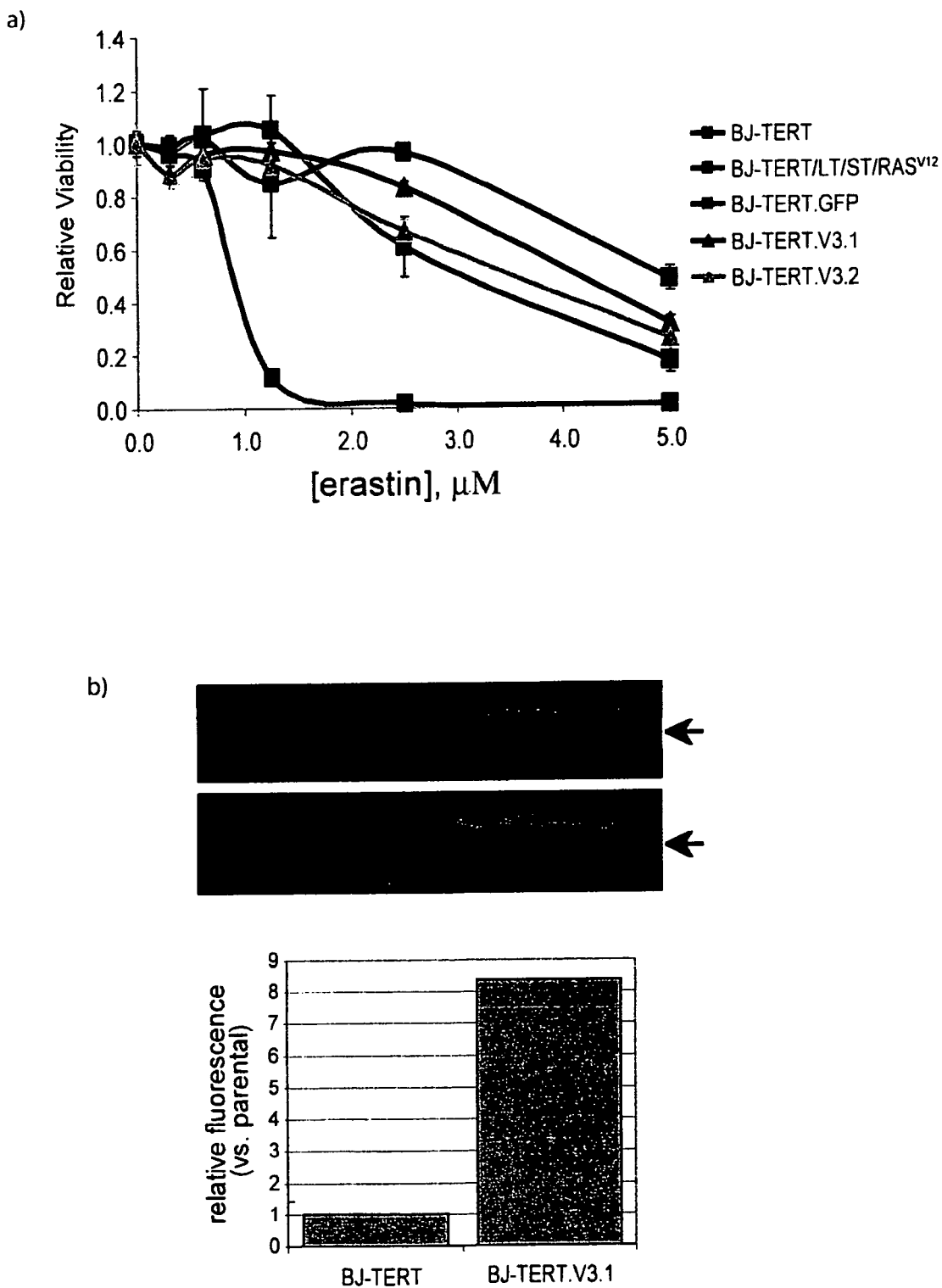

FIG. 43 shows that overexpression of VDAC3 in BJ-TERT cells causes no change in sensitivity to erastin. (a) BJ-TERT cells, infected with virus expressing VDAC3 cDNA were treated with erastin dilutions, and viability, relative to no treatment, was measured using Alamar Blue viability analysis. (b) 2D Western Blot analysis indicates a >8-fold increase in VDAC3 protein expression (arrows) in infected cell lines compared to the parental cell line (BJ-TERT). Unique clones: BJ-TERT.V3.1 and BJ-TERT.V3.2.

Figure 44:
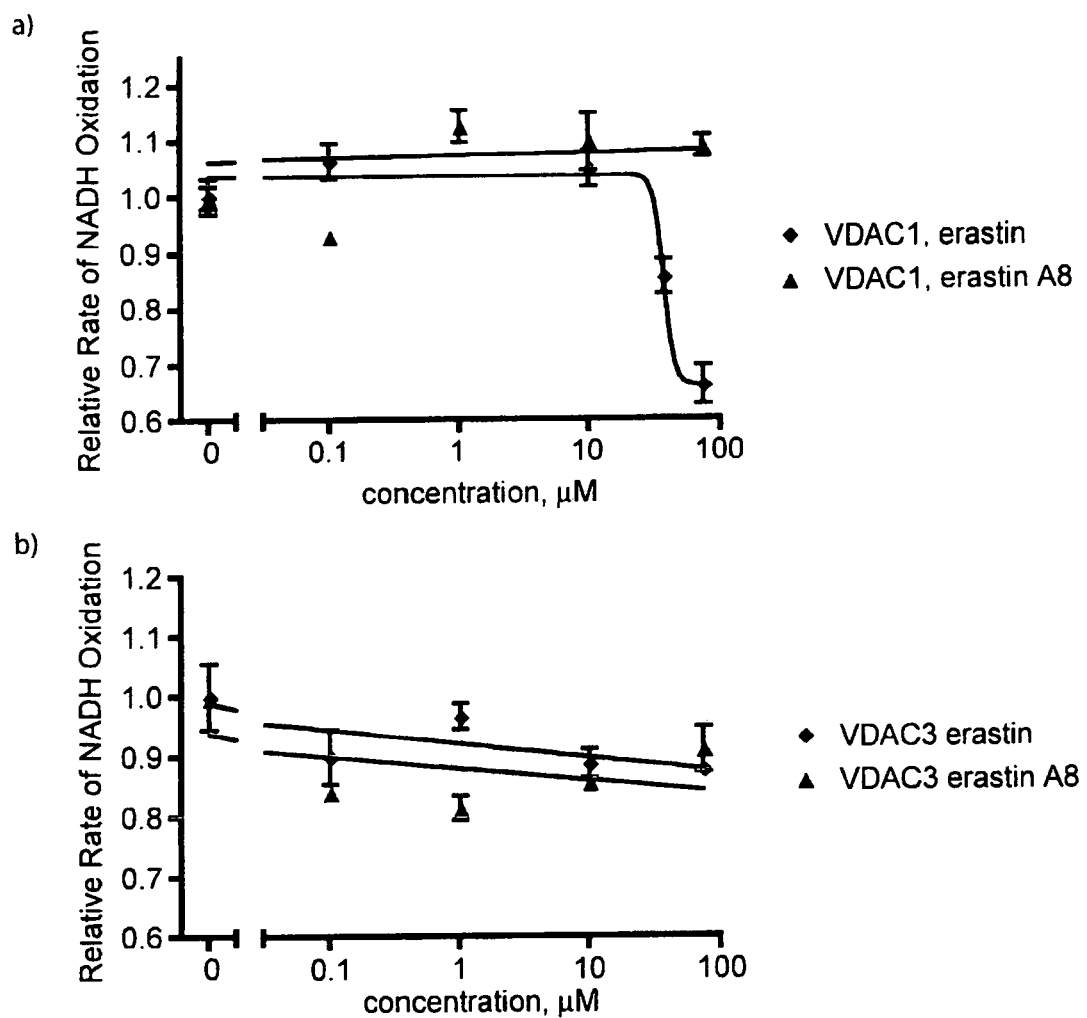

FIG. 44 shows the rate of NADH oxidation in mitochondria in the presence of erastin or an inactive analog, erastin A8. Mitochondria were purified from yeast expressing murine (a) VDAC1 or (b) VDAC3 in place of yeast VDAC (porin). Y-axes shows rate of NADH oxidation relative to no drug treatment.

Figure 45:
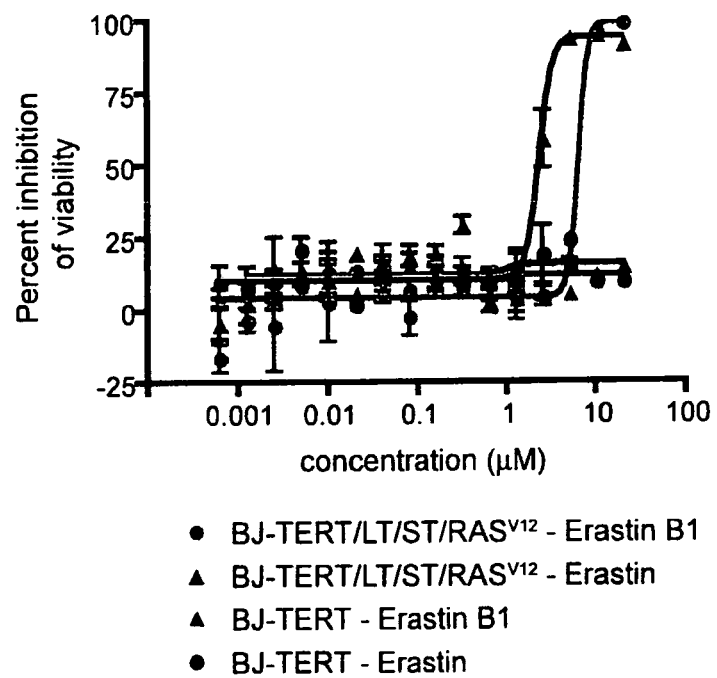

FIG. 45 shows the viability of BJ-TERT/LT/ST/RASV[12] cells in response to 24 hour erastin or erastin B1 analog treatment using an Alamar Blue assay.

DETAILED DESCRIPTION

Definitions

"Oxidative cell death" is a term which refers to cell death which is characterized by the increased level of oxidative species measured in a cell, altered mitochondrial morphology, including enlarged and/or fused mitochondria, in the absence of significant increase in mitochondrial numbers. Oxidative cell death does not manifest typical cellular and molecular markers of apoptosis, autophagy and/or necrosis.

The term "VDAC" refers to one or more VDAC proteins such as VDAC1, VDAC 2, and VDAC3, or any isoform or combination thereof.

BJ-TERT/LT/ST/RASV12 cells are also referred to as BJELR. BJ-TERT/LT/ST cells are also referred to as BJE-HLT. BJ-TERT cells are also referred to as BJEH.

In certain aspects, the invention provides methods to identify genotype-selective compounds, as well as, compounds and mechanisms that cause oncogene-selective lethality. Such compounds eliminate tumor cells harboring specific oncogenic mutations, but have minimal effects on normal cells lacking these mutations. Small molecules with such selective lethality reveal functions of oncogenes, and the molecular and cellular pathways affected by oncogenes, and allow for the creation of selective drugs, which are targeted to specific targets of an oncogenic pathway. In certain aspects, the invention describes a mechanism for selectively eliminating tumor cells, which express oncogenic RAS proteins.

An annotated library of biologically active compounds was assembled[114]. To identify tumor-selective cytotoxic drugs, including compounds from the annotated library, and to study the global patterns of drug activity, software tools were developed to improve the facility with which new tumor-selective compounds can be identified[114, 120-124]. This software was used to discover genotype-selective lethal compounds such as erastin[8]. A cheminformatics and laboratory management system for chemical genetic screens was developed as a custom data analysis tool for analyzing our screening data and we used this to identify erastin and the other RSLs. High-throughput assays generate large quantities of data that require sophisticated data analysis tools[121]. The software tool, SLIMS (Small Laboratory Information Management System), was created to facilitate the collection and analysis of large-scale chemical screening data[124]. Compound structures and raw data are loaded into SLIMS directly from structure data (SD) or platereader (csv) files; systematic spatial errors can be automatically identified and corrected using a discrete-Fourier-transformation tool[120]. Published literature associated with active compounds can be automatically retrieved from Medline and processed to yield potential mechanisms of actions[121]. This software is available through the website Sourceforge (slims.sourceforge.net).

A gene expression signature-based, high-throughput screening method was created in which a gene expression signature is used as a surrogate for cellular states[117]. The annotated compound library was used to identify compounds that induce the differentiation of acute myeloid leukemia (AML) cells. The AML gene signature and a differentiated neutrophil gene signature were defined, and multiplexed single base extension mass spectrometry (SBE-MS)-based RT-PCR was used to detect this gene signature in 384-well plate format. In screening 1,739 biologically active compounds, 8 compounds were identified that reliably induced the differentiation signature and yielded functional evidence of differentiation of AML tumor cells. These results indicate that gene expression signature-based screening may be useful for chemical screening.

A protein-pathway-and-network-alignment software tool was developed. As targets of compounds that mediate RAS-selective killing are discovered, there is a need for software tools to place these proteins in networks and to identify candidate functions of these proteins. The network-alignment software tool implements a strategy for aligning protein-protein interaction networks and pathways that combines interaction topology and protein-sequence similarity to identify conserved protein-interaction pathways and protein complexes[123].

To create an annotated library of biologically active compounds, thousands of small molecules with experimentally verified biological mechanisms and activities were identified, collected and assembled into a screenable format[114]. This annotated library can be used to aid in defining the mechanism of action for RAS-selective lethal compounds, using suppressor and enhancer screens. The library has extensive annotation to identify, in an unbiased fashion, mechanisms that are statistically overrepresented among active compounds from a screen versus the parent library[114]. This approach was used to determine that erastin acts through an oxidative, non-apoptotic mechanism of cell death.

Using high-throughput screening of compounds in isogenic, engineered tumor cell lines, compounds can be discovered that are selectively lethal to oncogenic-RAS-expressing cells. In certain aspects, the invention is directed to a compound called erastin that displays selectivity for tumor cells with activated RAS-RAF signaling. Erastin acts through mitochondrial VDACs to cause an oxidative, non-apoptotic cell death. Defining the mechanism governing erastin-induced cell death illustrate a means of selectively eliminating tumor cells. In certain aspects, the invention establishes the utility of the genotype-selective screening paradigm for discovering anti-tumor agents, including but not limited to agents that target components of the RAS pathway. In other aspects, the invention provides VDAC1, 2, and 3 proteins as drug targets for anti-cancer agents. Using the tools of synthetic chemistry, molecular biology and proteomics, the invention provides that voltage dependent anion channels (VDACs), including VDAC1, 2, and 3, are target proteins for one of these compounds, which is named erastin.

The genetic and mechanistic bases of specific drugs' tumor selectivity were identified through biochemical and molecular approaches. The genetic basis of selectivity for eight known agents and erastin were determined[8]. Furthermore, the invention describes molecular targets, including but not limited to VDAC molecules, of erastin. The invention further provides the mechanism of erastin-induced cell death, provides VDAC1, 2, and 3 molecules as erastin targets, and provides use of erastin and erastin analogs in vivo in mice.

In other aspects, the invention defines the mechanism by which modulation of VDAC activity leads to RAS-selective lethality. In certain embodiments, the invention provides VDAC proteins, including human VDAC1, 2, and 3, as erastin targets. In other embodiments, the invention provides the downstream components and consequences of oncogenic RAS signaling that lead to erastin sensitivity. In other embodiments, the invention provides the use of optimized erastin analogs in mouse cancer models.

In certain aspects, the invention provides that erastin acts through the mitochondrial VDAC proteins to cause an oxidative, non-apoptotic death. The sensitivity of tumor cells to erastin thus reveals that oncogenic RAS signaling causes increases in VDAC levels and that VDACs are gain-of-function targets for cancer therapeutics. The results support the notion of using small molecules to study oncogene function and suggest that VDAC ligands are potential chemotherapeutic agents for the treatment of cancers with activated RAS signaling.

In certain aspects, the invention provides that downstream targets of RAS enable oncogenic-RAS-selective lethality. Furthermore, the invention provides a compound, erastin, and some of its cellular targets, the VDAC proteins. An affinity-based approach was used to identify the targets of erastin.

Non-Limiting Methods to Determine that a Protein is a Target of a Small Molecule:

Once a binding protein such as VDAC is identified, it can be determined whether binding of a compound to the candidate protein is the basis for the compound's phenotypic activity. There are a number of methods to validate candidate targets. Non-limiting examples of such methods are: (i) RNA-interference knockdown, (ii) cDNA-based overexpression, (iii) in vitro binding studies, (iv) photo-crosslinking and (v) creating a binding-defective mutant of the target.

In non-limiting examples, RNA-interference-mediated knockdown and cDNA-based overexpression are methods for decreasing and increasing, respectively, the concentration of a protein. For many small molecules, altering the level of the target protein will alter the compound potency. For example, decreasing the concentration of tubulin, the target of benomyl, causes increased sensitivity to benomyl[28]. In contrast, compounds that act via a gain of function have the opposite relationship with their target proteins: increasing the concentration of topoisomerase I, the target of camptothecin, which acts via a gain of function, causes increased sensitivity to camptothecin[8, 29-39].

In a non-limiting example, in vitro binding studies can determine the binding parameters associated with a small-molecule-protein interaction. A candidate protein is overexpressed, purified and incubated with a test compound. Useful parameters extracted from such experiments are the on-rate, the off-rate, the equilibrium dissociation constant and the entropic and enthalpic contributions to binding affinity. Two methods used to measure protein-ligand interactions are surface plasmon resonance and isothermal titration calorimetry.

In a non-limiting example, photo-crosslinking can identify a binding site for a small molecule on a protein[40-42]. A photoactivatable moiety is incorporated into a compound to enable crosslinking to a target protein. Benzophenones can be photo-activated with long wavelength (>300 nm) light, resulting in less destruction of compounds and proteins. Labeled protein is digested with a protease and labeled peptides are identified with mass spectrometry. In this way, a specific peptide sequence to which a compound is crosslinked is determined, suggesting binding sites.

In a non-limiting example, creating a mutant protein of a target that does not bind to the test compound can be a useful method of assessing the functional relevance of the target-ligand interaction. For example, mutants of the mTOR protein that don't bind its ligand rapamycin were used to show that mTOR is the cellular target of rapamycin[43, 44].

Creation of a Genome-Scale Lentiviral shRNA Collection:

A powerful method of illuminating the mechanism of action of novel RAS-selective lethal compounds is to perform a large-scale suppressor screen with RNA interference reagents that reduce expression of specific mRNAs. Such suppressors might reveal direct targets of compounds, or pathways involved in causing sensitivity to them. Towards this end, 150,000 shRNA constructs may be created in a lentiviral vector. 90,000 constructs were created, sequenced, and protocols needed to perform high-throughput screens with the library in lentiviral format were developed 125.

Target Identification Using Photolabeling with Indoxins, Compounds that Overcome Drug Resistance:

Synthetic lethal screening was used to identify compounds and mechanisms for overcoming E6-oncoprotein-mediated drug resistance. The screen identified compounds that potentiate doxorubicin's lethality in E6-expressing colon cancer cells. Tested compounds were derived from the annotated compound library[114], the National Institute of Neurological Disorders and Stroke (NINDS) library[126], and a library of compounds purchased from Timtec, Interbioscreen and Chembridge, herein referred to as TIC library[127]. The screen identified a group of compounds, that were named indoxins, that overcome doxorubicin resistance[128]. Indoxins potentiate doxorubicin, but not camptothecin or podophyllotoxin, suggesting they act at the level of topoisomerase II abundance. It was found that indoxins upregulate topoisomerase IIα. When the acyl functionality was substituted with a biotin-linked group, indoxins retained activity and selectivity, indicating that affinity reagents can be introduced at this site. Incorporation of a photo-activatable functionality[129, 130] was achieved by preparing an indoxin-benzophenone-fluorescein photo-reactive probe. Protein targets cross-linked to this probe were purified, eluted and sequenced. Two proteins were repeatedly pulled-down with the indoxin probe but not a control probe: myosin IC and ARP2[131]. The ability of indoxins to target nuclear myosin 1C could mediate topoisomersase IIa transcriptional upregulation, as myosin 1c has been linked to transcriptional control: it co-localizes with RNA polymerase II and may affect transcription[131], and is associated with rDNA and required for RNA polymerase I transcription[131]. This demonstrates the photolabeling of a target protein using a benzophenone moiety[128], and that such photolabeling can be used to identify proteins that interact with the photolabeled compound.

Figure 1:
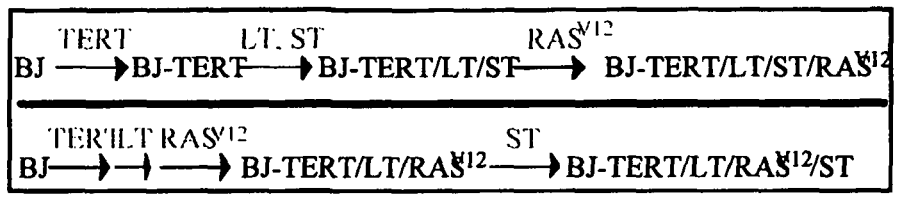
FIG. 1 shows the steps to produce experimentally transformed human cells. BJ cells are primary human foreskin fibroblasts. BJ-TERT cells are derived from BJ cells and express hTERT, the catalytic subunit of the enzyme telomerase. BJ-TERT/LT/ST cells are derived from BJ-TERT cells by introduction of a genomic construct encoding both simian virus 40 large (LT) and small T (ST) oncoproteins. BJ-TERT/LT/ST/RAS$^{V12}$ tumor cells (also referred to as BJELR cells) are derived from BJ-TERT/LT/ST cells by introduction of an oncogenic allele of HRAS (RAS$^{V12}$). BJ-TERT/LT/RAS$^{V12}$ cells are derived from BJ cells by introduction of cDNA constructs encoding TERT, LT, HRAS$^{V12}$, and a control vector. BJ-TERT/LT/RAS$^{V12}$/ST cells are derived from BJ-TERT/LT/RAS$^{V12}$ cells by introduction of a cDNA encoding ST.

Discovery of Erastin, a RAS-Selective Lethal Compound:

To discover oncogenic-RAS-selective lethal compounds, an engineered human tumor cell was used (FIG. 1). hTERT, a genomic construct encoding the Simian Virus 40 large (LT) and small T (ST) oncoproteins, and an oncogenic allele of HRAS (RAS$^{V12}$) were introduced into primary BJ fibroblasts[8, 56, 60]. In another series of engineered cells, complementary DNA (cDNA) constructs encoding LT and ST were used in place of the SV40 genomic construct that encodes both of these viral proteins[57]. In this latter series, ST was introduced in the last stage, enabling the testing of compounds in the presence or absence of ST (FIG. 1).

The screen can identify compounds with increased potency and activity in the presence of RAS$^{V12}$ and/or other genetic elements. 70,000 compounds were screened, comprising 20,000 compounds from a combinatorial library, ~5,000 known biologically active compounds, ~11,000 structurally defined natural products and ~34,000 drug-like synthetic compounds[126, 127]. The primary screen tested in triplicate the effect of treating tumorigenic BJ-TERT/LT/ST/RAS$^{V12}$ cells with each compound for 48 hours at a concentration of 4 µg/mL, corresponding to 10 µM for a compound with a molecular weight of 400. Also, the screen measured cell viability using alamar blue, which undergoes a red shift in fluorescence upon reduction[132], and calcein AM, which becomes fluorescent when cleaved by intracellular esterases[133]. Compounds lethal to BJ-TERT/LT/ST/RAS$^{V12}$ cells (>50% inhibition of viability) were re-tested in a two-fold dilution series in isogenic cells with and without RAS$^{V12}$, to identify those with RAS$^{V12}$-dependent lethality. The IC$_{50}$ value was calculated for each compound in each cell line and thereby five novel compounds were identified that were at least four-fold more potent in HRAS$^{V12}$-expressing cells, compared to HRAS$^{V12}$-deficient cells[8].

The engineered tumor cells make use of dominantly acting viral oncoproteins (LT and ST). These viral proteins are involved in cell transformation in specific forms of cancer, namely simian virus 40-induced malignant mesothelioma[134] and other viral oncogenes (E6 and E7) are involved in human papillomavirus-induced cervical carcinoma[135], and have been used to disrupt p53 and pRB function to transform cells in vitro and in vivo[136-138]. The selectivity of erastin and the other compounds were further established in a cell line expressing dominant negative inhibitors of p53 and pRB not derived from viral elements. This cell line expresses (i) a truncated form of p53 (p53DD) that disrupts the tetramerization of endogenous p53, (ii) a CDK4$^{R24C}$ mutant resistant to inhibition by p16INK4A and p15INK4B (the major negative regulators of CDK4) and (iii) cyclin D1. The effects of these RAS$^{V12}$-selective compounds at a range of concentrations were tested in these cells, BJ-TERT/p53$^{DD}$/CDK4$^{R24C}$/D1/ST/RAS$^{V12}$ (named BJ-DRD) cells. These compounds were found to be active in this cell line (Table 2). Thus, these compounds (including erastin) are effective in tumor cells transformed without viral proteins (other than ST). In addition, these compounds were tested in a second clone of BJ-derived engineered tumor cells (FIG. 2) and found that they were effective in this cell line as well.

Figure 3:
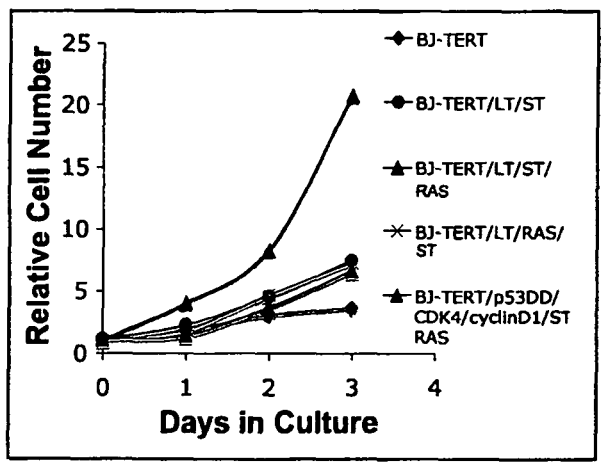
FIG. 3 shows growth rates of engineered cell lines. The relative growth rates of five cell lines were assessed by seeding an equal number of cells and measuring cell number using alamar blue metabolism after 1, 2 and 3 days. BJ-TERT/LT/ST/RAS$^{V12}$ cells grow faster than the other lines. BJ-TERT cells grow more slowly than the other cell lines. The rates of growth of the other three cell lines are the same. This information was used to ensure that RAS-selective lethal compounds such as erastin are not simply selective for rapidly dividing cells. Compounds with RAS selectivity should differentially affect the three cell lines that grow at the same but have different oncogenic RAS status.
Figure 4:
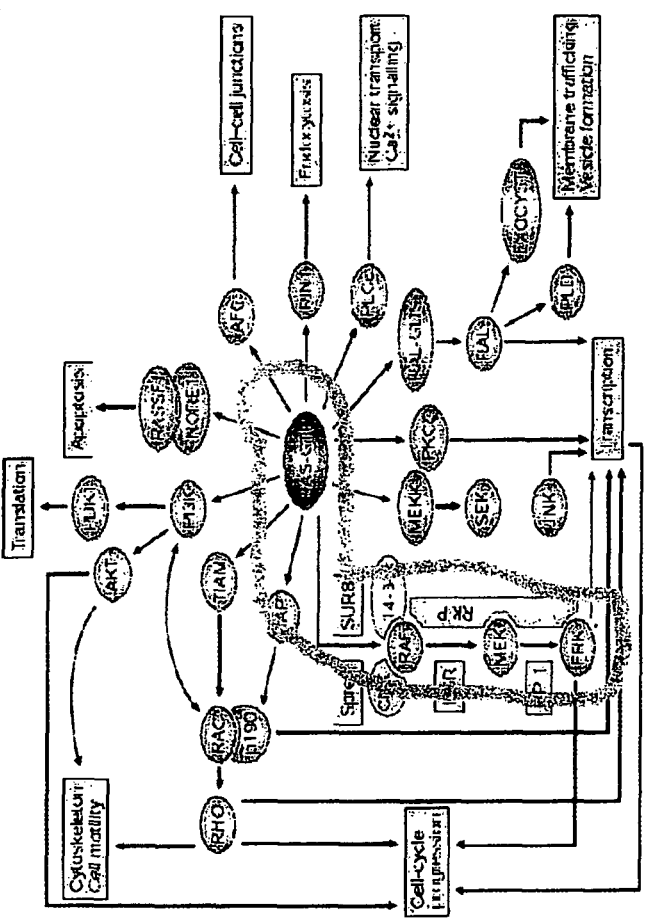
FIG. 4 shows that oncogenic RAS activates numerous signaling pathways. The RAS-RAF-MEK-ERK pathway is particularly important in causing sensitivity to erastin-induced death. From Malumbres and Barbacid, *Nature Reviews Cancer,* 3:7-13 (2003).

BJ-TERT/LT/ST/RAS$^{V12}$ cells grow more rapidly than BJ-TERT/LT/ST cells lacking RAS"[2]. Thus the activity of each compound was measured in BJ-TERT/LT/RAS$^{V12}$/ST cells, which were engineered independently and contain cDNA constructs for LT and ST (whereas BJ-TERT/LT/ST/RAS$^{V12}$ cells contain the genomic LT construct), and in BJ-DRD cells (described above). Truly oncogenic-RAS-selective lethal compounds should be equally active in all 3 of these cell lines. BJ-TERT/LT/ST/RAS$^{V12}$ cells grow more rapidly than BJ-TERT/LT/RAS$^{V12}$/ST or BJ-DRD cells (FIG. 3). Thus, compounds that are targeting a mechanism dependent on the rate of cell division should be more active in BJ-TERT/LT/ST/RAS$^{V12}$ cells compared to BJ-TERT/LT/RAS$^{V12}$/ST or BJ-DRD cells. On the other hand, compounds that are acting in a cell-division-rate-independent manner should be equally active in all three of these cell lines, as they all contain HRAS$^{V12}$.

Figure 2:
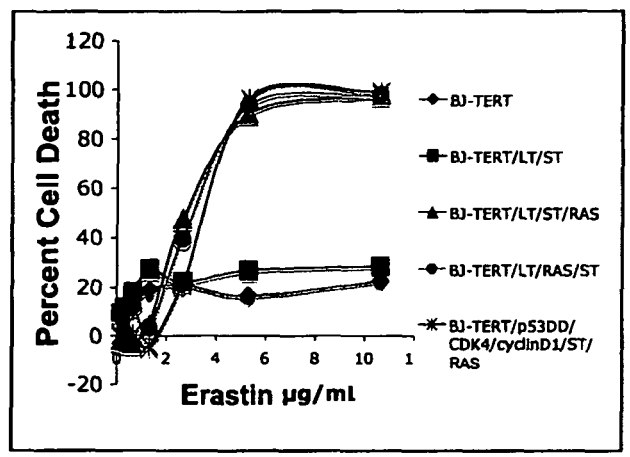
FIG. 2 shows RAS-selective lethality of erastin in engineered tumor cells. Erastin was tested in a dilution series in five engineered cell lines derived from primary BJ fibroblasts. Cells were incubated with erastin for two days at 37° C. with 5% $CO_2$, Alamar blue was added (10% final volume) and fluorescence measured (530 nm ex, 590 nm em). Cell lines harboring oncogenic RAS (triangles, circles and x's) were sensitive to erastin, but isogenic lines lacking oncogenic RAS (squares and diamonds) were resistant. Two different clones of engineered tumor cells (circles and triangles) responded similarly. In addition, replacement of the viral oncogene LT with mutants of p53, CDK4 and cyclin D did not change erastin sensitivity (purple X's).

Erastin was equally effective in the slower growing engineered cells, suggesting they act in a manner that is independent of the rate of proliferation (e.g. FIG. 2). In addition, longer treatments and higher concentrations had little effect on the viability of engineered cells lacking RAS$^{V12}$, confirming the qualitative nature of their selectivity (see Dolma et al[8]).

Voltage Dependent Anion Channels:

In certain aspects, the invention provides that one of these RAS-selective lethal compounds, which was named erastin, acts through the voltage dependent anion channels (VDACs). VDACs, also known as mitochondrial porins, are small membrane-spanning channels that facilitate the transport of ions and metabolites across membranes, most notably the outer mitochondrial membrane[61]. There are three human VDAC genes, VDAC1, VDAC2 and VDAC3, of which VDAC1 is the most studied[62, 63]. The three gene products are ~70% identical, and likely have distinct cellular and organismal functions; for example, Vdac1-null mice are viable but have altered respiration in striated muscle, whereas Vdac3-null male mice are infertile, but otherwise healthy[65]. Murine embryonic stem cell lines have been generated lacking each Vdac gene, demonstrating that individual Vdac genes are not essential for cell viability[63]. In addition, mice have been generated lacking both Vdac1 and Vdac3, demonstrating that an organism can survive with just one of the three Vdac isoforms[63].

Although no atomic-resolution structure of a VDAC protein is available, these proteins have been proposed to adopt a beta barrel fold analogous to the bacterial porins, based on amino acid sequence similarity and CD spectra[66, 67]. Unlike bacterial porins, however, the eukaryotic VDACs are gated by membrane voltage in vitro. In the closed state, ions, but not small molecules, can penetrate through VDAC pores. In the open state, both ions and metabolites can pass through VDAC pores. The mechanism of channel gating in vivo is not established, although protein regulators of VDAC activity are reported to exist[68]. The amino-terminal segment of VDACs has been proposed to negatively regulate channel conductance[69]. In support of this hypothesis are the findings that (i) mutations in this region change voltage dependence in vitro[70], and (ii) truncation of part of this region causes loss of voltage dependence[69]. Immunostaining suggests that the amino-terminal helix of VDACs points towards the intermembrane space[71, 72]. While VDAC1 has been found to exist in a large protein complex with a molecular weight of 2 MDa, VDAC2 has been found to exist as a monomer, such as an oligomer, and possibly in a small multi-protein complex with a molecular weight of 230 kDa[73]. Human VDAC1 has been reported to be localized to the plasma membrane, in addition to its primary localization in the mitochondrial outer membrane[74-81]. VDAC1's role in the plasma membrane is enigmatic; it has been proposed to function as an NADH:ferricyanide-reductase. VDACs interact with hexokinase[82], the permeability transition pore[83], inter-mitochondrial membrane contact sites[84], the mitochondrial protein import complex[85] and microtubule associated protein-2 (MAP-2)[86]. VDACs have been reported to interact with BCL proteins and to participate in the formation of the mitochondrial permeability transition pore that facilitates release of cytochrome c from mitochondria[87-89]. VDACs may regulate access of metabolites to the mitochondrial inter-membrane space. In yeast, NADH is transported into mitochondria through yeast VDAC[90]. Finally, VDAC permeability has been linked to cell survival[91], demonstrating that regulated opening of VDACs occurs in a physiological context.

Cell Death Pathways:

There are at least three types of mammalian cell death: (i) apoptotic death, (ii) autophagic death and (iii) necrotic death[92, 93]. Apoptosis is an intrinsic death program[94] involving activation of cysteine proteases (caspases)[93, 94]. Autophagic death involves self-digestion of cellular material through formation of lysosome-like autophagosomes[95]. Necrosis is a passive death process that involves loss of cellular homeostasis[96]. Markers of apoptosis (Table 1) include cleavage of PARP1 from 113 kD to 85 kD[97], staining of by Annexin V[98], release of cytochrome c from mitochondria[99], cleavage of chromosomal DNA[100], TUNEL staining[100], margination of chromatin[101], activation of caspases[102] and decreased cell size[99] (Table 1, column 2). Markers of necrotic cell death include increased PARP activity[97], clumping of chromatin[92, 93, 96, 103], decreased intracellular [ATP][92, 93, 96, 103], increased cell size and formation of reactive oxygen species[96] (Table 1, column 3). Markers of autophagic death include autophagosomes[95, 104, 105], sensitivity to 3-methyladenine (3-MA) and increased lysosomal activity (Table 1, column 4)[95, 104, 105]. Overlapping phenotypes exist: it is possible to activate apoptotic-like mechanisms without caspases, or mixed apo-necrototic death[103]. Other possible death programs include paraptosis and mitotic catastrophe[106-113].

Erastin Activates Non-Apoptotic Cell Death:

Among oncogenic-RAS selective lethal (RSL) compounds, erastin is attractive as a drug. Erastin is synthetically accessible and has at least 16-fold RAS-selective lethality. To define the mechanism of action of erastin, a two-pronged strategy was taken which involves: (i) a top-down approach, which characterized the type of cell death caused by erastin, and (ii) a bottom-up approach, which identified direct binding proteins for the erastin scaffold.

To characterize the type of cell death induced by erastin, the effect of erastin was tested alongside camptothecin and staurosporine, which induce apoptotic cell death[39]. Apoptosis is characterized by alterations in nuclear morphology, including pyknosis, karyorhexis and margination of chromatin[93]. Nuclear morphology of camptothecin-treated and erastin-treated BJ-TERT/LT/ST/RAS$^{V12}$ cells was monitored using fluorescence microscopy. Although karyorhexis and margination of chromatin were visible in camptothecin-treated cells, no such morphological alternations were visible in erastin-treated cells (Dolma et al[8]). Further supporting the notion that erastin-induced death is non-apoptotic were the observations that: (i) erastin does not induce DNA fragmentation (i.e. formation of a DNA ladder), (ii) that a pan-caspase inhibitor (50 μM Boc-Asp(Ome)-fluoromethyl ketone[139]) does not block cell death induced by erastin, (iii) that erastin does not cause increased Annexin V staining (see Dolma et al.), (iv) that erastin does not cause the appearance of a caspase 3 active fragment[8], (v) that PARP1 is not cleaved upon treatment of cells with erastin (FIG. 5), and (vi) that cytochrome c is not released from mitochondria upon treat-

TABLE 1

Markers of different cell death phenotype, including markers for the oxidative cell death provided by the invention

| MARKER | APOPTOTIC DEATH | NECROTIC DEATH | AUTOPHAGIC DEATH | OXIDATIVE CELL DEATH |
|---|---|---|---|---|
| poly(ADP)ribose polymerase | cleavage to 85 kDa form | Increased activity | unknown | no cleavage no activation |
| Annexin V staining | increased | no change | no change | no |
| DNA laddering | yes | no | no | no |
| TUNEL staining | yes | sometimes | no | no |
| Nuclear morphology | margination/ fragmentation | clumping, karyolysis | partial condensation | no changes |
| ATP | no change/small decrease | Large decrease | no change | small decrease |
| Cell size | decrease | increase | increase | |
| Caspase activation | yes | sometimes | no | no |
| ROS generation | sometimes | yes | no | yes |
| Suppressed by Z-VADfmk? | yes | no | no | no |
| Cytochrome c release | yes | sometimes | no | no |
| Mitochondrial morphology | — | — | — | altered: enlargement, fusion of mitochondria |

Figure 6:
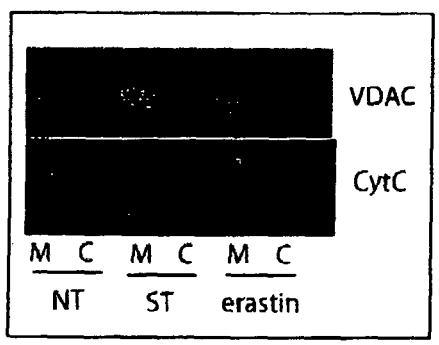
FIG. 6 shows that erastin does not induce cytochrome c release from mitochondria. BJ-TERT/LT/ST/RAS$^{V12}$ cells were seeded in polystyrene 100×20 mm dishes in 10 ml media. After overnight incubation at 37° C. with 5% $CO_2$, the cells were treated with nothing (NT), staurosporine (ST, 1 µM) or erastin (20 µg/mL) for 6 h, washed with 10 mL ice-cold PBS and lysed by passage through a 25-gauge needle (five strokes). Cell lysates were centrifuged at 1850 rpm for 5 min at 4° C. to remove the nuclear fraction. Mitochondria were removed from the soluble cytosolic fraction by pelleting at 10,000 rpm. Supernatant and mitochondrial pellets were solubilized in SDS-PAGE loading buffer and analyzed by western blot using anti-cytochrome c and pan-VDAC antibodies and IR-dye-linked secondary antibodies. VDACs are mitochondrial proteins, so their absence in the cytosolic lane indicates effective separation of cytosol (C) from mitochondria (M). Fluorescence was detected on a LI-COR Odyssey infrared scanner.

Abbreviations: 3-MA:3-methyladenine;
TUNEL: terminal deoxynucleotidyl transferase-mediated dUTP-biotin nick end labeling;
ATP: adenosone triphosphate;
ROS: reactive oxygen species;
Z-VADfmk: N-benzyloxycarbnyl-Val-Ala-Asp(O-Me)-fluoromethyl ketone.

ment with erastin (FIG. 6). Apoptosis-inducing compounds (staurosporine and/or camptothecin) were tested alongside erastin in all of these assays to confirm the functionality of the assay. Unlike many anti-tumor agents[140], erastin does not activate apoptosis. Therefore, in certain aspects the invention provides a genotype-selective anti-tumor agent which induces cell death via a non-apoptotic mechanism of oxidative cell death.

Erastin Induces Genuine Cell Death:

Viability was quantified using calcein AM and alamar blue. BJ-TERT/LT/ST/RAS$^{V12}$ cells treated with erastin rounded up and detached, failed to exclude the vital dye Trypan Blue, displayed a loss of mitochondrial membrane potential as assayed by the potentiometric dye JC-1, and had a small cell size characteristic of dead cells. Loss of viability induced by erastin was irreversible once completed, in that BJ-TERT/LT/ST/RAS$^{V12}$ cells treated with erastin for 24 hours were unable to recover when re-plated in erastin-free medium. Thus, erastin induces rapid, irreversible, non-apoptotic cell death in a RAS$^{V12}$-dependent fashion.

Figure 7:
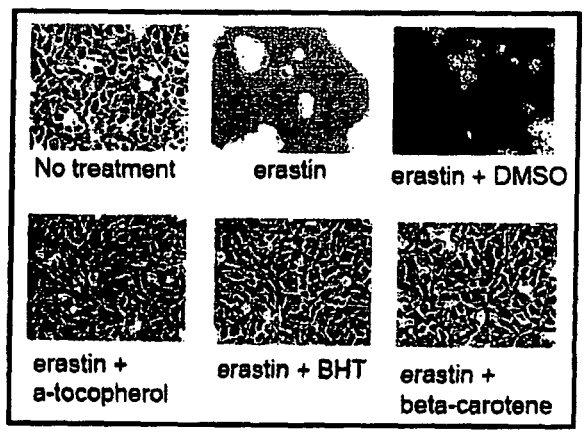
FIG. 7 shows that Anti-oxidants suppress erastin-induced death. BJ-TERT/LT/ST/RAS$^{V12}$ cells were treated as indicated for 24 hours and photographed. Abbreviations: DMSO, dimethylsulfoxide; BHT, butylated hydroxytoluene [erastin] =9 µM.

Erastin Activates Oncogenic-Ras-Dependent Oxidative Cell Death:

In certain aspects, the invention provides that oncogenic cells, such as for example, oncogenic cells caused by RAS$^{V12}$ signaling, treated with erastin undergo a rapid, oxidative cell death process. To define the type of cell death initiated by erastin, a suppressor screen was performed using a library of ~2,000 biologically active compounds[114] (from the Annotated Compound Library). It was found that antioxidants (e.g. alpha-tocopherol, butylated hydroxytoluene and beta-carotene) prevented erastin-induced death (FIG. 7).

Figure 5:
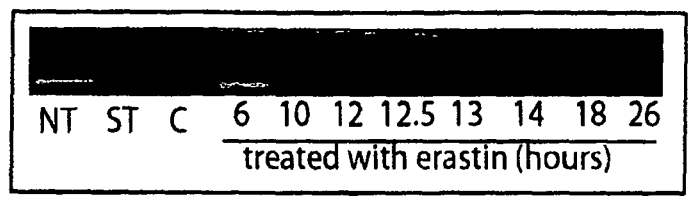
FIG. 5 shows that PARP1 is not cleaved in response to erastin treatment. BJ-TERT/LT/ST/RAS$^{V12}$ tumor cells were seeded in six-well dishes, incubated overnight at 37° C. with 5% $CO_2$ and were treated with nothing (NT), staurosporine (ST, 1 µM) for 6 h, camptothecin (C, 1 µM) for 18 h, or erastin (20 µg/mL) for the indicated time, lysed and analyzed by western blot with an anti-PARP1 antibody. A relatively high concentration of erastin was used to ensure loss of PARP cleavage was not due to a concentration-dependent effect. PARP1 (top band) is cleaved from 110 kD to 85 kD in response to staurosporine, is degraded in response to camptothecin and is unaffected by erastin (by 18 h, erastin-treated cells are almost all dead and little protein remains).
Figure 8:
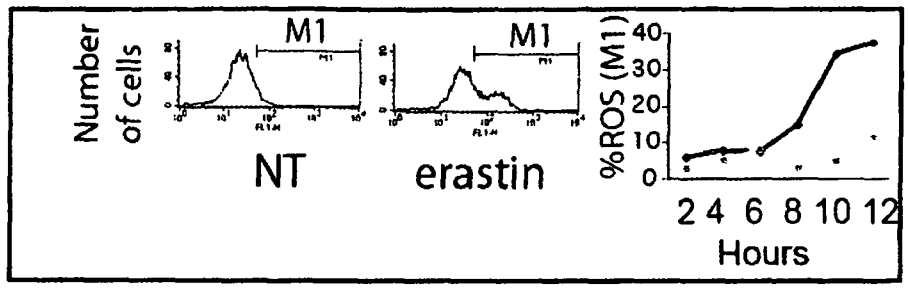
FIG. 8 shows that erastin-induced formation of oxidative species requires activated RAS signaling. BJ-TERT/LT/ST/RAS$^{V12}$ cells (shown in histogram plots and in line graph, dark line) and BJ-TERT cells (shown in line graph only, light line) were treated with 4.6-1 µM erastin and the level of intracellular oxidative species determined using 2'7'-dichlorodihydrofluorescein diacetate (H$_2$DCF-DA, Molecular Probes) and flow cytometry. Cells were seeded at 3×10$^5$ cells per dish in 60-mm dishes and allowed to grow overnight. Cells were incubated with 10 µM of H$_2$DCF-DA for 10 minutes, harvested by trypsinization, washed twice with cold PBS, re-suspended in 100 of PBS and incubated with 5 µl of 50-1 µg/ml propidium iodide for 10 minutes. 400 µl of PBS was added and the solution analyzed by flow cytometry (FACSCalibur-Becton-Dickinson).

Moreover, an oxidizing species were detected in response to erastin treatment in BJ-TERT/LT/ST/RAS$^{V12}$ cells, but not in BJ-TERT cells lacking RAS$^{V12}$ (FIG. 8; in certain experiments, BJ-TERT was used as a control cell line because the Small T oncoprotein does cause modest sensitivity to erastin, possibly by activating the RAS-MAPK pathway). The oxidizing species do not cause PARP cleavage, cytochrome c release or other hallmarks of apoptosis (FIGS. 5, 6). Thus, erastin-induced cell death appears to involve a direct oxidative death. The mechanism of erastin induced cell death is in contrast to other anti-tumor agents that induce the formation of oxidative species along with activation of apoptotic death.

Several observations suggested that erastin-induced oxidative species originate in mitochondria. First, antimycin, a mitochondrial complex III inhibitor[141, 142] and 2-methoxyestradiol (2-ME), a superoxide dismutase inhibitor[143, 144] both partially suppressed erastin-induced cell death (Table 3, note that BJELR is a shorthand for BJ-TERT/LT/ST/RAS$^{V12}$ cells). Both compounds act upstream of mitochondria-generated hydrogen peroxide and hydroxyl radical (potential oxidative species). However, melatonin, a peroxynitrite scavenger[145], did not affect erastin-induced cell death, suggesting peroxynitrite is not involved.

Peroxisome proliferators (ciprofibrate, ciglitazone and clofibrate) and xanthine oxidase inhibitors (oxypurinol and allopurinol) did not affect erastin-induced cell death. Lipoxygenase inhibitors, prostaglandins, arachidonate esters and acids, and thromboxane receptor antagonists had no effect on erastin-induced cell death, suggesting lipoxygenases and arachidonic acid pathways are not involved. In addition, verapamil (an MDR pump inhibitor) had no effect on erastin sensitivity, suggesting MDR activity is not involved in the differential sensitivity of cells to erastin.

Erastin Inhibits Growth of Tumor Cell Lines with Activating Mutations in NRAS, KRAS or BRAF:

Given that oncogenic RAS activates at least four downstream pathways, analysis was performed to identify which downstream effects were necessary for erastin sensitivity. In certain embodiments, the invention provides that erastin inhibits growth and kills genuine tumor cells with RAS mutations. In other embodiments, the invention provides measures of the dose-response of 29 tumor cell lines to erastin, wherein there is at least 50% inhibition of viability in 18 of the cell lines (Table 4). Numerous sarcoma-derived tumor cell lines were sensitive to erastin, consistent with the fact that erastin was discovered in an engineered tumor cell line created from human fibroblasts.

Figure 11:
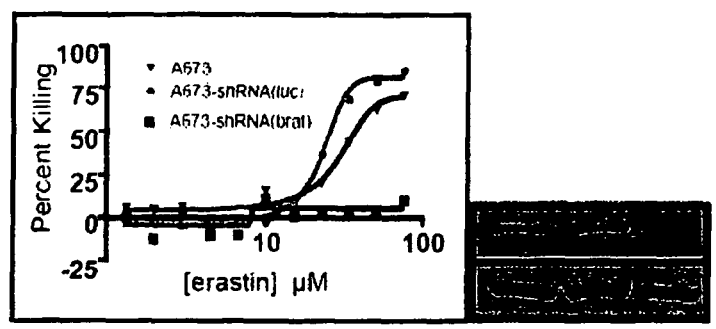
FIG. 11 shows that oncogenic BRAF is required for erastin sensitivity. A673 cells and stable derivatives were treated with erastin, and viability measured using Alamar Blue (Panel on the right). The stable lines expressed a short hairpin RNA (shRNA) targeting BRAF or, as a control, luciferase. A673 cells were infected with pSIRIPP-derived retroviruses expressing shRNAs against BRAF or luciferase, and were selected in 2 ug/ml puromycin. Knockdown was confirmed by western blot (panel on the left)—lane 1 (left): A673 cells, lane 2 (middle): +shRNA(luc), lane 3 (right): +shRNA (BRAF). Top band=BRAF, bottom band=tubulin (loading control).

In non-limiting examples: HT1080 fibrosarcoma cells, with a known activating mutation in NRAS[146], were sensitive to erastin; Calu-1 lung carcinoma cells and MIA PaCa-2 pancreatic cancer cells, with known mutations in KRAS, were sensitive to erastin; A673 cells, with a known V599E activating mutation in BRAF[147], were sensitive to erastin (FIG. 11). BRAF is a direct target of RAS proteins. For some cell lines, it is not known whether they have activating mutations in RAS pathway proteins, or whether they harbor other mutations that activate the RAS-RAF-MEK-MAPK pathway. Activation of RAS has even been observed in the absence of direct RAS mutations[148]. Thus, for some cell lines, it may not possible to directly correlate erastin sensitivity with RAS mutation status.

For cell lines with known activating mutations in RAS pathway components, the necessity of such mutations for erastin sensitivity can be tested. To determine whether the activating mutation in BRAF in A673 cells influences erastin sensitivity, short-hairpin-RNA-expressing plasmids targeting either BRAF mRNA or, as a control, luciferase (LUC) mRNA were created. Stably-transfected cell lines containing these constructs were generated and cell line sensitivity to erastin was measured (FIG. 11). A673 cells containing the control LUC-shRNA construct were sensitive to erastin, but A673 cells containing a BRAF-targeted shRNA were resistant to erastin. This effect was confirmed using a second shRNA construct targeting BRAF, and again there was resistance to erastin when BRAF was knocked down.

In addition, a cDNA construct expressing BRAF that is not targeted by the shRNA was used to demonstrate the specificity of the shRNA constructs. In this set of experiments, A673 cells were co-infected with a BRAF$^{V599E}$ expression vector and a BRAF-shRNA expression vector, wherein the co-expression of the non-targetable BRAF mutant restores sensitivity to erastin. These experiments confirm that knockdown of mutant BRAF causes resistance to erastin. As a control, all the shRNA-containing cell lines were equally sensitive to the cytotoxic compounds doxorubicin and phenylarsine oxide, demonstrating no change in overall drug sensitivity.

Figure 12:
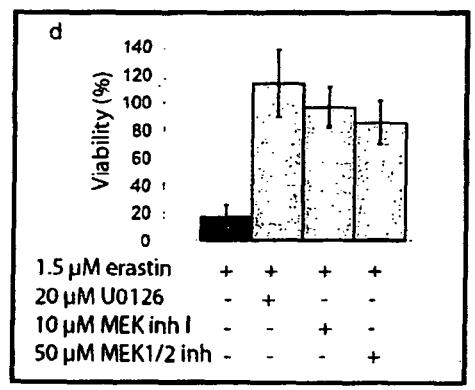
FIG. 12 shows that MEK1/2 inhibitors suppress erastin lethality. BJ-TERT/LT/ST/RASV12 engineered tumor cells were treated with the indicated concentrations of erastin and each MEK1/2 inhibitor for 24 hours and viability was determined by Trypan Blue exclusion. Similar results were obtained in HT1080 tumor cells harboring an NRAS activating mutation.

In further support of the notion that the RAS-RAF-MEK pathway sensitizes tumor cells to erastin, three different MEK1/2 inhibitors were found to suppress erastin's lethality in two different cell lines (FIG. 12). In another aspect, there is correlation between phospho-ERK1/2 abundance and erastin sensitivity in sarcoma cell lines (correlation coefficient=0.41) . Therefore, the RAS-RAF-MEK pathway is an important factor in determining sensitivity to erastin.

Figure 14:
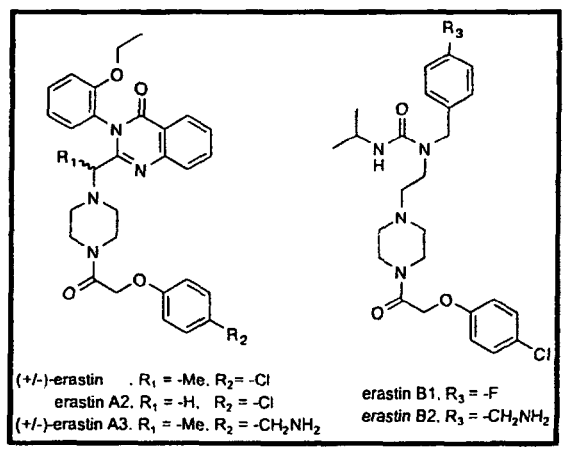
FIG. 14 shows structures of various erastin analogs of the present invention. Erastin A2, lacking the methyl group at R1, is as active as erastin itself (IC$_{50}$=2.5 µM). Erastin A3, containing an aminomethyl group at R2, retains BJELR selective lethality (IC$_{50}$=25 µM in BJELR cells). Erastin B1 is an active analog (IC$_{50}$=10 µM in BJELR cells). Erastin B2 is inactive analog of B1, with an aminomethyl group in the R3 position (no lethality up to 50 µM). Thus, erastin A3 was used as an affinity reagent and erastin B2 was used as a potential negative control, although its loss of activity could be due to other factors than target binding, such as membrane permeability

Identification of VDACs as Erastin-Binding Proteins:

To identify direct protein targets of erastin, erastin analogs were synthesized that could be linked to a solid-phase resin. Replacement of the p-chloro substituent in erastin with an aminomethyl group resulted in an analog (erastin A3, FIG. 14) that retained the ability to selectively kill BJ-TERT/LT/

ST/RAS$^{V12}$ cells. Replacement of the p-fluoro group in erastin B1 (an analog of erastin with nearly equal activity, selectivity and potency) with an aminomethyl group resulted in an analog (erastin B2, FIG. 14) lacking activity in cells.

Erastin A3 and erastin B2 were immobilized on resins to identify proteins that interact with the A3 resin but not the B2 resin. Using BJ-TERT/LT/ST/RAS$^{V12}$ cell lysates, all three isoforms of the human mitochondrial voltage-dependent anion channels (VDAC1, VDAC2 and VDAC3) were identified on the A3 resin, and some VDAC1 was identified on the B2 resin. Using BJ-TERT cell lysates, a small amount of VDAC1 was identified on the A3 resin, but no VDAC was identified on the B2 resin. No VDAC proteins were identified on a control resin lacking any erastin analog. It thus appears that erastin A3 interacts more productively than erastin B2 with VDAC2 and VDAC3. Moreover, all three VDACs were identified with higher confidence from BJ-TERT/LT/ST/RAS$^{V12}$ cell lysate, suggesting VDACs are expressed at a higher level in these cells. Higher level of VDACs expression in BJ-TERT/LT/ST/RAS$^{V12}$ was confirmed (see FIG. 10). The finding that erastin pulls down mitochondrial proteins (VDACs) was consistent with the previous finding showing that erastin induces a mitochondria-driven oxidative death.

Figure 10:
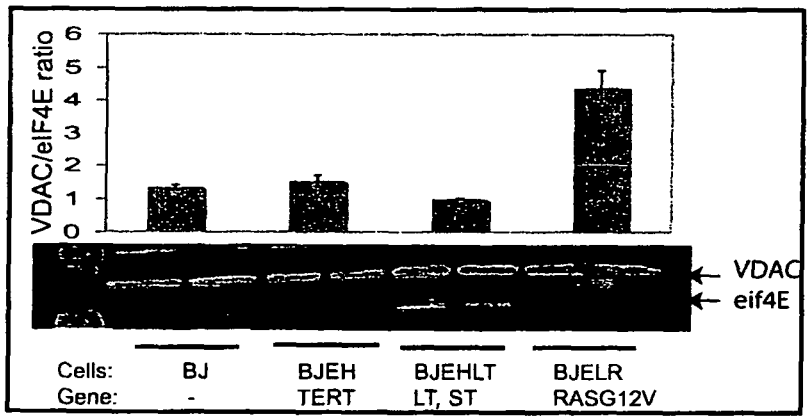
FIG. 10 shows that VDAC proteins are more abundant in the presence of oncogenic RAS. Western blot of BJ-derived engineered cell lysates using a pan-VDAC antibody (Abcam, top band) that recognizes all three isoforms. A control protein (eIF4E) is shown as a loading control. The ratio of VDAC/eIF4E is plotted for each cell line. Error bars represent one standard deviation. Membranes were scanned using the Licor Odyssey Imaging System.

VDAC Proteins are Upregulated by Oncogenic Ras Signaling:

In certain aspects, the invention provides that altered expression of VDACs contribute to erastin sensitivity. To determine whether VDACs are upregulated in response to oncogenic RAS signaling, VDAC abundance was measured, using an antibody that recognizes all three isoforms, in the BJ cell series (primary BJ cells, BJ-TERT cells, BJ-TERT/LT/ST cells, and BJ-TERT/LT/ST/RAS$^{V12}$ cells). In the presence of oncogenic RAS, total VDAC protein was increased about four-fold (FIG. 10). There was no increase in mitochondria number in BJ-TERT/LT/ST/RAS$^{V12}$ cells as measured by a flow cytometric assay, suggesting the greater abundance of VDAC proteins is due to specific upregulation of these proteins and not due to increased mitochondrial biogenesis. Thus, in certain aspects the invention provides connection between oncogenic RAS proteins and VDAC proteins, including VDAC protein expression. In certain embodiments, the protein level of VDAC1, VDAC2, VDAC3, or any combination thereof is increased. In other embodiments, the mRNA level of VDAC1, VDAC2, VDAC3, or any combination thereof is increased. In certain aspects, the invention provides an increased level of VDAC proteins, or mRNA as a biomarker to identify a tumor cell whose growth or viability can be inhibited by an agent which induces oxidative death. Non-limiting examples of such agents are erastin, and its active analogues. In certain embodiments, the tumor cell is derived from a subject who suffers from a tumor. In certain embodiments, the biomarker is an increased protein level of VDAC1, VDAC 2, and/or VDAC3, or any isoform, or any combination thereof, in a tumor cell compared to syngeneic or isogenic cell.

In certain embodiments, there is loss of mitochondrial membrane potential in >70% of BJ-TERT/LT/ST/RAS$^{V12}$ cells after 13 hours of erastin A1 treatment (JC-1 stain), and morphological changes in mitochondria examined by EM, consistent with the notion that erastin induces mitochondrial dysfunction.

In certain aspects, the invention provides that erastin acts by a gain-of-function mechanism and that cells with more VDAC proteins are more sensitive to erastin. A gain-of-function mechanism operates in cells which have increased levels of topoisomerase I and are thus more sensitive to camptothecin[149]. In certain embodiments, upregulation of VDAC proteins, VADC1, 2, and/or VDAC3 by nucleofection caused an increase in sensitivity to erastin, wherein the measured increase is about two to three-fold (FIG. 32 panels (e) and (f)). A control nucleofection process did not change the potency (i.e. the IC$_{50}$) of podophyllotoxin, a microtubule depolymerizer that acts through an unrelated mechanism. In other embodiments, cell lines can be stably transfected with vectors expressing VDAC1, 2, and/or 3. Thus, increased VDAC expression leads to erastin sensitivity which is consistent with a gain of function mechanism. Furthermore, a knockdown of VDACs causes erastin resistance.

Knockdown of VDACs Causes Erastin Resistance:

A lentiviral short hairpin (shRNA) construct was used to reduce expression of VDAC proteins through RNA interference. Vector (pLKO.1) was used to generate 90,000 shRNA constructs targeting more than 18,000 human and mouse mRNAs[125]. This vector has been validated as an effective means of knocking down many mRNAs in human and mouse cells, without inducing an interferon response. All constructs generated are sequenced and several hundred have been verified for their ability to knock down their intended mRNA target[125].

Figure 15A:
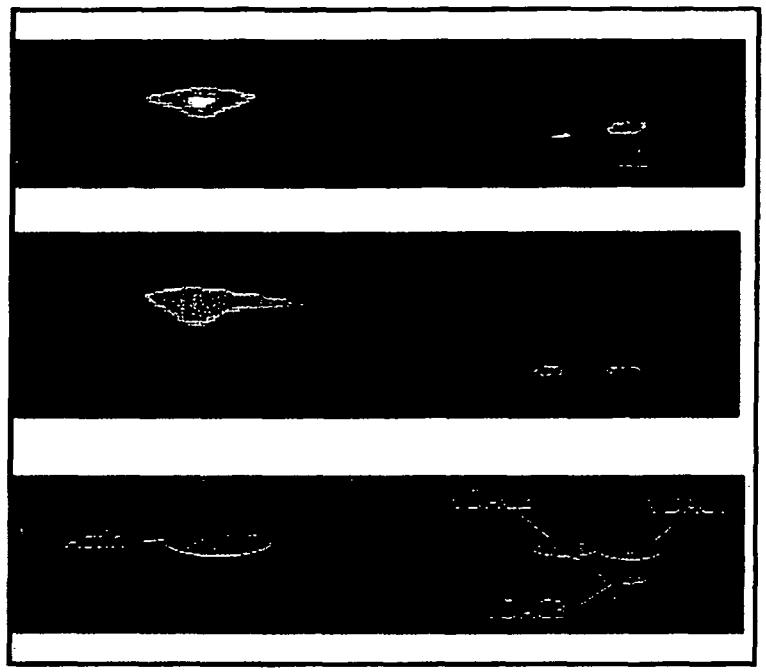
FIG. 15 shows that knockdown of VDAC3 causes resistance to erastin. VDAC3 was knocked down in HT1080 cells using a shRNA vector and viability was measured. FIG. A: VDAC3 knockdown was confirmed at the protein level, 2D gel showing 3 VDAC isoforms and actin. Knockdown was also confirmed by qPCR. FIG. B: sensitivity to erastin was measured by Trypan Blue exclusion (red line-diamond symbol). As a control, an shRNA targeting GFP was used (black line).
Figure 15B:
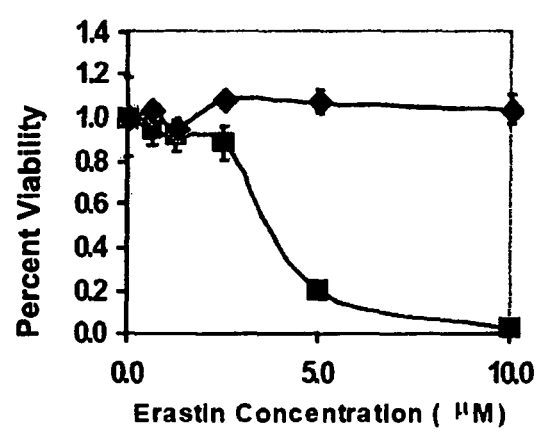
Figure 16:
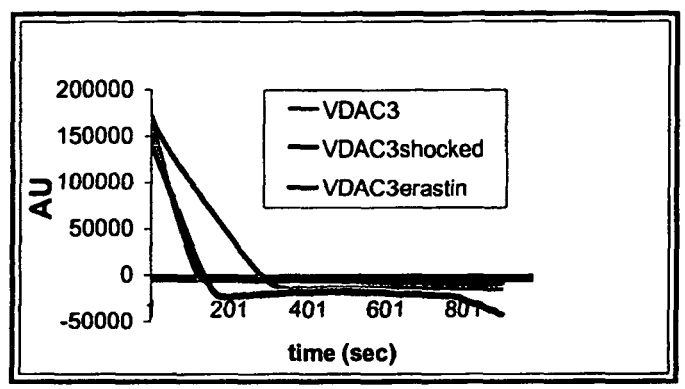
FIG. 16 shows that erastin increases the flux of NADH through VDAC3-containing outer mitochondrial membranes. Mitochondria were isolated from yeast expressing murine VDAC3 in place of yeast VDAC. The rate of NADH oxidation by an inner membrane NADH dehydrogenase was determined by measuring the change in NADH absorbance over time. Mitochondria with a disrupted outer membrane show an increased rate of NADH oxidation (red, shocked) compared to untreated mitochondria (green). Erastin increased the rate of NADH oxidation, presumably by opening VDAC3 (black).

Five lentiviral pLKO.1-based constructs targeting each VDAC isoform were created. These constructs were tested for their effect on erastin sensitivity and the results showed that VDAC2-targeted and VDAC3-targeted shRNAs caused significant resistance to erastin. These findings were consistent with the pulldown experiment, in that they both indicated a preferential role for VDAC2 and VDAC3 in mediating erastin's effects. These constructs cause knockdown of their specific isoform targets at the mRNA and protein level (FIG. 15A). In certain embodiments, reducing expression of VDAC3 causes complete resistance to erastin. In other embodiments, reducing expression of VDAC2 causes partial resistance to erastin. This is consistent with a gain-of-function model and provides evidence that VDACs are functionally implicated in the erastin-induced cell death mechanism.

Figure 13:
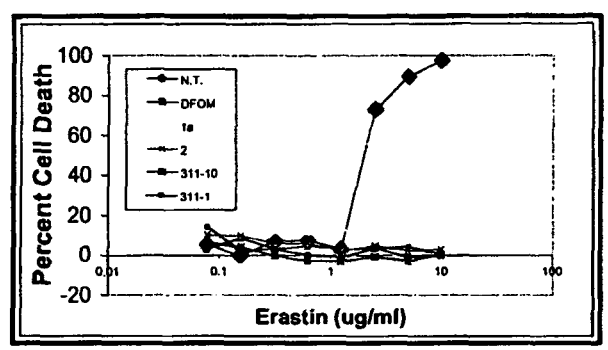
FIG. 13 shows that iron chelators suppress erastin lethality. BJ-TERT/LT/ST/RAS$^{V12}$ cells were treated with erastin and four different iron chelators, desferrioxamine mesylate (DFOM), the compounds 1a and 2 whose structures are shown in FIG. 30, and the compound "311" (311-10 or 311-1) (Green, D. A, et al., Inhibition of Malignant Cell Growth by 311, a novel iron chelator of the pyridoxal isonicotinoyl hydrazone class: Effect on the R2 subunit of ribonucleotide reductase. Clinical Cancer Research, (7): 3574-3579 (2001). Cell killing was measured by Alamar Blue assay.

Iron Chelators Suppress Erastin Lethality:

Given that erastin-induced death is oxidative, it is likely that Fe$^{2+}$ is necessary for erastin's lethality. Fe$^{2+}$ reacts with peroxides in a catalytic cycle through Fenton chemistry to generate hydroxyl radicals that react with proteins, lipids and nucleic acids. The effect of iron chelators, such as for example, the iron chelators shown in FIG. 30, on erastin's lethality were evaluated in BJ-TERT/LT/ST/RAS$^{V12}$ cells. Iron chelators completely suppressed erastin's lethality (FIG. 13). These data show that Fenton chemistry is involved in erastin-induced oxidative death, and that iron is necessary for erastin's lethality.

In certain aspects, the invention provides that erastin interacts with a VDAC-containing mitochondrial complex to induce mitochondrial dysfunction, release of oxidative species and cell death via non-apoptotic mechanism. This mechanism is selective for cells with activated RAS or RAF signaling, because oncogenic RAS/RAF upregulate VDACs (FIG. 10). Thus, cells with greater RAS, RAF or MEK activity have an increased pool of VDACs and are more susceptible to compounds that dysregulate VDAC function. In certain embodiments, the dysregulation of function can be by locking VDACs in an open conformation and causing excessive respiratory activity. Because RAS$^{V12}$-expressing cells are more glycolytic, they also accumulate higher levels of NADH, which would normally affect VDAC closure; it is likely that erastin prevents this effect, leading to excessive respiratory activity and oxidative species.

Preclinical Assessment of Erastin:

The stability of erastin in mouse and human liver microsomes and in mouse and human plasma was assessed. In both human and mouse liver microsomes, after 1 hr, ~30% of erastin was converted to its primary metabolite (the O-de-ethylated product). In both human and mouse plasma, only ~10% of erastin was lost after five hours. Thus, erastin has sufficient metabolic and plasma stability to be tested in vivo in mice.

Measuring the Effects of Erastin on VDAC1, 2 and 3 In Vitro:

Overexpression and purification of the three human VDAC isoforms. Human VDAC1, VDAC2 and VDAC3 can be overexpressed and purified[89, 150]-152. cDNA clones for the human VDACs are cloned, using PCR, restriction digests and sequencing to verify each clone, into the E. coli expression vector pET-15b (Novagen). Amino-terminally hexahistidine-tagged VDAC fusions proteins are produced in BL21 cells and purified from inclusion bodies, as described for S. cerevisiae VDAC purification from E. coli[152]. The pET vectors contain a thrombin-cleavage site, allowing optional removal of the affinity tag after purification. Purity is assessed by SDS page, reactivity with both N- and C-terminally directed antibodies, MALDI-TOF MS, HPLC, CD and voltage-dependent gating in lipid bilayers. For example, with VDAC3, the cDNA clone was transformed into E. coli, expression was induced with 0.5 mM IPTG and cells were grown overnight. After pelleting the cells, the resuspended pellet was incubated with lysozyme and TX-100. The resulting lysate was sonicated and centrifuged, washed and resuspended in solubilization buffer (100 mM NaCl, pH 8.0 Tris-HCl, 6M Gdn-HCl). After removal of cell debris by centrifugation, the supernatant was applied to Ni affinity columns (BD biosciences), drained by gravity flow, and eluted with solubilization buffer containing 50 mM imidazole. After adding LDAO (Sigma) to a final concentration of 2%, Gdn-HCl was dialyzed against storage buffer. The resulting protein was pure on a Coomasie-Blue-stained SDS gel. VDAC1 and VDAC2 are purified in an analogous manner. All three VDAC proteins can be fully characterized biochemically after the purification.

In a non-limiting method for native VDAC purification, recombinant VDAC proteins can be isolated, and purified, from S. cerevisiae harboring each murine or human VDAC isoform in place of the yeast VDAC, using a protocol known in the art[153]. In a non-limiting embodiment, murine and human VDAC2 and 3 were purified from yeast strains. Isolation of mitochondria was as described by Daum et al. (Lipids of mitochondria. Biochim Biophys Acta. 822(1):1-42 (1985)), except cells were lysed using a Dounce homogenizer after Zymolyase treatment. The mitochondrial pellet was then lysed by incubating in a 50 mM Tris pH 7.5, 2.5% TX-100 solution for 30 minutes with gentle shaking and then by centrifuging at 27000 g-s to remove debris. The supernatant was run on a Sepharose Q FF column (Amersham) using a NaCl (0.1-1M) gradient. The appropriate fractions were collected and concentrated using Centricon 10 (Fisher Scientific) tubes. The purity was analyzed by SDS-PAGE, reactivity with anti-VDAC antibody and mass spectrometry. Murine VDAC1 can be purified in a similar manner. This procedure typically yields up to 1 mg of native VDAC proteins that have not been refolded, which is advantageous for lipid bilayer experiments.

In other embodiments for VDAC protein purification, mitochondrial outer membranes can be isolated from human cells lacking some and overexpressing specific VDAC isoforms. In one embodiment, stably transfected cell lines overexpressing VDAC 1 (using zeocin and pcDNA3) can be generated, wherein in certain embodiments these cell lines can contain short hairpin RNA (shRNA) constructs that eliminate expression of VDAC2 and VDAC3. Selection of these cell lines can be accomplished using puromycin. In another embodiment, stably transfected cell lines overexpressing VDAC2 (using zeocin and pcDNA3) can be generated, wherein in certain embodiments these cell lines can contain short hairpin RNA (shRNA) constructs that eliminate expression of VDAC1 and VDAC3. Selection of these cell lines can also be accomplished using puromycin. In another embodiment, stably transfected cell lines overexpressing VDAC3 (using zeocin and pcDNA3) can be generated, wherein in certain embodiments these cell lines can contain short hairpin RNA (shRNA) constructs that eliminate expression of VDAC2 and VDAC1. Selection of these cell lines can also be accomplished using puromycin.

cDNA clones for human VDAC1, VDAC2 and VDAC3 and five shRNA clones specifically targeting each VDAC isoform, i.e. 15 shRNA constructs total in the pLKO.1 lentiviral shRNA vector, have been constructed, some of which completely eliminate expression of each isoform (See, e.g., Table 7). qPCR and 2D gels can confirm that the HT1080 fibrosarcoma-derived clones transfected with shRNA vectors, indeed express a single VDAC isoform. Outer mitochondrial membranes from such cell lines can be isolated using established methods[74, 153].

Measurement of Erastin Isoform-Binding Specificity Using SPR and Calorimetry:

In certain embodiments, surface plasmon resonance (SPR) can be used to measure the affinity of the interaction between an agent which induces oxidative cell death, such as for example erastin, and any of the isoforms of the VDAC proteins. Purified, hexahis-tagged, recombinant VDAC protein can be immobilize on a Biacore sensor chip using antibody capture, with an anti-his antibody, and the change in SPR signal in the presence of erastin can be measured. Native, non-refolded VDAC proteins, which, of example, can be derived from yeast strains harboring murine or human VDAC isoforms knocked into the yeast VDAC locus, can be immobilized on a sensor chip using an Abcam pan-anti-VDAC antibody. Proteins such as GST, avidin and bovine serum albumin can serve as negative protein controls. Erastin B1 and camptothecin, or any other unrelated compound can be used as negative small molecule controls. To use SPR, VDAC proteins can be solubilized in a buffer containing 20 mM Tris (pH 7.0), 0.1 M $(NH_4)_2SO_4$, 10% glycerol, protease inhibitor tablet and 1% lipid/detergent mixture drawn from various combinations of lipids, such as DOPE (1,2-dioleoyl-sn-glycero-3-phosphoethanolamine), DOPS (1,2-dioleoyl-sn-glycero-3-phospho-L-serine) and DOPC (1,2-dioleoyl-sn-glycero-3-phosphocholine). The solubilized protein can be captured on an anti-his antibody immobilized on a CM4 Biacore sensor chip, or an anti-VDAC antibody immobilized on a sensor chip. A Biacore 3000 optical sensor can be used to perform these measurements[154, 155]. Erastin A3 can be immobilized on a Biacore chip and the binding of solubilized VDAC protein to the chip can be measured. This would provide a larger signal because of the greater molecular weight of VDAC relative to erastin. SPR can be preferable for initial studies because it uses less protein than calorimetry, SPR can use protein in the range of 100 µg versus mg quantities for calorimetry.

In another embodiment, isothermal titration calorimetry (ITC) can be used to measure the molar enthalpy ($\Delta H$) and equilibrium binding constant ($K_B$) for the interaction between an agent which induces oxidative cell death, such as for example erastin, and any of the isoforms of the VDAC proteins. Calorimetry is the gold-standard method for measuring binding because it does not suffer from artifacts of surface chemistry that can complicate SPR binding data. From the calorimetry data, the Gibbs free energy of binding ($\Delta G=-RT \ln K_B$) and the entropy of binding ($\Delta S=(\Delta H-\Delta G)/T$) can be calculated, where R is the ideal gas constant and T is the temperature in the experiment[156, 157]. By performing this experiment at multiple temperatures, the change in heat capacity upon binding (at constant pressure), $\Delta C_p$, can be calculated. Thus, these experiments allow characterization of the thermodynamic parameters associated with binding of erastin to each VDAC isoform. As controls, the binding of an agent which induces oxidative cell death, such as for example erastin, to several other proteins can be tested, including glutathione-S-transferase (GST), avidin and bovine serum albumin.

In other embodiments, mutations in VDACs that are predicted to disrupt binding, based on a homology model and docking experiments can be designed. VDAC mutant proteins of any one of the isoforms can be expressed, purified, and tested for their binding to an agent which induces oxidative cell death, such as for example erastin. It is recommended that the concentration of protein in an ITC ligand-binding experiment be at least 10 times the $K_B$ estimate[156]. Given that erastin has a potency of 1 to 5 µM in several tumor cell lines, this is an upper limit on $K_B$. It is desirable to have 20 µM VDAC protein in solution when erastin is added in the ITC experiment to ensure all added erastin is bound to target protein. Given that the sample cell requires 1.4 mL, 28 nmol of each VDAC, or ~1 mg of each VDAC protein are needed for each calorimetry experiment. Thus, about 5 to 10 mg of each VDAC isoform is necessary for this set of experiments. This is achievable given published VDAC expression protocols[152]. For these experiments, erastin can be used as the experimental compound and erastin B1 as a negative control that is not expected to bind to VDAC proteins with high affinity, given its lack of lethality. Microcal Omega Isothermal Titration Calorimeter, which consists of an Omega reaction cell (T115), control module (T106) and nanovoltmeter (059), can be used for these experiments.

In another embodiment, there is provided a method for determining whether there is a change in the fluorescence of any of the VDAC proteins upon incubation with an agent, such as for example erastin. If erastin binds near a hydrophobic residue (Tip, Tyr or Phe), it is possible that the binding would cause a change in the fluorescence of VDAC that would allow us to determine the binding constant for this interaction. This would readily be detected using a fluorescence spectrometer. In another embodiment, a $^3$H-labeled erastin analog can be created and used in a radioligand binding assay. The $^3$H-labeled erastin analog can be created by acetylating erastin A3 with [$^3$H]—CH$_2$COCl. Erastin A3 is the affinity analog used to purify VDAC, and $^3$H-labeled erastin analog can be used in a charcoal precipitation or filter-binding assay.

Measurement of Effect of Erastin on VDAC-Mediated Transport In Vitro:

In certain embodiments, the effect of agent, such as for example erastin, on VDAC-mediated transport in reconstituted liposomes and lipid bilayers can be determined. The flow of ATP through each VDAC isoform determined in the presence of erastin or erastin B1, can be used as a negative control. A method for measuring the flux of ATP through VDAC channels reconstituted into planar phospholipids membranes has been reported[158]. In a certain embodiment of this method, VDAC channels are open at low voltage (<10 mV) and closed at higher voltages. The method involves forming lipid bilayer membranes with a 1% solution of diphytanoylphosphatidyl choline and cholesterol in hexane using a modified Montal-Mueller technique[159]. VDAC proteins in 1% Triton X-100 are added to one side of the planar lipid bilayer; subsequently, a concentrated ATP solution is added to the same (cis) side. Aliquots are removed from the trans side and mixed with a D-luciferin/luciferase solution; light output is determined using a luminometer; the [ATP] on the trans side can be calculated as a function of time using a calibration curve. In certain embodiments, this method can be used to determine whether an agent, such as for example erastin, accelerates or impedes the rate of ATP flux through each VDAC isoform. In certain embodiments, the experiments can be performed as a function of membrane voltage to determine whether erastin increases ATP transport at voltages >10 mV. In certain aspects, the invention provides that erastin, or any other agent that induces oxidative cell death, increases ATP transport at voltages >10 mM. An agent which increases the rate of ATP transport is an agent which induces oxidative cell death.

In other embodiments, the invention provides a method which can measure the effect of an agent, such as for example erastin, on VDAC-mediated transport of NADH across the mitochondrial outer membrane. In a non-limiting example, a mitochondria containing fraction can be isolated from yeast expressing a single, specific VDAC isoform, such as for example human isoforms VDAC1, 2, or 3, or any homologues, or mutant versions thereof, in place of yeast VDAC. Using this mitochondria containing fraction, the rate of NADH oxidation can be measured. In this system, when NADH is added to isolated mitochondria, or a mitochondria containing fraction, NADH is transported across the mitochondrial outer membrane in a VDAC-dependent manner[153]. The rate of transport can be determined by measuring the rate of NADH oxidation by the inner-mitochondrial-membrane-protein NADH dehydrogenase.

Mitochondria with a disrupted outer membrane transport NADH faster than yeast mitochondria containing murine or human VDAC1, VDAC2 or VDAC3, suggesting that VDAC is rate-limiting for NADH transport across the outer mitochondrial membrane. In fact, the rate of transport of NADH through the murine VDAC isoforms is VDAC1>VDAC2>VDAC3. In certain embodiments, this method can measure the effect of an agent, such as for example erastin, on the rate of NADH transport across the outer mitochondrial membrane in mitochondria, expressing human VDAC isoforms, isolated from yeast. In other embodiments, this method can be used to identify an agent which induces oxidative death. An agent which increases the rate of NADH transport, is an agent which induces oxidative cell death. A non-limiting example of such an agent is erastin.

In other embodiments, cellular fractions containing mitochondria can be isolated from human cells, including but not limited to any of the tumor cell lines as described herein. In certain aspects the invention provides, that erastin causes increased flux through the outer mitochondrial membrane when VDAC3 is present. In certain embodiments, the invention provides that erastin causes increased flux through the outer mitochondrial membrane when human VDAC1, 2 or 3 is expressed in yeast. In other embodiments, expression levels of VDAC1, 2 or 3 in yeast, can be modulated to determine the effect of VDAC protein levels on the rate of NADH transport, in the presence or absence of erastin.

In other embodiments, a method can measure the effect of an agent, such as for example erastin, on the rate of NADH transport across the outer mitochondrial membrane in mitochondria isolated from any suitable tumor cell line, such as for example HT1080 cells, which express only VDAC1, VDAC2 or VDAC3. These cell lines can be created by stably transfecting, e.g., HT1080 cells with a cDNA vector containing a specific VDAC isoform and shRNA vectors targeting the other VDAC isoforms. cDNA expression constructs for human VDACs can be created. shRNA constructs can be created in a lentiviral backbone[160] (pLKO.1) targeting VDAC1 (five constructs), VDAC2 (five constructs) and VDAC3 (five constructs). In a non-limiting example, the ability to down regulate VDAC expression of at least one construct for each isoform was demonstrated. The isoform-specific pattern of expression can be determined using qPCR and 2-D gels. Once cell lines which express only specific VDAC isoforms are obtained, mitochondria containing fractions can be isolated, and the rate of NADH oxidation in intact mitochondria versus mitochondria with a disrupted outer membrane[153] can be measured. In certain embodiments, measurements of the rate of NADH oxidation can be done to determine the effect of an agent, such as for example erastin, on this rate of NADH uptake. In another embodiment, this method determines which VDAC isoform participates in NADH transport.

In other embodiments, the invention provides a method to measure the effect of erastin on sucrose uptake by each human VDAC isoform in reconstituted liposomes[89, 150]. In this method, VDAC protein is reconstituted in liposomes using a sonic freeze-thaw method. Sucrose import is determined by measuring liposomal swelling in the presence of 50 mM sucrose; swelling is in turn measured by the amount of light scatter at 520 nm. Sucrose import can also be determined by measuring [$^{14}$C]-sucrose uptake[89, 150]. The above described functional assays, are non-limiting examples of assays that can be used to determine whether an agent, such as for example erastin, effects functional properties of VDAC channels and whether there is isoform-specificity to any such effect.

Photocrosslinking of Erastin to VDAC Isoforms:

In certain aspects, the invention provides methods to determine how an agent, such as for example erastin, alters the functions of VDAC proteins. In certain embodiments, erastin A3 can be coupled to a benzophenone-containing moiety to allow for photocrosslinking of erastin to each VDAC isoform. In a non-limiting example for synthesis and use of these photolabeled compounds, each VDAC isoform can be incubated with an erastin-benzophenone photo-reactive probe and inactive control probe in parallel, placed in optical glass cells (Starna, cat#1-SOG-10-GL14-S), purged with argon gas for 5 min and irradiated at 350 nm for 5-15 min in a Rayonet Reactor. After irradiation, the protein-erastin complex can be digested with several different proteases and the resulting sample submitted for ES/LC-MS-MS analysis to identify peptide residues modified by this photolabel. There are multiple routes through which it will be possible to use MS analysis to determine the site at which erastin is cross-linked to each VDAC isoform.

Figure 17:
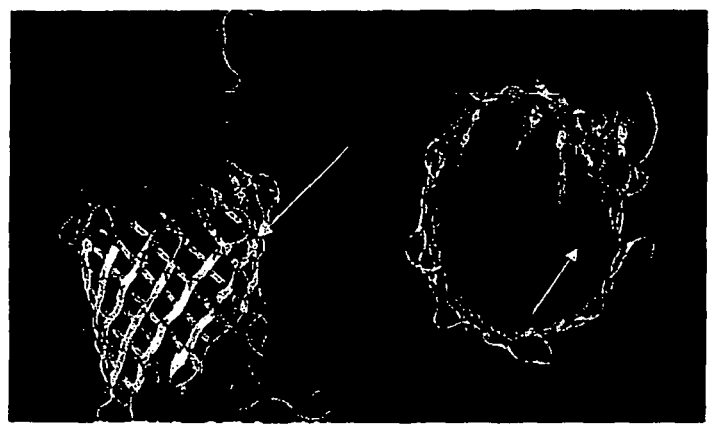
FIG. 17 shows a homology model of VDAC1, bound to erastin. The left panel shows a side view of the pore, while the right panel shows a top-down view. Predicted beta strands (yellow) and alpha helices (red). White arrow is pointed at erastin which is docked in a binding site at the base of the alpha helix. Docking and rendering performed with Molecular Operating Environment (Chemical Computing Group). Coordinates: FEBS Lett. 2002, 5; 520(1-3):1-7.
Figure 18:
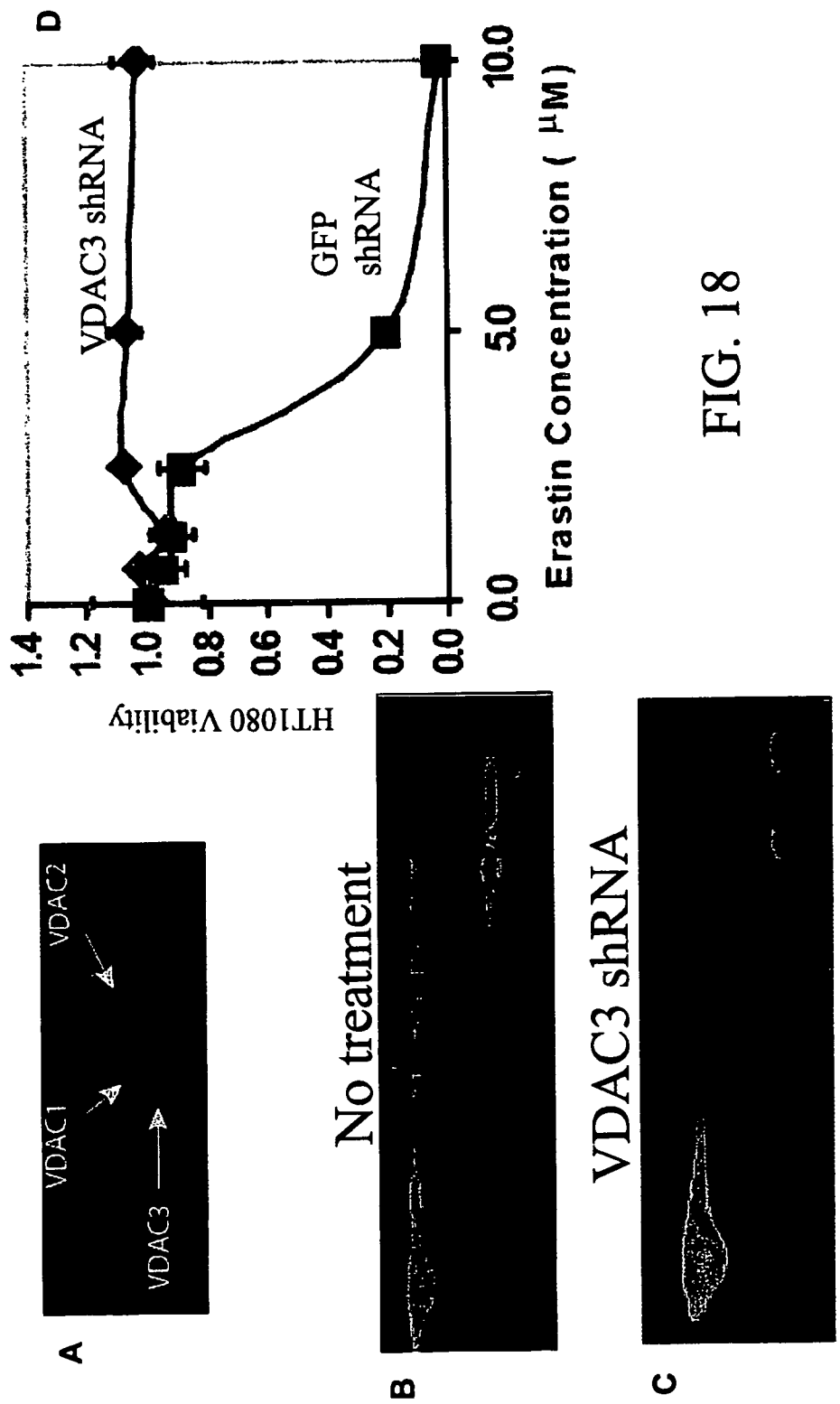
FIG. 18 shows that VDAC3 knockdown causes resistance to erastin. HT1080 fibrosarcoma cells were infected with shRNA targeting VDAC3 and sensitivity to erastin was measured using Trypan Blue exclusion. shRNA to GFP was used as a control (panel A). Knockdown of VDAC3 was confirmed at the protein level by 2D gel and western blot with a pan-VDAC antibody (panels B-D).
Figure 19:
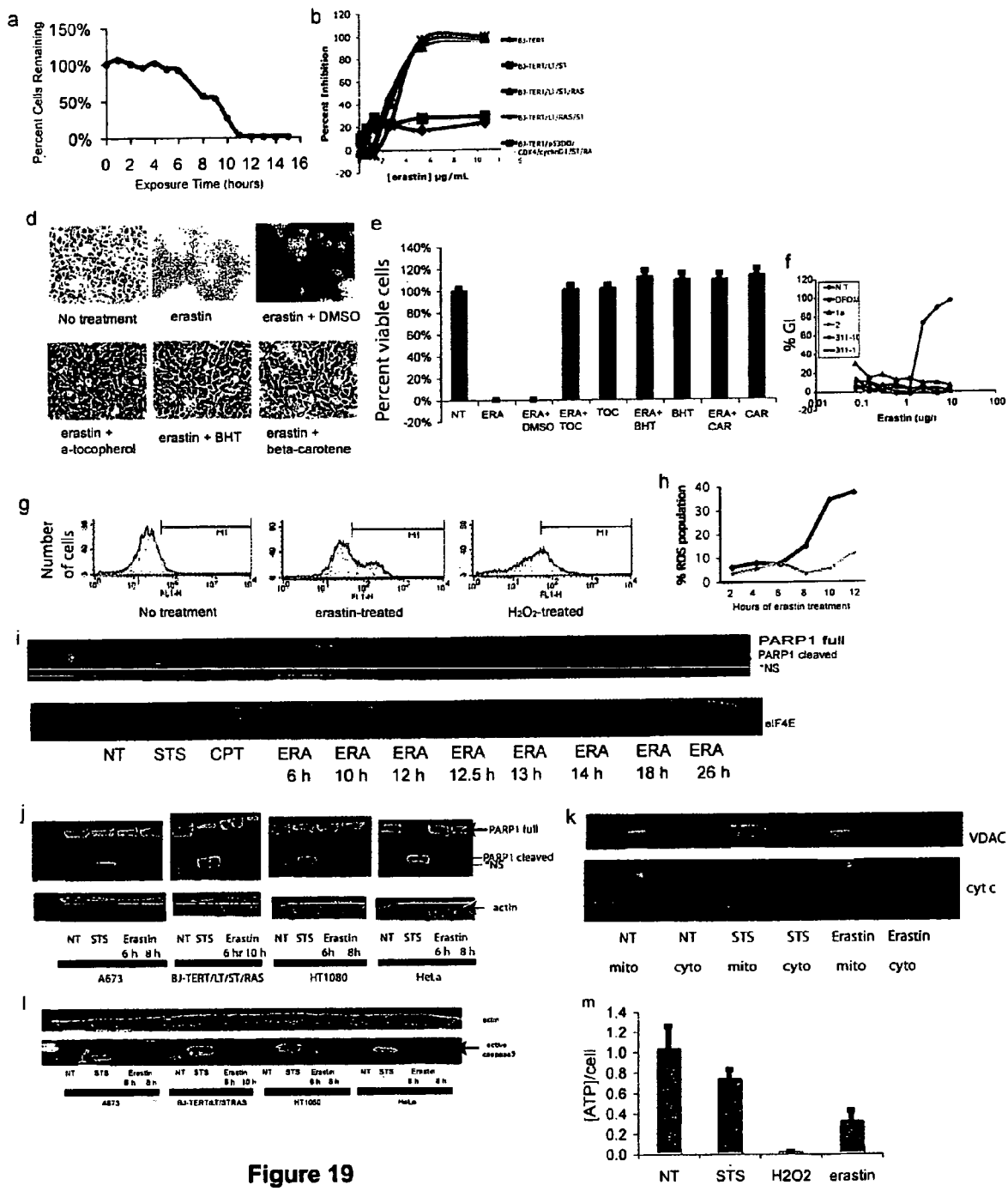
FIG. 19 (panels a-m) shows that erastin activates a rapid, oxidative, non-apoptotic cell death process. (a) BJ-TERT/LT/ST/RAS$^{V12}$ cells were treated with 9 µM erastin A1 for the indicated length of time, and the number of viable cells determined. (b) 1,000 BJ-TERT/LT/ST/RAS$^{V12}$ cells/well in 384-well plates were treated with erastin for 2 d, then alamar blue was added to a final concentration of 10% and the plates were incubated for 16 h. Red fluorescence resulting from reduction of alamar blue was detected on a Victor3 platereader. The percent growth inhibition is shown; error bars represent one SD. Three different $RAS^{V12}$-expressing cell lines were used, and all were found to be sensitive to erastin, whereas two isogenic lines lacking $RAS^{V12}$ were resistant to erastin. (c) TEM images (20,000× magnification) of BJ-TERT/LT/ST/$RAS^{V12}$ mitochondria after cells were treated with nothing, erastin (37 µM for 10 h) or staurosporine (STS, 1 µM for 5 h), and phase-contrast photograph of BJ-TERT/LT/ST/$RAS^{V12}$ cells 24 h after 9 µM erastin A1 treatment is also shown to indicate that even after cell death, nuclei are intact. (d) Antioxidants suppress erastin-induced death. BJ-TERT/LT/ST/$RAS^{V12}$ cells were treated as indicated and photographed. (e) The number of viable cells was quantified under each condition using a hemacytometer. (f) Iron chelators suppress erastin-induced cell death. Cells were seeded in 384-well plates (6,000 cells/well) and treated with 2-fold dilution series of erastin in the presence of 100 µM desferrioxamine mesylate (DFOM), 100 µM of iron chelator 1a, 100 µM of iron chelator 2, 10 µM or 1 µM of iron chelator 311. After 24 h, alamar blue was added and cell viability assayed. (g, h) Erastin-induced formation of oxidative species. BJ-TERT/LT/ST/$RAS^{V12}$ (shown in histogram plots, and in line graph as dark diamonds) or BJ-TERT cells (shown in line graph only, light circles) were treated with 4.6-µM erastin A1 and the level of intracellular oxidative species determined. (i, j) STS, but not erastin, induces PARP1 cleavage (red bands at top) in BJ-TERT/LT/ST/$RAS^{V12}$ cells and in A673, HT1080 and HeLa cells. NS: non-specific band. (k) Cytochrome c is released from mitochondria in response to STS, but not erastin in BJ-TERT/LT/ST/$RAS^{V12}$ cells. Cells were treated with STS or erastin, separated into mitochondrial and cytosolic fractions, and probed for cytochrome c (lower red band) and total VDAC (middle green band, pan-VDAC antibody). (l) Caspase-3 is not cleaved in response to erastin. Cells were treated as indicated and probed with an anti-caspase-3 antibody that recognizes both the full length and the cleaved, active form (lower band). (m) ATP levels are decreased modestly upon erastin treatment. ATP levels were measured, viable cells determined by Trypan Blue exclusion and ATP per viable cell determined. Abbreviations: DMSO, dimethylsulfoxide; BHT, butylated hydroxytoluene; TOC, alpha-tocopherol; ERA, erastin A1; CAR, beta-carotene; STS, staurosprine.
Figure 20:
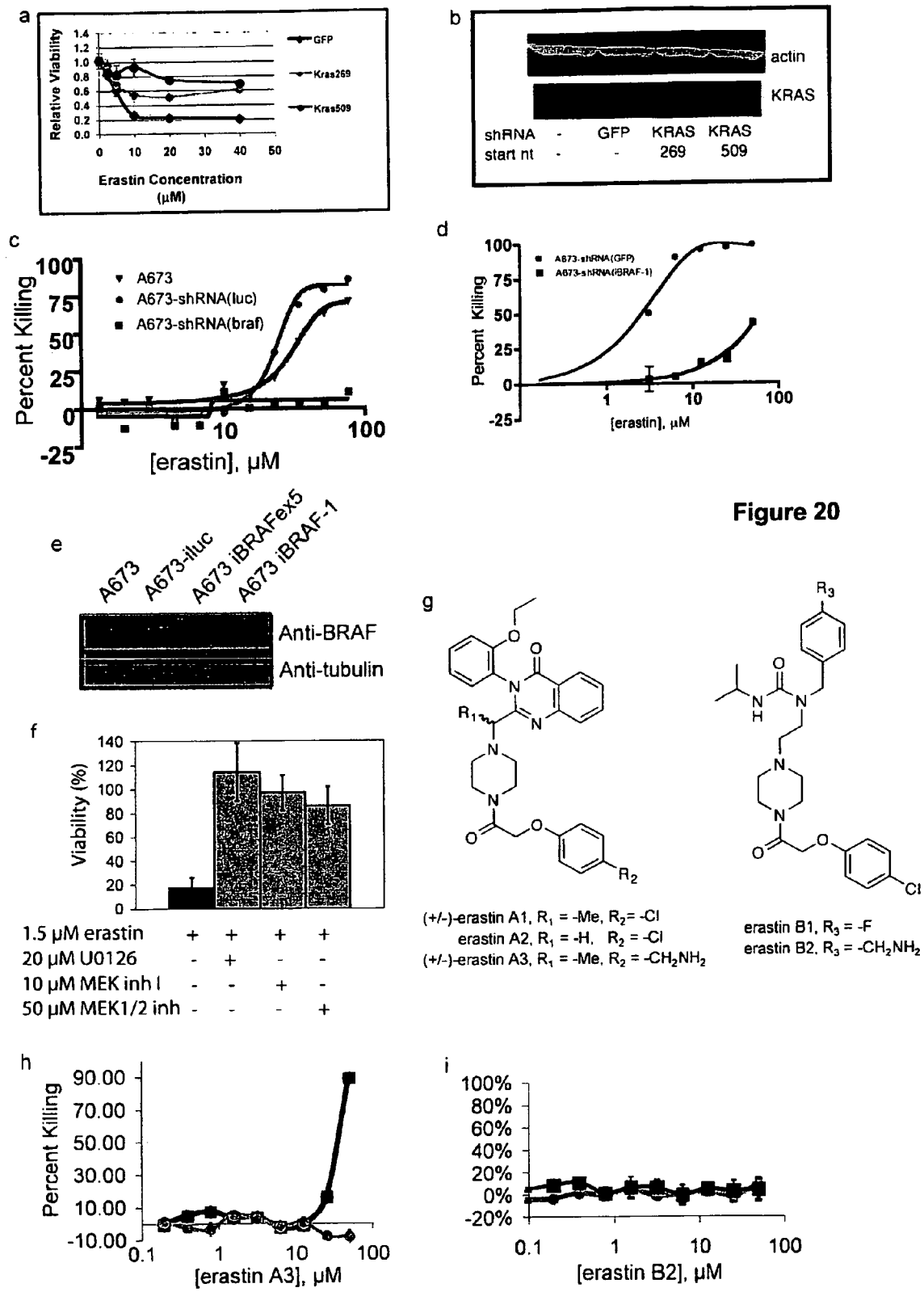
FIG. 20 (panels a-n) shows that erastin lethality is dependent on the RAS/RAF/MEK pathway. (a) Calu-1 lung carcinoma cells harboring oncogenic KRAS were infected with lentivirus containing shRNAs targeting KRAS or GFP. Sequences of shRNAs are indicated by starting nucleotide (nt) in the KRAS mRNA coding sequence. Cells were treated with erastin and viability measured by Trypan Blue exclusion. (b) Knockdown of KRAS was confirmed by western blot. (c,d) A673 cells harboring oncogenic BRAF were infected with lentiviral shRNAs targeting BRAF exon 5 (c) or the 5' UTR (d), luciferase (LUC)(c) or GFP (d). Cells were treated with erastin and viability measured using Alamar Blue (c) and Trypan Blue (d). (e) Knockdown of BRAF was confirmed by western blot. (f) MEK inhibitors prevent erastin lethality. BJ-TERT/LT/ST/$RAS^{V12}$ cells were treated with erastin alone or in with a MEK inhibitor U0126 (20 µM), MEK inhibitor I (10 µM) or MEK 1/2 inhibitor (50 µM). After 48 h, viability was determined using Trypan Blue. (g) Structures of erastin and related analogs. (h) and (i) Dose-response curves were measured for erastin A3 and erastin B2 in BJ-TERT/LT/ST/$RAS^{V12}$ cells (black squares) or BJ-TERT cells (grey circles). (j) Calu-1 lung carcinoma cells harboring oncogenic KRAS were infected with lentivirus containing shRNAs targeting KRAS or GFP. Sequences of shRNAs are indicated by starting nucleotide (nt) in the KRAS mRNA coding sequence. Cells were treated with erastin and viability (y-axis) measured by Trypan Blue exclusion. Cells were treated with erastin for 24 hours, and percent inhibition of viability (y-axis) measured using Alamar Blue (k) and Trypan Blue (l). (m) Structures of erastin and related analogs. (n) Dose-response curves were measured for erastin A6, erastin B2, erastin A8 and erastin A9 in BJ-TERT/LT/ST/$RAS^{V12}$ cells (squares) or BJ-TERT cells (circles) using Alamar Blue.
Figure 21:
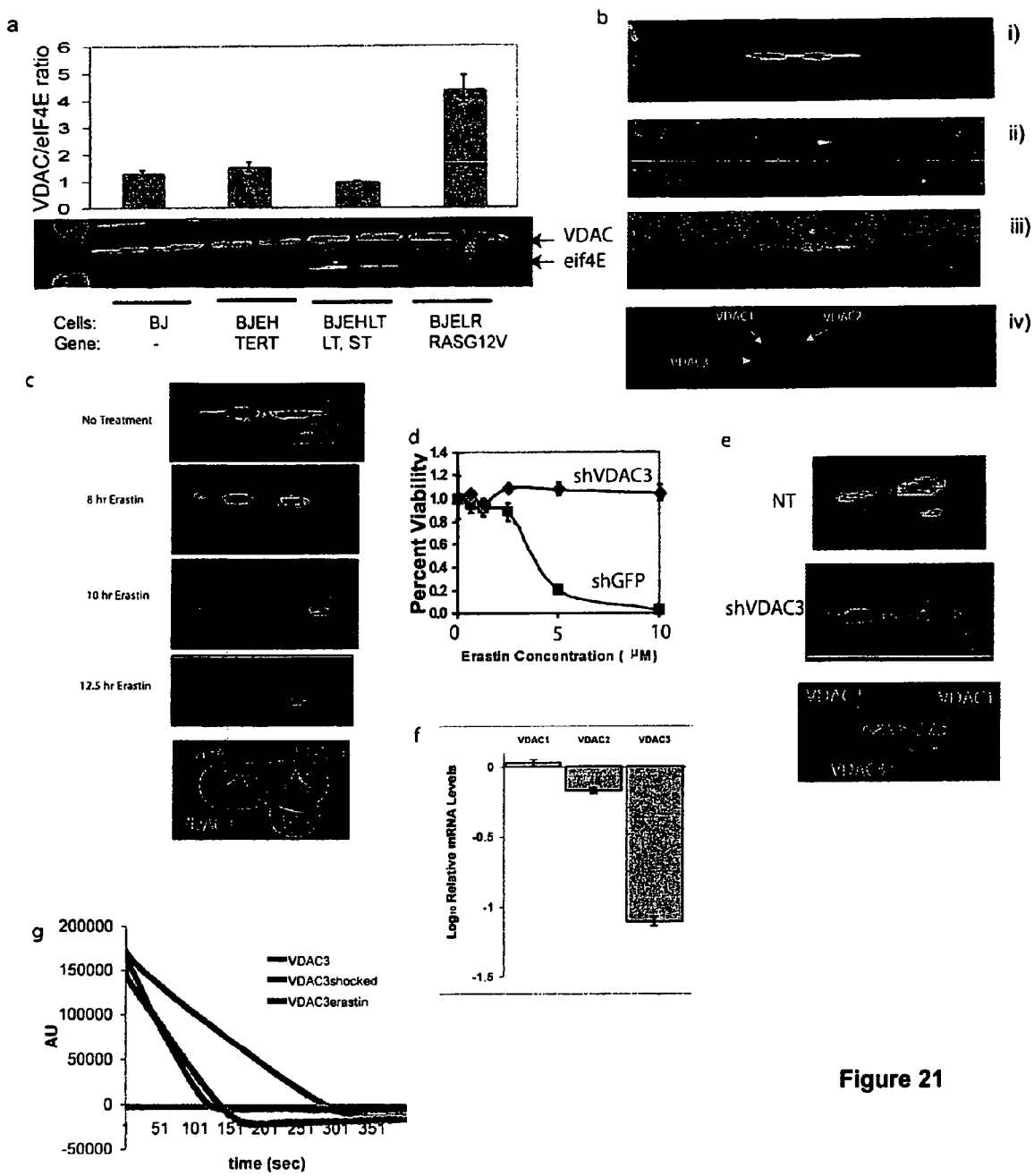
FIG. 21 (panels a-k) shows that erastin acts through VDACs. (a) Quantitative western blot of VDAC/eif4E protein ratio in engineered BJ-derived cells. (b) Identification of VDAC isoforms in BJ-TERT/LT/ST/$RAS^{V12}$ cells using 2-D electrophoresis. i) VDAC1, VDAC2 and VDAC3 were detected by a rabbit polyclonal VDAC antibody (Abcam/ab3434), ii) VDAC1 was detected by a mouse monoclonal VDAC1 antibody (Calbiochem/529534), iii) VDAC2 was detected by a goat polyclonal VDAC2 antibody (Abcam/ab22170), iv) An illustration of 3 isoforms of VDAC separated by the 2-D gel electrophoresis. (c) BJ-TERT/LT/ST/RASV12 cells were treated with erastin for the indicated time and levels of each VDAC isoform determined by quantitative 2D western. (d,e) Infection with VDAC3 shRNA protects erastin-treated cells. 293T cells were transfected with shRNA-plasmid construct using FuGene and viral supernatant transferred to HT1080 cells, and treated with erastin dilutions and viability measured using Trypan Blue exclusion. Knockdown was confirmed using 2D gels to detect the 3 VDAC isoforms. VDAC3 shRNAs (V3.B1) or a control construct (shGFP) was used. (f) Quantitative RT-PCR measurements of mRNA levels of the 3 VDAC isoforms after infection with shVDAC3. Knockdown was determined by normalizing to the levels in the shGFP-infected control. Relative expression level is shown. Error bars represent one SD. (g) Mitochondria were purified from yeast expressing murine VDAC3 in place of yeast VDAC, and the rate of NADH uptake determined in the presence or absence of erastin, or in shocked mitochondria in which the outer membrane was disrupted. (h) HT1080 cells were infected with virus expressing either VDAC3-targeted shRNA-plasmid construct (shVDAC3) or VDAC2-targeted shRNA plasmid (shVDAC2), and knockdown of each VDAC isoform was confirmed using 2-D protein gels. (i) These cells were then treated with erastin dilutions, and viability relative to no treatment (y-axis) was determined using Trypan Blue exclusion and compared to an identical process using a GFP control plasmid. Infection with shVDAC2 protects cells from erastin-induced death. mRNA levels of the three VDAC isoforms after infection with shVDAC2-expressing virus were measured using quantitative RT-PCR. (j) Mitochondria were purified from porin-knockout yeast expressing murine VDAC2, and the rate of NADH oxidation determined in the presence of erastin or an inactive analog, erastin A8 (triangles). Y-axis shows relative rate of NADH oxidation, as normalized to no treatment. (k) VDAC2 binding assays using tritium-labeled erastin A9 in competition with unlabeled erastin A9 (squares) or erastin A8 (triangles) reveals that active analog erastin A9, unlike the inactive erastin A8, directly binds VDAC2.
Figure 22:
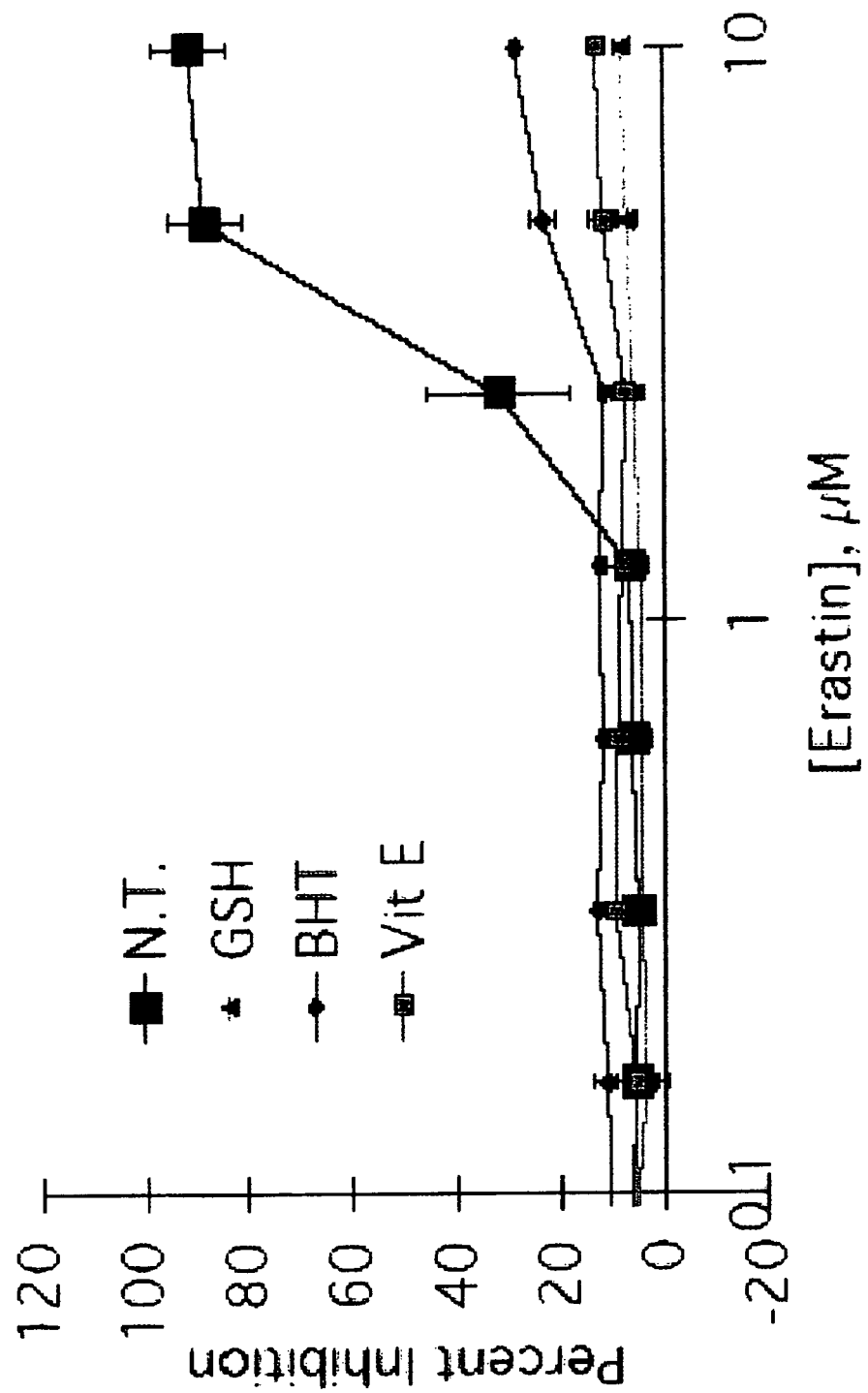
FIG. 22 shows that erastin induced death in HT1080 fibrosarcoma cells is suppressed by anti-oxidants.
Figure 23:
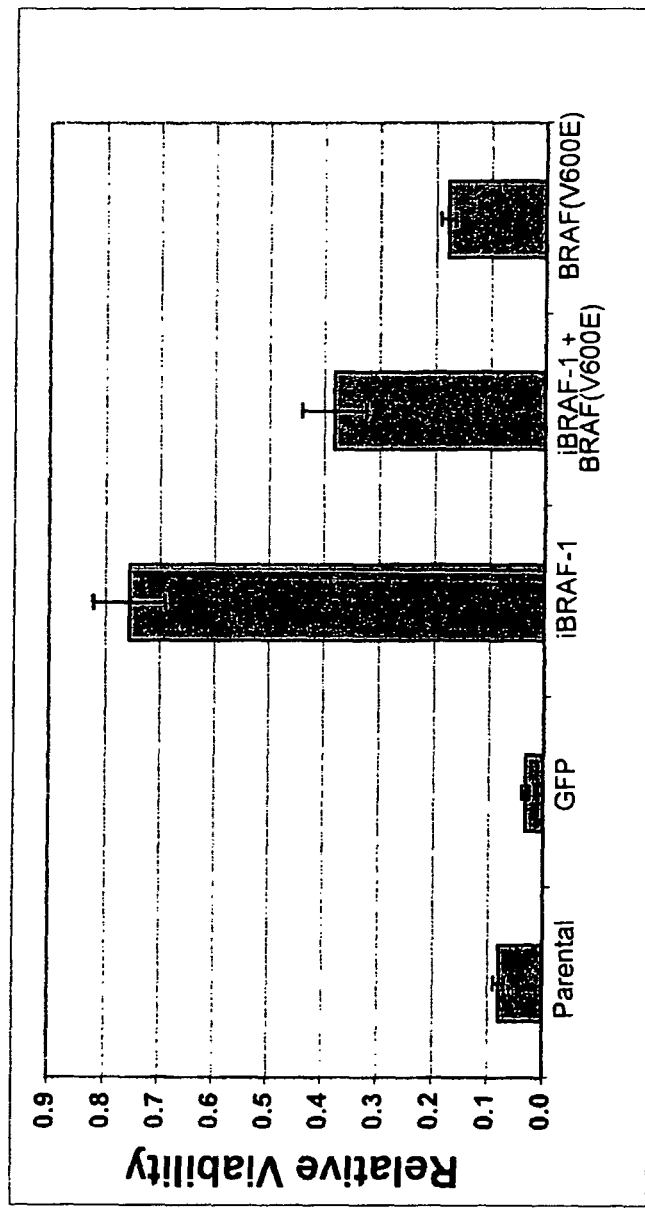
FIG. 23 shows that knockdown of BRAF by shRNA causes resistance to erastin. Co-expression of a non-targetable V600E mutant BRAF restorers sensitivity to erastin.
Figure 24:
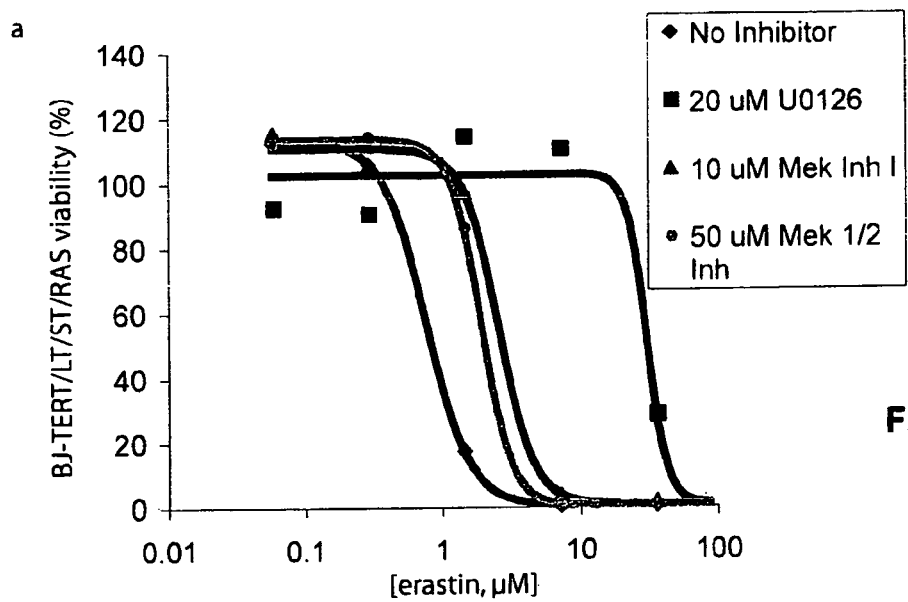
FIG. 24 shows that inhibitors of MEK Protect Viability of Erastin-Treated BJELR and HT1080 cells. Cells grown in 175 cm$^2$ flasks were reseeded in 6-well format (1.4×10$^5$ cells/ well) and treated with erastin dilutions (5-fold, from 36 uM to 60 nM, with no-drug control, n=2) in the presence of one of the MEK inhibitors U0126 (20 uM), MEK inhibitor I (10 uM), MEK 1/2 inhibitor (50 uM), PD98059 (50 uM), MEK inhibitor II (30 uM), or in the absence of inhibitor. After 48 hours, cells were trypsinized and counted using a Vi-CELL™ Series Cell Viability Analyzer. Panels (a) and (b) show the dose-response curves obtained with BJELR and HT1080 cells, respectively, with U0126, MEK inhibitor I, or MEK 1/2 inhibitor, or in the absence of inhibitor. Non-linear regression was used to fit curves to the data points using GraphPad Prism™ software. The bottom of each curve was set to zero. P-values based on comparison between the values fit for the top, logEC50, and the hill slope for the inhibitors versus no inhibitor were less than 0.0001 for all curves shown. Panel (c) shows the $IC_{50}$ values in uM from the best fit curve of each inhibitor used. It also gives the fold-change in $IC_{50}$ produced by each inhibitor and the p-value obtained when comparing the curves based only on the $logEC_{50}$ value.
Figure 24:
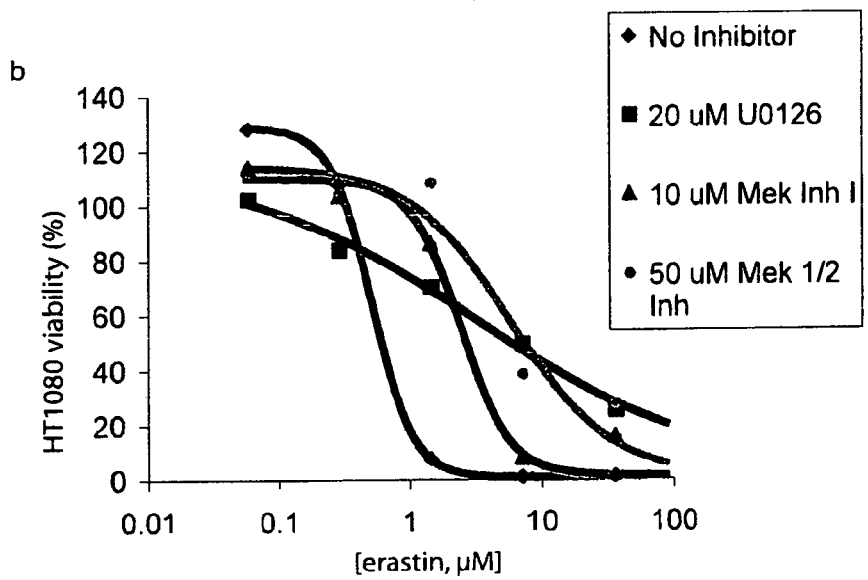

Creating and Testing Erastin-Binding-Defective VDAC Mutants:

In certain aspects, the invention provides methods to generate VDAC mutants, which are defective in erastin binding. VDAC homology modeling and erastin in silico docking results as demonstrated in FIG. 17 can be used to create VDAC mutants that are functional, but that fail to bind to erastin. In certain embodiments, mutations can be introduced in the amino-terminal helical region of any one of the VDAC isoforms, such as for example VDAC3 and the hinge region between the helix and the barrel because these sites would be logical erastin binding sites, given that the amino terminus negatively regulates conductance and that erastin acts via a gain of function which may involve locking the channel in an open conformation.

In certain embodiments, mutations can be created by overlap extension PCR, cloning of the cDNA into pcDNA3(zeo) and sequencing of the clone. To test the effect of each mutation, a stable cell line derived from HT1080 cells can be created by transfecting and selecting zeocin. Subsequently, a lentivirus can be used to knock down expression of any one of the VDAC isoforms, including VDAC3, and selection accomplished with puromycin to retain only knockdown cells. Viral titer and volume can be adjusted as needed to confer >90% knockdown of these VDAC isoforms. Thus, cells can express any one of the mutant VDAC isoforms, including but not limited to VDAC3 mutants, from the pcDNA3(zeo) vector. This expression can be confirmed by qPCR and 2D gel. Erastin sensitivity and cell viability can be measured by an automated Trypan Blue exclusion assay on a Vi-Cell, for each such cell line, to identify VDAC mutants that cause erastin resistance. For mutants that cause erastin resistance, the cDNA can be cloned into a bacterial expression vector, and the mutant protein can be expressed and purified, as described above, for the wild-type VDAC proteins. Once each mutant is purified, erastin binding can be measured by SPR and calorimetry, as described above. An assay can measure the effect of erastin on these mutants using lipid bilayers to confirm a lack of gating by erastin. Such characterization of erastin binding to VDAC demonstrates that binding of erastin to VDACs is necessary for erastin's lethality.

Hypothesis Connecting Oncogenic-RAS Signaling and Erastin Sensitivity:

In certain aspects, the invention provides that oncogenic-RAS-expressing cells are more sensitive to erastin because of two effects, both caused by the RAS-RAF-MEK pathway. In one aspect, Ras-expressing cells are more sensitive to erastin because of increased VDAC abundance. In another embodiment, Ras-expressing cells are more sensitive to erastin because they may have a need for a greater fraction of closed VDAC channels. The increased VDAC abundance may be due to increased transcription and/or translation of VDAC or decreased VDAC turnover. The increased VDAC closure in RAS-expressing cells may be due to increased glycolytic activity in RAS-expressing cells that leads to (i) increased NADH abundance and (ii) increased activity of the electron transport chain, driving down the local pH in the mitochondrial inter-membrane space. Increased NADH abundance would lead to VDAC closure, as NADH causes VDAC closure in vitro and in isolated mitochondria[161, 162]. Low pH would likely lead to VDAC closure in vivo, given that VDAC closure occurs in low pH environments in vitro[67]. Increased electron transport chain activity would therefore lead to greater VDAC closure in vivo[163]. The overall effect of these two factors would be to increase the pool of closed VDAC channels in cells with activated RAS-RAF-MEK signaling.

Erastin-induced locking of VDACs in an open conformation in cells with increased levels of VDAC, including but not limited to oncogenic-RAS-expressing cells, would lead to excess electrogenic activity of the electron transport chain, leakage of electrons to dioxygen with concomitant production of hydrogen peroxide, which encounters pools of free iron that in turn leads to Fenton chemistry and catalytic production of reactive hydroxyl radicals. Thus, VDAC proteins serve to homeostatically regulate activity of the electron transport chain, and dysregulation of this function leads to oxidative death due to excess production of oxidative species.

Measure VDAC mRNA and Protein Levels with and without RAS, RAF and MEK Signaling:

To determine whether the RAS-RAF-MEK pathway leads to an increase in VDAC proteins without changing VDAC mRNA levels, VDAC I, VDAC2 and VDAC3 mRNA and protein levels can be measured using any suitable method including but not limited to quantitative RT-PCR (qPCR) and 2D gels. Probe-primer pairs were developed to measure all 3 VDAC mRNAs relative to an internal standard. The primers used in this method amplify all three isoforms and the internal control equally and are equally sensitive to changes in the input mRNA concentration. In certain embodiments, this method confirmed isoform-specific mRNA knockdown in engineered BJ cells and HT1080 cells. In other aspects, the invention provides a method to measure all 3 VDAC isoforms using 2D gels.

Figure 9:
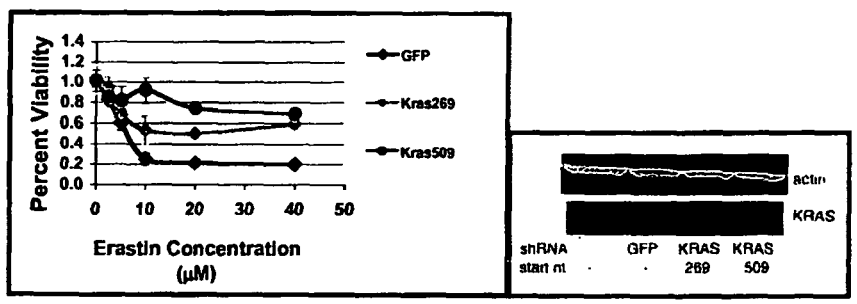
FIG. 9 shows that knockdown of KRAS in Calu-1 lung cancer cells causes resistance to erastin. (Left panel) Calu-1 cells that had been infected with lentiviruses expressing shRNAs targeting GFP (as a control) or KRAS (targeting 19 nucleotides starting at nucleotide 269 or 509) were seeded in 6-well plates, treated with erastin and viability measured using Trypan Blue exclusion on a Beckman Vi-Cell. Error bars represent one SD. (Right panel) Western blot showing KRAS knockdown in Calu-1 cells. Top band=actin, Bottom band=KRAS. Calu-1 cells were infected with nothing (left lane), or lentiviruses containing shRNA constructs targeting GFP or KRAS. For KRAS, the shRNA was designed to match 19 nucleotides starting at the indicated nt.

To test the effect of oncogenic KRAS and NRAS on VDAC mRNA and protein levels, VDAC mRNAs can be measured using qPCR in any cell line of interest, such as for example Calu-1 cells, which have mutant KRAS, and HT1080 cells, which have mutant NRAS, and in isogenic cells in which KRAS or NRAS, respectively, can be knocked down using a lentiviral shRNA. pLKO.1 lentiviral shRNA constructs targeting KRAS and NRAS were created. Two KRAS-targeted constructs effectively knock down KRAS (FIG. 9). These constructs can be transfected along with a vector expressing the coat protein VSVG (pMD.G) and a packaging vector (pCMVdR.89) into 293T cells using Fugene. Supernatant at 48 hours is collected and added to the target cell lines (i.e. Calu-1 or HT1080). This protocol was used to knock down each VDAC isoform using the pLKO.1 vector in HT1080 cells, BRAF in A673 cells and KRAS in Calu-1 cells. The effect of knockdown on each VDAC mRNA can be measured using qPCR, as well as KRAS and NRAS to confirm knockdown. In addition, protein lysates can be made, and run on 2D gels, detecting the three VDAC isoforms with a pan-VDAC antibody. The amount of each isoform can be quantitated relative to actin on the same gel using a LICOR Odyssey infrared scanner. As an additional control, a silent KRAS or NRAS mutant that is resistant to each of the effective shRNAs can be generated, and used to determine whether this resistant cDNA can reverse the effect of the shRNA. This will be a confirmation that the shRNA is acting through the intended target (i.e. KRAS or NRAS). Similar experiments can be performed for BRAF. Overall, these experiments will determine the effect of HRAS, KRAS and NRAS signaling on VDAC mRNA and protein levels.

To test the effect of BRAF signaling, VDAC mRNA and protein levels (using pPCR and 2D gels, as described above) can be measured in A673 cells (with an activated (V599E) mutant BRAF), and in isogenic cells in which BRAF is knocked down using a viral shRNA construct. As additional controls, the effects of at least five additional shRNA constructs targeting BRAF can be tested, wherein the effects of each of these shRNA constructs can be tested also in the presence of a BRAF cDNA containing a silent mutation that renders it resistant to each shRNA, and an shRNA construct targeting luciferase. Five additional lentiviral shRNA constructs targeting BRAF were obtained, and two of them demonstrated knock down of BRAF at the protein and mRNA level. These experiments can determine the oncogenic BRAF signaling on any of the VDAC isoform mRNA or protein levels.

To test the effect of MEK1/2 signaling on VDAC mRNA levels, VDAC mRNA and protein levels can be measured by any suitable method, including but not limited to qPCR and 2D gels, in four cell lines (FIG. 12, HT1080, A673, Calu-1 and BJ-TERT/LT/ST/RAS$^{V12}$) that have been treated with each of three structurally different MEK1/2 inhibitors. Non-limiting examples of MEK1/2 inhibitors are provided in FIG. 31. These experiments can determine whether MEK signaling affects mRNA or protein levels of any of the VDAC isoforms. An effect of MEK inhibitors on VDAC protein or mRNA levels, can be confirmed and the specific MEK isoform responsible for this effect can be determined by obtaining or creating shRNA constructs targeting MEK1 and MEK2 specifically. MEK1 and MEK2 function can be knocked down by similar protocols and control experiments as described for RAS and RAF knockdowns.

Knockdown experiments can be controlled to ensure that shRNA induce knockdown of the desired target (KRAS, NRAS, BRAF or MEK1/2) at the mRNA and protein levels, and that related isoforms are not affected (i.e. including HRAS, CRAF and ARAF). MEK inhibitors should block MEK1/2 phosphorylation of ERK1/2 substrates, and this can be confirmed by western blot with a phospho-specific ERK1/2 antibody. These experiments can determine the role of RAS, RAF and MEK signaling (and specific family members) in modulating mRNA and protein levels of each VDAC isoform.

Methods to Measure the Ratio of Open and Closed VDAC in Cells with and without RAS, RAF and MEK signaling:

In certain aspects, the invention provides a fluorescently labeled VDAC reporter construct of any one of the VDAC isoforms. In certain embodiments, the reporter construct is labeled with YFP, CFP, RFP, any of the (Fluorescent Protein) FP optimized variants, or any other suitable fluorescent label. In certain embodiment, reporter constructs are fully functional and active in vivo and in vitro, as measured by any suitable assay which determines VDAC protein function. Methods and protocols for creating fluorescent reporter proteins are well known in the art. The FP can be fused to a VDAC isoform at any position in the VDAC protein, so long that the fluorescent VDAC reporter remains functional. The FP can be fused to the VDAC isoform with or without a protein linker sequence. In certain embodiments, a VDAC reporter construct comprises at least one FP. In other embodiments, a VDAC reporter comprises two fluorescent proteins. The two FP can be identical or different. In certain embodiments, the FP is fused to the N-terminus. In other embodiments, the FP is fused to the C-terminus.

In certain embodiments, fluorescently labeled VDAC proteins can be used to monitor expression and localization of VDAC isoforms. In other embodiments, fluorescently labeled VDAC proteins can be used in assays to determine the effect of agents, including but not limited to erastin, on the expression, and/or stability of VDAC isoforms. Treatment with erastin induces disappearance of VDAC2 and 3 isoforms, as determined by Western and 2D-gel electrophoresis, indicating that an agent such as erastin, which induces oxidative cell death, leads to disappearance of its protein target. In certain aspects, the invention provides a method for identifying agents which induce oxidative cell death. In certain embodiments, the method comprises, contacting cells or mitochondrial cell fractions from cell with an agent, determining cell viability and determining whether VDAC protein levels remain unchanged or become reduced in response to treatment with the agent. In other embodiments, the method comprises, contacting cells or mitochondrial cell fractions from cell, which express a fluorescently labeled VDAC isoform, with an agent, determining cell viability and determining whether VDAC protein levels remain unchanged or become reduced in response to treatment with the agent Contacting can be done in the presence or absence of a second agent, wherein the agent inhibits formation of oxidative species in mitochondria, or the agent is an iron chelator, or the agent is an antioxidant.

In certain embodiments, determining whether VDAC protein is reduced can be done by measuring the fluorescent signal due to the fluorescently labeled VDAC isoform. In other embodiments, determining whether VDAC protein is reduced can be done by any suitable method known in the art, including but not limited to Western blotting, or 2D-gel electrophoresis. An agent which leads to loss of cell viability, and decrease in VDAC protein level, and/or the fluorescent signal due to a VDAC reporter is indicative of an agent which induces oxidative cell death.

In certain aspects, the invention provides a method to measure the ratio of open to closed VDAC proteins. In certain aspects, the invention provides a fluorescent reporter construct that exhibits conformation-dependent fluorescence that can be used to determine whether a VDAC channel is in an open or closed conformation. VDAC reporter constructs can be created in which yellow fluorescent protein (YFP) and cyan fluorescent protein (CFP) are fused to two different positions of VDAC, such that they create conformation-dependent fluorescent sensors. CFP and YFP containing fluorescent proteins have been used to create conformation-dependent fluorescent sensors[164]. When CFP and YFP come into close proximity, they engage in fluorescence resonance energy transfer (FRET), which can be detected by a change in the fluorescence spectrum of the fusion reporter protein.

Sites within VDAC can be chosen to incorporate CFP and YFP, wherein the sites are chosen based on current models for sites that exhibit a conformational change upon opening. For example, the amino terminal helix of VDAC has been implicated genetically as a negative regulator of channel permeability. One model for VDAC function posits that this amino terminal loop sterically occludes the face of the channel when it is closed[163, 165]. A second model involves movement of several strands of the beta barrel out and up to the surface of the lipid bilayer[166, 167]. CFP can be fused to the VDAC amino terminus and YFP to different positions at the entrance of the beta barrel or on the C terminus, to create a construct in which CFP is brought into proximity with YFP when the channel closes. Thus, by creating a number of different CFP and YFP bearing constructs, such as for example about 10-20 constructs, based on these two classes of models, CFP-VDAC-YFP reporter construct(s) that display(s) a change in fluorescence upon opening and closing can be identified.

In certain embodiments, the CFP-VDAC-YFP reporter construct can be examined for fluorescence changes when the CFP-VDAC-YFP reporter is in lipid bilayers. In other embodiments, the fluorescence changes can be measured when the voltage dependent opening and closing of the VDAC channel is determined. The lipid bilayer setup is similar to the set up, which measures the flux of ATP through VDAC channels using a luciferase/luciferin solution on the trans side of the bilayer. These in vitro experiments can identify a construct that exhibits voltage-dependent opening and closing of the VDAC channel as measured by the changes in fluorescence emission of the fluorescent reporter. Such voltage dependent constructs can be created for all three isoforms (VDAC1, 2 and 3), enabling determination of the ratio of open/closed channel for each VDAC isoform. In certain embodiments, such CFP-VDAC-YFP reporter constructs can be used to identify agents which increase the probability that the VDAC channel is in an open conformation, as measured by a decreased or absent FRET signal. A non-limiting example of such an agent is erastin.

To test CFP-VDAC-YFP reporter constructs in cells, constructs can be cloned in the pLKO.1 lentiviral vector we have used previously to deliver shRNAs. The construct can be co-transfected into 293T cells along with a vector expressing the coat protein VSVG (pMD.G) and a packaging vector (pCMVdR.89), as described above and virus-containing supernatant harvested and transferred onto target cells. Specifically, these constructs can be tested for RAS-pathway-dependent closing using the series of cells, including various knockdown cell lines, described above. To determine the effect of RAS signaling, the constructs can be tested in any suitable cell line, for example but not limited to BJ-TERT/LT/ST/RAS$^{V12}$ cells and BJ-TERT/LT/ST cells, Calu-1 cells, which have mutant KRAS, and derivative cells with mutant KRAS knocked down, and HT1080 cells, and a derivative line with mutant NRAS knocked down. For RAF signaling, we will test the constructs in A673 cells (BRAF mutant) and a derivative cell line with BRAF knocked down. To determine the effect of MEK signaling, the constructs can be tested in any suitable cell line, including but not limited to BJ-TERT/LT/ST/RAS$^{V12}$, Calu-1, HT1080 and/or A673 cells, each treated with one of three different MEK1/2 inhibitors. In each of these cases, the assay can determine whether there is a change in the fluorescence of the CFP-VDAC-YFP construct when RAS-RAF-MEK signaling is active or inhibited. One form of a suitable negative control can be a mitochondrial outer membrane targeted CFP-YFP fusion protein that lacks most of the VDAC sequence. A suitable form of a positive control can be a constitutively open VDAC mutant as described herein. Erastin can be tested to determine whether it causes VDAC opening in cells, as measured by this CFP-VDAC-YFP fluorescent reporter. Cellular fractions containing mitochondria and/or purified mitochondria from cells expressing any one of the CFP-VDAC-YFP reporters, including reporters with a VDAC mutations can also be used. In assays using purified mitochondria or cellular fractions with mitochondria, NADH can be used as a control for inducing VDAC closure. In certain aspects, the invention provides methods which determine whether the RAS-RAF-MEK signaling causes VDAC closure.

In other embodiments, a fluorescent VDAC reporter can be used as a pharmacodynamic marker for erastin in mice. Stably transfected HT1080 and Calu-1 cells harboring this fluorescent VDAC reporter, can be grafted in mice, which are treated with erastin or related analogs. After erastin treatment, the tumor can be excised and the fluorescence of the VDAC reporter measured. This can ascertain whether erastin is getting into the tumor xenograft and inducing the desired opening of VDAC in the mouse model.

Knock Down Candidate MAPK Proteins and Measure Effects on VDAC Levels and Closure:

To delineate the specific RAS-RAF-MEK pathway that regulates VDAC levels and closure, the effect of knocking down candidate MAPK proteins downstream of MEK can be tested. The canonical RAS-MAPK pathway involves a RAS-RAF-MEK1/2-ERK1/2 cascade[168]. However, there are additional ERK proteins (ERK3-8) and other MAPK proteins (p38 and JNK proteins) that could potentially be involved. In addition, there might be other kinases acting upstream or downstream of this cascade. The activity of human kinases and kinase-related proteins (about 850 proteins with predicted function) can be knocked-down using 4,250 lentiviral shRNA constructs. shRNA constructs are created and available from the RNAi consortium[125]. The set of shRNAs targeting human kinases or kinase-related proteins can be organized and maintained as a subset of the entire shRNA collection, wherein stocks of lentivirus for each of these 4,250 constructs are maintained. These virus stocks are aliquoted in multiple 384-well plates. To test the effect of knocking down each kinase on erastin sensitivity, the virus can be added to HT1080 cells, and after 24 h, selected by puromycin selection (each shRNA construct contains a puromycin resistance gene). After 1, 3 and 5 days (i.e. in parallel experiments), erastin can be added, after 24 h, cell death/viability can be determined by adding alamar blue to a final volume of 10%. For a subset of shRNAs, for example those targeting ERK1-8 and all those confirmed to cause erastin resistance, the desired target mRNA knock-down can be examined by qPCR and western blotting. All candidate shRNAs can be validated by creating at least 3 shRNAs capable of knocking down the same target mRNA >80% and confirming they all cause resistance. A silent mutation can be created in the target mRNA that prevents knockdown, and tested whether this mutation restores erastin sensitivity. In all candidate cell lines with shRNAs that cause erastin resistance, the effect of knocking down the kinase activity on: VDAC 1, 2 and 3 mRNA and protein levels, and the effect on VDAC closure, can be measured as described herein. In certain aspects, the invention provides methods to define additional kinases on the RAS-MAPK pathway that lead to increased VDAC protein levels and increased erastin sensitivity.

Determining the Subcellular Localization of Erastin-Binding Activity:

Although almost all of the VDAC proteins are localized to mitochondria, there is evidence that a small amount of VDAC1 is localized to the plasma membrane[74-76, 81]. Thus, it can be demonstrated that erastin binds to mitochondrial VDACs, as opposed to plasma membrane VDACs. To address this issue, radiolabeled erastin can be synthesized. In one embodiment, a $^3$H-labeled erastin analog can be synthesized by acetylating erastin A3 with [H$^3$]—CH$_2$COCl; A3 is an affinity analog used to purify VDAC. In another embodiment, $^{125}$I-labeled erastin can be synthesized, in which the label replaces the p-chloro substituent in erastin. In another embodiment, a $^3$H-labeled erastin analog can be synthesized in which the chiral methyl position is replaced with an acetamidoethyl group, this site tolerates larger groups such as a propylphthalamide without losing activity. In each embodiment, a charcoal precipitation assay can be used to measure binding of the radiolabeled analog to subcellular fractions (nucleus, cytosol, mitochondria and plasma membrane). In another embodiment, the method can comprise a step for determining whether the binding can be competed with erastin itself. These studies will determine whether erastin-like compounds bind to a mitochondrial target (i.e. mitochondrial VDAC).

Creating Mitochondria-DNA-Deficient Cells and Testing the Effect on Erastin Sensitivity:

In certain aspects, the invention provides that erastin interacts with mitochondrial VDACs to cause mitochondrial dysfunction; disrupting the electron transport chain should cause resistance to erastin. Antimycin A, a mitochondrial complex III inhibitor, causes resistance to erastin (Table 3). Another method that can determine whether erastin induces mitochondrial dysfunction is to generate $\rho^0$ cells, cells lacking mitochondrial DNA and therefore a functional electron transport chain, and test the effect on erastin lethality.

$\rho^0$ cell derivatives for three different cell lines (HT1080, Calu-1 and BJ-TERT/LT/ST/RAS$^{V12}$) can be generated by treatment with 1.5 µg/mL ditercalinium, as described[169, 170], for 2 months. Single-cell clones can be isolated and their mitochondrial DNA-deficiency confirmed by (i) Southern blot with a mtDNA probe, (ii) PCR analysis using primers derived from positions 8196-8215 and 8726-8707 of human mitochondrial DNA, and [$^{35}$S]-labeling of mitochondrial translation products using [$^{35}$S]-methionine and emetine, which inhibits cytoplasmic translation. In addition, $\rho^0$ cells should be unable to grow in the absence of uridine or pyruvate. $\rho^0$ cells also lack cytochrome c oxidase activity, which can be confirmed using an established assay[171]. Medium from cell cultures in 96-well plates is aspirated, 0.01% saponin is added in water to permeabilize cells, reduced cytochrome c is added, and catalase and 4 mM 3,3' diaminobenzidine (DAB) in 0.1 mM sodium phosphate buffer are added. DAB is oxidized by the oxidized cytochrome c produced by the assay, resulting in a polymer that is detectable at 450 nm. By performing the experiment in the presence or absence of KCN, the specificity of the assay can be monitored. The sensitivity of $\rho^0$ cells to erastin can be tested using an automated trypan blue exclusion assay, on a Beckman Vi-Cell, using a dilution series of erastin in replicate. This assay can determine whether mitochondrial respiratory activity is necessary for erastin's lethality.

Methods to Determine the Effect of Expressing Mitochondria-Targeted Catalase and Ferritin on Erastin Sensitivity:

If erastin causes the appearance of hydrogen peroxide and Fe$^{+2}$ in mitochondria, then expression of mitochondria-targeted catalase or ferritin is likely to cause resistance to erastin. In certain aspects, the invention provides methods for expressing mitochondrial ferritin and mitochondrial catalase in HT1080, Calu-1 and BJ-TERT/LT/ST/RAS$^{V12}$ cells. A mitochondrially-localized catalase construct is previously described[172]. This construct can be cloned into pLKO.1, the lentiviral expression vector used successfully to deliver shRNAs and GFP to these cells. As controls, wild-type human catalase, which has a peroxisomal localization signal, a nucleus-targeted catalase construct, which was described previously[172], or GFP can be expressed. In each case, we will transfect each construct into 293T cells along with a vector expressing VSVG (pMD.G) and a packaging vector (pCM-VdR.89), harvest supernatant after 48 h and infect three cell lines that are sensitive to erastin (HT1080, Calu-1 and HeLa). We will measure cell lethality using trypan blue exclusion on a Vi-Cell.

To test the role of free iron in erastin's mechanism of action, mitochondrial ferritin[173] or cytosolic ferritin (both heavy and light chains) can be expressed in HT1080, Calu-1 and HeLa and their effect on erastin's lethality measured. These studies can determine whether iron and hydrogen peroxide are necessary for erastin's lethality, and whether these species are in mitochondria.

Methods to Create and Test Constitutively Open VDACs for their Ability to Phenocopy Erastin:

In certain aspects, the invention provides that erastin locks one or more VDAC proteins into an open conformation, causing dysregulated flux of ions and metabolites through the outer mitochondrial membrane. In certain embodiments, the invention provides methods for creating mutants of each VDAC which mutants are constitutively open, and phenocopy erastin lethality.

Certain VDAC mutants have altered gating properties in vitro. The voltage sensor in VDACs consists of multiple lysine residues that respond to a transmembrane voltage potential by instigating large conformational changes in the channel, rendering it poorly conducting to anions such as ATP/ADP[70]. Single mutation of each of five different lysine residues to glutamate (K19E, K46E, K61E, K65E and K84E) increased the voltage required to close the channel. Thus, VDAC proteins with mutations, single mutations or combinations of multiple mutations would have a greater fraction of open channels when expressed in cells. Expressing these mutants in tumor cells can test the notion that opening VDAC channels leads to the lethality induced by erastin. Single mutations or combinations of multiple mutations can be created in all three VDAC isoforms using overlap-extension PCR, all resulting cDNAs can be sequenced and cloned into pLKO.1[125]. K→E mutant VDAC proteins can be expressed in three tumor cell lines (HT0180, Calu-1 and HeLa) by transfecting a packaging cell line (293T) along with a vector expressing the coat protein VSVG (pMD.G) and a packaging vector (pCMVdR.89), and transferring the supernatant to target cells. Viability can be tested at 24, 48 and 72 h after infection using trypan blue (on a Beckman Vi-Cell). For constructs that cause lethality, the type of cell death can be characterized to determine if it phenocopies erastin: the determination can include (i) whether anti-oxidants and iron chelators can prevent mutant-VDAC-induced cell death, (ii) whether there are reactive oxygen species (ROS) which can be measured directly using flow cytometry with the ROS-sensitive compound dihydrodichlorofluorescein and (iii) whether hallmarks of apoptosis are activated or not. In certain aspects, the invention provides that opening of VDAC channels leads to an oxidative, non-apoptotic mode of cell death, which is the hallmark of erastin lethality.

Methods to Perform Large-Scale shRNA Suppressor Screens to Discover Other Regulators of Erastin Sensitivity:

The above-described experiments are targeted to the specific hypothesis we currently hold regarding erastin's mechanism of action. Another method of illuminating erastin's mechanism of action is to perform a large suppressor screen for shRNA constructs that prevent erastin lethality. Such a screen can reveal that knockdown of VDAC mRNAs causes resistance to erastin, identifying these critical proteins in erastin's mechanism of action. Such a screen can illuminate: (i) proteins downstream of the RAS-RAF-MEK cascade that lead to increased VDAC abundance (and therefore increased erastin sensitivity), (ii) factors that regulate the pool of free iron that is needed for erastin's lethality, (iii) proteins involved in regulating abundance of the critical substrates whose gating by VDAC is altered in the presence of erastin, and (iv) pathways involved in detoxifying the oxidative species generated by erastin treatment.

To perform this shRNA suppressor screen, a collection of 90,000 shRNA clones in the pLKO.1 vector that was generated as part of the RNAi Consortium can be used[125]. There is a high-throughput protocol for producing plasmid DNA and lentivirus for this collection, and this protocol was validated in a screen for anti-mitotic shRNAs (see Moffat et al). To perform this screen, a co-transfection (with Fugene) can be carried out in 293T cells in a multi-well format using each pLKO.1 shRNA vector with packaging and envelope vectors. Supernatant can be harvested after 48 h, aliquoted and frozen. For the screen itself, about 3,000 HT1080 cells per well of a 384-well plate can be seeded. The screen used a calibration of the relationship between cell number and alamar blue fluorescence and determination that 3,000 cells gives us a signal in the middle of the dynamic range of the assay. The next day, one lentiviral shRNA stock is added to each well of the plate using a Beckman Biomek FX with integrated Cytomat hotel (and enclosed in a BL2 Baker Bioprotect II Hood). The plates are incubated for 48 h to allow time for knockdown to occur and for residual protein to turn over. A lethal dose of erastin (5 µM) is added to all wells of the plate (except untreated control wells). After 20 h, alamar blue is added. Alamar blue reduction is measured by excitation at 530 nm and emission at 590 nm on a Victor3 (PerkinElmer) fluorescence platereader. shRNA clones that cause >50% rescue of erastin-induced cell death can be retested to confirm their activity. shRNA can include shRNAs targeting mRNAs coding for proteins involved in oxidative stress, mitochondrial function, iron metabolism, death signaling and RAS signaling.

Once active shRNAs that suppress erastin's lethality are identified, the target mRNAs for each shRNA can be determined. At least five shRNAs targeting the same mRNA in parallel can be tested. Discovering more than one shRNA targeting the same mRNA increases confidence that the putative target mRNA is in fact the correct target mRNA. In addition, knockdown of the target mRNA can be determined by qPCR, and of the corresponding protein using western blotting. For the most effective mRNA targets, another step can determine that the target mRNA is responsible for the erastin resistance by creating a cDNA that contains a silent mutation that renders the cDNA resistant to each shRNA construct. HT1080 cells can be co-infected with each shRNA and the corresponding non-degradable cDNA, to determine whether this restored erastin lethality. If degradation of a specific mRNA truly causes resistance to erastin, then expressing such an shRNA-resistant cDNA for the target mRNA should restore erastin sensitivity. This shRNA suppressor screen will yield candidate mRNA (and corresponding proteins) that cause resistance to erastin. These can yield information on the pathways leading to erastin sensitivity and erastin-induced oxidative death.

In certain embodiments, the sensitivity to erastin, can be tested in cell lines that are resistant to taxol and vinblastine. The sensitivity of CCRF-CEM parental, and taxol and vinblastine resistant derivative cells to erastin was tested. In certain aspects, the invention provides that erastin is equally effective in inducing cell death in all 3 lines, CCRF-CEM parental, and taxol and vinblastine resistant derivative cell, with $IC_{50}$=11 µM, 7 µM and 8 respectively, wherein taxol ($IC_{50}$=1 nM, 560 nM, 1379 nM) and vinblastine ($IC_{50}$=1 nM, 93 nM and 370 nM) are not effective in inducing cell death. Thus, cross resistance to erastin does not develop in taxol or vinblastin resistant cell lines. Erastin analogues can be tested to ensure their effectiveness in inducing cell death in tumor cell line which are resistant to taxol or vinblastin, or other ant-tumor agents.

Determine Pharmacokinetics of Erastin:

Pharmacokinetic parameters (AUC, $t_{1/2}$ and $C_{max}$) in plasma and in xenograft tumors can be measured, using standard procedures. Briefly, heparinized blood samples can be collected at the following time points: 5, 10, 20, 30, 60 min and 2, 3, 4, 5, 6, 8, 16 and 24 hours, following administration of erastin, or erastin analogues. Different routes of administration, such as for example IP, IV and PO, can be compared to determine differences in pharmacokinetic and pharmacodynamic parameters. HPLC-UV and LC-MS can be used to measure analog concentrations at each time, relative to an internal standard. AUC, $t_{1/2}$ and $C_{max}$ can be determined using WinNonLin v 4.1 (Pharsight). These studies can determine the optimal route of administration, the likely dosing schedule that will be needed, and can provide an estimate of the desired treatment dose. This information can be used in designing murine xenograft efficacy experiments with compounds selected for in vivo testing.

In certain embodiments, erastin was formulated at 150 mg/kg in 10% DMSO, 20% Tween 80, 70% saline and 0.5 mL of this formulation was injected via IV twice per day for four days in 3 nude mice. No gross toxicity, judged for example by body weight and behavior, was observed. In addition, the effects of single dose IP injections of erastin in 100% DMSO up to 450 mg/kg was tested and no overt toxicity was observed, suggesting erastin is relatively benign and non-toxic. Thus, PK experiments can be initiated using the DMSO/Tween 80/saline formulation.

In Vivo Efficacy Testing of Erastin, or Erastin Analogs Using Human Tumor Xenografts in Nude Mice:

To test the effect of erastin, or erastin analogs on tumor size in mice, six-week old athymic nude female mice (from NCI's Frederick Cancer Center) can be used. These experiments can be performed as per previously published work[174, 175]. HT1080, Calu-1 and A673 cells can be tested for suitability in generating xenografts. When tumors reach 5 mm in diameter, the mice can be distributed into treatment groups randomly. A stock solution of erastin or an analog thereof to be tested can be prepared in DMSO/Tween 80 saline. The dose will depend on the results of preclinical assessment, and can be in the range of 1-100 mg/kg. Mice can be dosed up to 3× per day, according to the pre-clinical assessment of the rate of drug elimination. After the dosing regimen has been completed, for example but not limited to twice per day for five days, possibly repeated one or more times, the mice will be sacrificed using Nembutal and $CO_2$ euthanasia. Tumor diameter can be determined by caliper. Tumor size, expressed as tumor volume in cubic millimeters, can be measured in untreated and several groups, treated with different doses of each analog and with a control such as paclitaxel or doxorubicin.

The following examples are provided to further illustrate the methods and compositions of the present invention. These examples are illustrative only and are not intended to limit the scope of the invention in any way.

EXAMPLES

Engineered Human Tumor Cells

Primary human cells can be converted into tumorigenic cells by introduction of vectors expressing hTERT, oncogenic RAS, and other proteins that disrupt the function of p53, RB, and PP2A[55-60]. Such engineered human tumorigenic cells and their precursors (FIG. 1), were created from primary human foreskin fibroblasts. Characteristics of these cells reported previously include doubling time, resistance to senescence and crisis in culture, response to irradiation, ability to grow in an anchorage-independent fashion, and ability to form tumors in mice[56, 57, 60]. These cells were used to discover RAS-selective lethal compounds, including a compound named erastin.

Cell Culture and Western Blotting:

BJ-TERT/LT/ST/RAS$^{V12}$ cells were cultured as described (Dolma, S., Lessnick, S. L., Hahn, W. C. & Stockwell, B. R. Identification of genotype-selective antitumor agents using synthetic lethal chemical screening in engineered human tumor cells. Cancer Cell. 3: 285-96 (2003). Other cell lines were grown according to specifications of the American Type Culture Collection. For BRAF knockdown, A673 cells were infected with pSIRIPP-derived retroviruses (Sage, J., Miller, A. L., Perez-Mancera, P. A., Wysocki, J. M. & Jacks, T. Acute mutation of retinoblastoma gene function is sufficient for cell cycle re-entry. Nature. 424: 223-8 (2003), expressing short-hairpin RNAs against either BRAF or luciferase, and were selected in 2 ug/ml puromycin to remove uninfected cells. The sequences of the cloned oligonucleotides were as follows: BRAF:5'-GAT CCC CGT GTT GGA GAA TGT TCC ACT TCA AGA GAG TGG AAC ATT CTC CAA CAC TTT TTG GAA A-3' (SEQ ID NO:28); Luciferase:5'-GAT CCC CCT TAC GCT GAG TAC TTC GAT TCA AGA GAT CGA AGT ACT CAG CGT AAG TTT TTG GAA A-3' (SEQ ID NO:29).

For western blots, medium was aspirated, and each dish was washed twice with 10 mL of ice-cold PBS. Cells were lysed with 200 μL of buffer (50 mM HEPES, 40 mM NaCl, 2 mM EDTA, 0.5% Triton-X, 1.5 mM sodium orthovanadate, 50 mM NaF, 10 mM Na Pyrophosphate, 10 mM Na B-glycerophosphate and protease inhibitor tablet, pH 7.4). Samples were separated using SDS-PAGE, transferred to a PVDF membrane, blocked for 1 hour at room temperature in Licor Odyssey Blocking Buffer and incubated with the necessary primary and secondary antibodies: anti-VDAC1 (Abcam, #ab3434), anti-VDAC1 (Calbiochem, #529534), anti-VDAC2 (Abcam, #ab22170), anti-eIF4E (Santa Cruz Biotechnology, #sc-9976), anti-α-Tubulin (Sigma, #T6199), anti-actin (Santa Cruz Biotechnology, #1616R), IRDye 800 goat anti-rabbit antibody (Rockland Immunochemicals, #611-132-122), Alexa Fluor 680 goat anti-mouse (Molecular Probes, #A21058), PathScan Multiplex Western Cocktail I Kit (Cell Signaling Technology), anti-PARP (Abeam, #ab105). Membranes were scanned using the Licor Odyssey™ Imaging System.

PARP Cleavage and Cytochrome C Release:

BJ-TERT/LT/ST/RAS$^{V12}$ cells were seeded in polystyrene 100×20 mm dishes (Falcon/#353003) in 10 ml of media. Three million cells were seeded in each dish. After overnight incubation at 37° C. with 5% $CO_2$, BJ-TERT/LT/ST/RAS$^{V12}$ cells were treated with nothing, staurosporine (1 μM) for 6 h, camptothecin (1 μM) for 18 h or erastin (20 μg/mL) for 6, 10, 12, 12.5, 13, 14, 18 or 26 h, and prepared for western blotting.

For the cytochrome c release assay, cells were washed with 10 mL of ice-cold PBS, suspended in 120 μL of buffer (300 mM sucrose, 0.1% BSA, 10 mM HEPES, pH 7.5, 10 mM KCl, 1.5 mM $MgCl_2$, 1 mM EGTA, 1 mM EDTA, 1 mM dithiothreitol, 2 mM phenylmethanesulfonyl fluoride and 1 protease inhibitor tablet (Roche)) and incubated on ice for 15 min. Cells were lysed by passing them through a 25-gauge needle (five strokes). Cell lysates were centrifuged at 1850 rpm for 5 mM at 4° C. to remove the nuclear fraction. Mitochondria were removed from the soluble cytosolic fraction by pelleting at 10000 rpm. Supernatant and mitochondrial pellets were solubilized in SDS-PAGE loading buffer and analyzed by western blotting.

Oxidative Species Detection:

2'7'-dichlorodihydrofluorescein diacetate ($H_2$DCF-DA, Molecular Probes) was used to measure oxidative species by flow cytometry. Non-fluorescent $H_2$DCF-DA is cleaved by endogenous esterases and then is oxidized to generate fluorescent dichlorofluorescein (DCF). BJ-TERT/LT/ST/RAS$^{V12}$ and BJ-TERT cells were seeded at $3\times10^5$ cells per dish in 60-mm dishes and allowed to grow overnight. Cells were treated with 4.6 μM erastin for 2, 4, 6, 8, 10 and 12 h. For each time point, controls were maintained for untreated cells and also for positive control (treated directly with 500 hydrogen peroxide for five minutes). Cells were incubated with 10 μM of $H_2$DCF-DA for 10 minutes, harvested by trypsinization, washed twice with cold PBS, resuspended in 100 μl of PBS and incubated with 5 μl of 50-μg/ml propidium iodide for 10 minutes. 400 μl of PBS was added and the solution analyzed by flow cytometry (FACSCalibur-Becton-Dickinson). FL1-H indicates DCF fluorescence units detected.

VDAC Chemi-Proteomic Identification:

Cultures of BJ-TERT and BJ-TERT/LT/ST/RAS$^{V12}$ cells (ten 150 mm plates) were washed with PBS, lysed in 25 mM hydroxyethylpiperazine-N'-2-ethanesulfonic acid (HEPES) pH 7.5, 150 mM NaCl, 1% NP-40, 10 mM $MgCl_2$, 1 mM ethylene-diamine tetra acetate (EDTA), 10% glycerol, 1 mM dithiothreitol (DTT) and protease inhibitor cocktail. Protein concentration was determined using a Bradford colorimetric assay.

Erastin A3 and B2 were dissolved in DMSO at 10 mg/ml. 100 μL of AffiGel-10 was washed and resuspended in 400 μl DMSO. 10 μL of compound and 3 μL of 1:100 dilution of triethylamine in DMSO were added. The suspension was incubated at RT for 12 h, washed (1 mL/wash) 5×DMSO, 3×PBS, resuspended in 3 M ethanolamine in PBS, incubated 1 h at RT, washed 5×PBS, diluted 1:1 in PBS, washed with HEGN binding buffer (0.1 M KCl, 20 mM HEPES, pH 7.6, 0.1 mM EDTA, 10% glycerol, 0.1% NP-40, 1 mM DTT, 0.25 mM PMSF) and incubated with 1 ml cell lysate (2 mg/ml) for 1.5 at 4° C., washed with HEGN binding buffer, 3× with HEGN high salt buffer (0.35M KCl, 20 mm HEPES, pH 7.6, 0.1 mm EDTA, 10% glycerol, 0.1% NP-40, 1 mm DTT, 0.25 mM PMSF), 1× with HEGN binding buffer, and eluted 2× with 50 μL HEGN elution buffer (HEGN binding buffer, 0.8% N-lauroyl sarkosine) 15 min each; proteins from the supernatant were precipitated with 400 μL ethanol, sedimented by centrifugation (14,000 rpm) and digested as described (Zheng, Y. et al. Essential role of the voltage-dependent anion channel (VDAC) in mitochondrial permeability transition pore opening and cytochrome c release induced by arsenic trioxide. *Oncogene.* 23: 1239-47 (2004). Reverse-phase-HPLC was performed using a nano LC system from Dionex: a 75 μm×150 mm column, a Famos autosampler, a Switchos II system and an UltiMate binary pumping module. Samples were analyzed using both a 4700 Proteomics Analyzer MALDI-TOF/TOF (TOF/TOF; Applied Biosystems) and a Q Trap (AB/MDS Sciez) and the peptide level data were combined. To construct the databases used for protein identification, the following steps were performed: The NCBInr protein sequence FASTA file was downloaded, the gi numbers were updated, and the missing or incorrectly annotated taxonomies were fixed by referencing them to the NCBI taxonomy index (index of gi number vs. species). The human subset of proteins in the database was extracted into a separate database (HumanNR). All protein sequences in HumanNR were matched to the corresponding protein in RefSeq using BLAST (Altschul, S. F., Gish, W., Miller, W., Myers, E. W. & Lipman, D. J. Basic local alignment search tool. *J Mol Biol.* 215: 403-10 (1990). MS/MS data obtained from the TOF/TOF and Q TRAP were searched using Mascot (Matrix Sciences, London, UK). All searches were performed against either the corrected NCBInr protein sequence database or the HumanNR database. GPS Explorer (Applied Biosystems) was used for submitting data acquired from the TOF/TOF for database searching. The Mascot-based search was performed using the default settings for the specific instrument type as supplied by Matrix Science, except that ions with scores below 10 were excluded from the results.

The spectra of the peptides identified in the automatic data analysis were manually inspected for the quality of the corresponding spectra and consistency with the obtained results. Only high quality spectra and results with a peptide score of 20 or higher were accepted and used for the identification of proteins.

Transmission Electron Microscopy of BJ-TERT/LT/ST/RAS$^{V12}$ Cells Treated with Erastin:

Cells were fixed 24 h with 2.5% glutaraldehyde in 0.1 M Sorenson's buffer (0.1 M H2PO4, 0.1 M HPO4, pH 7.2) for at least one hour, treated with 1% OsO4 in 0.1 M Sorenson's buffer for 1 h. Enblock staining used 1% tannic acid. After dehydration through an ethanol series, cells were embedded in Lx-112 (Ladd Research Industries, Inc) and Embed-812 (EMS, Fortwashington Pa.). Thin sections were cut on an MT-7000 ultramicrotome, stained with 1% uranyl acetate and 0.4% lead citrate and examined under a JEOL JEM-1200 EXII electron microscope. Pictures were taken on an ORCA-HR digital camera (Hamamatsu) at ~20,000-fold magnification, and measurements were made using the AMT Image Capture Engine.

ATP Detection:

Cells were seeded in polystyrene 100×20 mm dishes (Falcon/#353003) in 10 mL of media. Three million cells were seeded in each dish for staurosporine (STS) and erastin treatment. Two million cells were seeded in each dish for no treatment and hydrogen peroxide treatment. Cells were treated with staurosporine (1 μM) for 12 hours, with $H_2O_2$ (16 mM) for 1.5 hours and erastin (20 μg/mL) for 12 hours. After the incubation, we counted cells using a CiCell analyzer (Beckman). 100,000 cells from each treatment were collected and washed twice in Hank's Salt Solution (10 ml). Next, we suspended cells in 200 μl of Nucleotide Releasing Buffer (BioVision/K254-200 ApoSensor Cell Viability Assay Kit) and incubated at room temperature for 10 minutes. To 10 μl of the above sample, we added 1 ul of ATP Monitoring Enzyme (BioVision/K254-200 ApoSensor Cell Viability Assay Kit) and read the ATP levels of the samples using a luminometer.

Knockdown Using Lentiviral shRNAs:

VDACs, KRAS and BRAF were knocked down in HT1080, Calu-1, and A673 cells, respectively, using short hairpin RNA lentiviral vectors. On day 1, 293T cells were seeded in 10 cm tissue culture dishes (2×10$^6$ cells/dish). On day 2, shRNA-plasmid construct (pLKO.1 vector) and the pDelta.8.9 and pVSV-G helper plasmids were co-transfected into the 293T cells using FuGENE® 6 Transfection Reagent. On day 3, the medium was changed. On day 4, the supernatant, containing virus, was transferred to HT1080 cells in 10 cm tissue culture dishes (1×10$^6$ cells/dish). On day 5, cells were transferred to 175 cm$^2$ flasks and medium was supplemented with puromycin. On days 6 and 7, medium was changed and supplemented with puromycin. On day 8, samples were harvested for Western Blot and quantitative RT-PCR, or reseeded in 6-well format (5×10$^5$ cells/well), in duplicate, and treated with erastin dilutions. For BRAF knockdown, A673 cells were infected with pSIRIPP-derived retroviruses expressing short-hairpin RNAs against either BRAF or luciferase, and were selected in 1.5 μg/ml puromycin to remove uninfected cells. All cells were cultured at 37° C., 5% $CO_2$, in growth media as recommended by ATCC. (Sage, J., Miller, A. L., Perez-Mancera, P. A., Wysocki, J. M. & Jacks, T. Acute mutation of retinoblastoma gene function is sufficient for cell cycle re-entry. Nature 424, 223-8 (2003).)

ATP levels were measured in BJERL cells treated with nothing (NT), treated with 1 μM of Staurosporine (STS) for 12 hours, with 16 mM of hydrogen peroxide for 1.5 hours and 20 μg/mL of erastin for 12 hours. ATP levels were normalized by number of viable cells.

VDAC3 shRNAs Induce Isoform-Selective Knockdown in HT1080 Cells. Briefly, the assay was carried out as follows: Day 1, 293T cells seeded in 10 cm tissue culture dishes (2×10$^6$ cells/dish); Day 2, shRNA-plasmid construct (pLKO.1 vector) introduced to cells using FuGene transfection reagent; Day 3, medium changed; Day 4, supernatant transferred to HT1080 cells in 10 cm tissue culture dishes (1×10$^6$ cells/dish); Day 5, cells transferred to 175 cm$^2$ flasks, medium supplemented with puromycin; Days 6 and 7, medium changed and supplemented with puromycin; Day 8, samples harvested for qRT-PCR. Unique shRNAs (V3.B1, V3.B2, V3.B3, V3.B5, V3.B5, V3.B6), control construct (GFP).

VDAC1 shRNAs Induce Isoform-Selective Knockdown in HT1080 Cells. Briefly, the assay was carried out as follows: Day 1, 293T cells seeded in 10 cm tissue culture dishes (2×10⁶ cells/dish); Day 2, shRNA-plasmid construct (pLKO.1 vector) introduced to cells using FuGene transfection reagent; Day 3, medium changed; Day 4, supernatant transferred to HT1080 cells in 10 cm tissue culture dishes (1×10⁶ cells/dish); Day 5, cells transferred to 175 cm² flasks, medium supplemented with puromycin; Days 6 and 7, medium changed and supplemented with puromycin; Day 8, samples harvested for qRT-PCR. Unique shRNAs (V1.161, V1.279, V1.396, V1.607, V1.921), control construct (GFP).

Overexpression of VDAC3 Using Lentiviral Constructs:

VDAC3 was overexpressed in BJ-TERT cells, respectively, using a human ORF clone (Invitrogen) recombined into the pLENTi6/V5-DEST lentiviral vector (Invitrogen). On day 1, 293T cells were seeded in 10 cm tissue culture dishes (2×10⁶ cells/dish). On day 2, the VDAC3 construct and the pDelta8.9 and pVSV-G helper plasmids were co-transfected into the 293T cells using FuGENE® 6 Transfection Reagent (Roche). On day 3, the medium was changed. On day 4, the supernatant, containing virus, was transferred to BJ-TERT cells in 10 cm tissue culture dishes (1×10⁶ cells/dish). On day 5, cells were transferred to 175 cm² flasks and medium was supplemented with Blasticidin (5 µg/mL). On days 6 and 7, medium was changed and again supplemented with Blasticidin. These cells were maintained in selection medium for 12 days before samples were harvested for Western Blot and quantitative RT-PCR, or reseeded in 6-well format (5×10⁵ cells/well), in duplicate, and treated with erastin dilutions.

Reverse Transcription and Quantitative PCR:

Total RNA was isolated from cells using RNeasy Mini Kit (QIAGEN). Reverse Transcription was performed on 2 µg of isolated RNA using Taqman Reverse Transcription Reagents (Applied Biosystems). The ABI Prism 7300 was then used for Quantitative PCR. 20 ng of cDNA product was mixed with Power SYBR Green PCR Master Mix (Applied Biosystems) and the appropriate forward/reverse primer set. Relative mRNA expression levels were quantified with Applied Biosystems Sequence Detection Software v1.3.1.

NADH Oxidation Assay:

NADH oxidation in the mitochondria was measured by resuspending mitochondria isolated from yeast in R-buffer (0.65 M sucrose, 10 mM HEPES (pH 7.5), 10 mM $KH_2PO_4$, 5 mM KCl, 5 mM, $MgCl_2$) to a final concentration of 100 µg/ml. Mitochondrial concentration was measured by dissolving mitochondria in 0.6% SDS and reading absorbance at 280 nm. The mitochondrial suspension was then incubated with 25 µM NADH, and the absorbance at 340 nm monitored over a 15 minute period. The assay was repeated in the presence of erastin. To assess mitochondrial intactness, a parallel assay was run in which mitochondria were hypotonically shocked prior to addition of NADH. The mitochondrial pellet was resuspended in $dH_2O$ and incubated on ice for 3 minutes to disrupt the outer mitochondrial membrane. 2× R-buffer was then added to restore normal osmotic conditions.

Cell Viability Assays:

Trypan Blue exclusion: Cells were trypsinized, pelleted, resuspended in 1 mL growth media. Trypan Blue exclusion analysis was performed using the Vi-CELL™ Series Cell Viability Analyzer 1.01 (Beckman Coulter).

Alamar Blue metabolism: 10% Alamar Blue was added to assay plates, which were then incubated for an additional 16 hours. Red fluorescence, resulting from reduction of Alamar Blue, was detected on a Victor3 platereader (ex: 530, em: 590).

VDAC2 Binding Assay:

VDAC2 protein was isolated from E. coli using a modified version of the protocol originally described by Koppel et al. Bacterial cultures were grown in LB containing 50 mg/L ampicillin to an OD of 0.6, and induced using 0.4 µM IPTG overnight. Cultures were harvested by centrifugation at 6000×g for 10 min. The pellet was then washed with $dH_2O$ and resuspended in buffer (20% sucrose, 20 mM Tris, pH 8.0, 50 µM/mL lysozyme) and incubated at 25° C. for 10 minutes. The lysate was then sonicated for 2×30 seconds and centrifuged at 15000×g for 20 minutes. The pellet was resuspended in resuspension buffer (4.5 M guanidine-HCl, 0.1M NaCl, 20 mM Tris, pH 8.0) and incubated for 1 hour at 25° C. The suspension was then centrifuged (20 minutes, 15000×g), and the supernatant was loaded on a Ni-NTA Superflow column (Qiagen) pre-equilibrated with 5 volumes of resuspension buffer. The column was washed with 5 column volumes of resuspension buffer containing 10 mM imidazole. The protein was then eluted using resuspension buffer containing 225 mM imidazole. The eluate was dialysed against 0.1 M NaCl, 20 mM Tris, pH 8.0, and 2% LDAO (Fluka) overnight, and then concentrated via centrifugation to 4 mg/mL.

To assay direct binding of erastin analogs, 40 µg of purified VDAC2 was resuspended in 100 µL of Binding Buffer (25 mM HEPES, pH 8.0, 0.1% BSA, 7 mM $MgCl_2$, 15 mM NaCl), and incubated in the presence of 20 µM radiolabelled erastin A9 and erastin A9 or erastin A8 for 15 minutes. The mixture was then deposited onto Protran BA85 0.45 µM binding filters (Whatman) using vacuum filtration. The filter was rinsed 5 times with 1 mL wash buffer (25 mM HEPES, 0.1% BSA), and then incubated in 5 mL scintillation liquid (Cytoscint, MP biomedicals). Radioactivity was detected on a LKB Wallac 1211 RACKBETA Liquid Scintillation Counter.

TABLE 2

Activity of RAS-selective lethal compound erstin in tumor cell lines. $IC_{50}$ values (ng/mL) are shown using the Alamar blue viability assay. BJ engineered tumor cells express TERT, LT, ST, and oncogenic RAS. Isogenic RASV12 lacking cells are identical but lack HRASV12. BJ-DRD cells are derived from BJ cells and contain TERT, oncogenic RAS, a truncated from of p53 (p53DD) that disrupts the tetramerization of endogenous p53, a CDK4(R24C) mutant resistant to inhibition by p16INK4A and p15INK4B (the major negative regulators of CDK4) and cyclin DI. These latter protein substitute for LT. HCT-116, A549, Calu-1, and MIA PaCa-2 are tumor cells derived from cancers (colon, lung, lung and pancreatic, respectively) known to have activating mutations in RAS.

| Cell Line | erastin |
|---|---|
| BJ-TERT/LT/ST/RASV12 | 1250 |
| BJ-TERT/LT/ST | >20,000 |
| RAS selectivity | >16 |
| BJ-TERT/LT/RASV12/ST | 1250 |
| BJ-DRD (+RAS) | 2500 |
| HCT-116 (+KRAS) | >20,000 |
| A549 (+KRAS) | >20,000 |
| Calu-1 (+KRAS) | 1000 |
| MIA PaCa-2 (+KRAS) | 5000 |

TABLE 3

Antimycin and 2-ME partially suppress erastin-induced death.

| Treatment | Cell death (%) | SD (%) |
|---|---|---|
| DMSO | 0 | 6 |
| Erastin Al | 100 | 0 |
| Antimycin | 51 | 5 |
| 2-ME | 66 | 3 |

TABLE 3-continued

Antimycin and 2-ME partially suppress erastin-induced death.

| Treatment | Cell death (%) | SD (%) |
|---|---|---|
| erastin + antimycin | 59 | 5 |
| erastin + 2-ME | 76 | 5 |

BJ-TERT/LT/ST/RAS$^{V12}$ cells were treated with 0.1% DMSO, 13 μM erastin A1, 23 μM antimycin, 126 μM 2-methoxyestradiol (2-ME) or the combinations listed and viable cells counted using a hemacytometer.

TABLE 4

Response of tumor cell lines to erastin.

| Cell line | Max % killing | EC50 (uM) | Tumor type |
|---|---|---|---|
| HOS | 100 | 17 | osteosarcoma |
| SJSA-1 | 100 | 12 | osteosarcoma |
| BJELR | 100 | 6 | foreskin fibroblasts w/TERT, LT, ST, RAS |
| SK-LMS-1 | 100 | 6 | Leimyosarcoma, vulva |
| MES-SA | 100 | 3 | Uterine sarcoma |
| HT1080 | 98 | 2 | fibrosarcoma |
| SK-ES-1 | 96 | 7 | Ewing sarcoma |
| U-2 OS | 96 | 6 | osteosarcoma |
| SK-N-MC | 95 | 10 | Neuroepithelioma |
| HeLa | 94 | 0.6 | Cervical carcinoma |
| TC71 | 92 | 10 | Ewing sarcoma |
| Hs51.T | 88 | 12 | Spindle cell sarcoma |
| TC32 | 88 | 8 | Peripheral neuroepithelioma |
| Hs 925.T | 83 | 17 | Pagetoid sarcoma |
| U973 | 73 | 10 | Acute myelogenous leukemia |
| SK-UT | 73 | 4 | Uterine, mixed mesodermal tumor |
| MX2 | 71 | 18 | Uterine Sarcoma |
| A673 | 54 | 30 | Rhabdomyosarcoma |
| EWS502 | 42 | 10 | Ewing sarcoma |
| LNCaP | 32 | 6 | prostate carcinoma |
| BJEH | 22 | 10 | foreskin fibroblast w/TERT |
| C-33 A | 21 | 0.6 | cervical carcinoma |
| SVR | 20 | 2.5 | Pancreatic carcinoma |
| A549 | 0 | — | lung carcinoma |
| HCT 116 | 0 | — | colorectal carcinoma |
| HL-60 | 0 | — | acute promyelocytic leukemia |
| SW982 | 0 | — | synovial sarcoma |
| SW872 | 0 | — | liposarcoma |
| A431NS | 0 | — | Epidermoid carcinoma |

TABLE 5

Correlation between erastin sensitivity and phospho-ERK level.

| Cell line | Erastin Sensitivity | Phospho ERK1/2 |
|---|---|---|
| A673 | 0.54 | 0.66 |
| BJ-TERT | 0.22 | 0.09 |
| BJ-TERT/LT/ST/RASV12 | 1.00 | 0.92 |
| EWS 502 | 0.42 | 0.12 |
| HL 60 | 0.00 | 0.10 |
| HT 1080 | 0.98 | 0.53 |
| SICES1 | 0.96 | 0.25 |
| SK N MC | 0.95 | 0.05 |
| SW 872 | 0.00 | 0.12 |
| TC 32 | 0.88 | 0.12 |
| TC 71 | 0.92 | 0.23 |
| U937 | 0.73 | 0.27 |

The maximum percent killing induced by erastin in each cell line is shown, along with the level of phosph-ERK1/2. The correlation is 0.41.

TABLE 6

Primer sequences

| Gene | Primer | Forward primer | Reverse primer |
|---|---|---|---|
| VDAC1 | VDAC1 | 5'-CCTGGACAGCAGGAAACAGTAAC-3' (SEQ ID NO: 30) | 5'-AGGCGTCAGGGTCAATCTGA-3' (SEQ ID NO: 35) |
| VDAC2 | VDAC2 | 5'-TGATTTTGCTGGACCTGCAA-3' (SEQ ID NO: 31) | 5'-CAGCAAGCCAGCCCTCAT-3' (SEQ ID NO: 36) |
| VDAC3 | VDAC3 | 5'-AATTTCGCCCTGGGTTACAA-3' (SEQ ID NO: 32) | 5'-TCAGTGCCATCGTTCACATGT-3' (SEQ ID NO: 37) |
| RPLPO | RPLPO.1 | 5'-ACGGGTACAAACGAGTCCTG-3' (SEQ ID NO: 33) | 5'-GCCTTGACCTTTTCAGCAAG-3' (SEQ ID NO: 38) |
| RPLPO | RPLPO.2 | 5'-GCGACCTGGAAGTCCAACTA-3' (SEQ ID NO: 34) | 5'-ATCTGCTGCATCTGCTTGG-3' (SEQ ID NO: 39) |

TABLE 7

Sequences of shRNAs

| Gene | Name of shRNA | SEQUENCE |
|---|---|---|
| VDAC1 | V1.161 | CCGGGCTATGGATTTGGCTTAATAACTCGAGTTATTAAGCCAAATCCATAGCTTTTT (SEQ ID NO: 1) |
|  | V1.279 | CCGGCAAGTACAGATGGACTGAGTACTCGAGTACTCAGTCCATCTGTACTTGTTTTT (SEQ ID NO: 2) |
|  | V1.396 | CCGGCGATTCATCCTTCTCACCTAACTCGAGTTAGGTGAGAAGGATGAATCGTTTTT (SEQ ID NO: 3) |
|  | V1.607 | CCGGGCAGTTGGCTACAAGACTGATCTCGAGATCAGTCTTGTAGCCAACTGCTTTTT (SEQ ID NO: 4) |

TABLE 7-continued

Sequences of shRNAs

| Gene | Name of shRNA | SEQUENCE |
|---|---|---|
| | V1.921 | CCGGGCTTGGTCTAGGACTGGAATTCTCGA GAATTCCAGTCCTAGACCAAGCTTTTT (SEQ ID NO: 5) |
| VDAC2 | V2.A8(A7) | CCGGGCAGCTAAATATCAGTTGGATCTCGA GATCCAACTGATATTTAGCTGCTTTTTG (SEQ ID NO: 6) |
| | V2.A9 | CCGGCAAGGTTTGAAACTGACATTTCTCGA GAAATGTCAGTTTCAAACCTTGTTTTTG (SEQ ID NO: 7) |
| | V2.A10 | CCGGCACTGCTTCCATTTCTGCAAACTCGA GTTTGCAGAAATGGAAGCAGTGTTTTTG (SEQ ID NO: 8) |
| | V2.A11 | CCGGGTGTGAGTATGGTCTGACTTTCTCGA GAAAGTCAGACCATACTCACACTTTTTG (SEQ ID NO: 9) |
| | V2.A12 | CCGGGTCAACAACTCTAGCTTAATTCTCGA GAATTAAGCTAGAGTTGTTGACTTTTTG (SEQ ID NO: 10) |
| VDAC3 | V3.B1 | CCGGGCAACCTAGAAACCAAATATACTCGA GTATATTTGGTTTCTAGGTTGCTTTTTG (SEQ ID NO: 11) |
| | V3.B2 | CCGGCCAGGAGTCAAATTGACTTTACTCGA GTAAAGTCAATTTGACTCCTGGTTTTTG (SEQ ID NO: 12) |
| | V3.B3 | CCGGCCAAACTGTCACAGAATAATTCTCGA GAATTATTCTGTGACAGTTTGGTTTTTG (SEQ ID NO: 13) |
| | V3.B4 | CCGGCCAGAATTGGAACACAGACAACTCGA GTTGTCTGTGTTCCATTTCTGGTTTTTG (SEQ ID NO: 14) |
| | V3.B5 | CCGGCAGGAGTCAAATTGACTTTATCTCGA GATAAAGTCAATTTGACTCCTGTTTTTG (SEQ ID NO: 15) |
| | V3.B6 | CCGGCCAGAAGGTGAATGAGAAGATCTCGA GATCTTCTCATTCACCTTCTGGTTTTTG (SEQ ID NO: 16) |
| NRAS | Nras.304 | CCGGCGCACTGACAATCCAGCTAATCTCGA GATTAGCTGGATTGTCAGTGCGTTTTTG (SEQ ID NO: 17) |
| | Nras.398 | CCGGGAAACCTGTTTGTTGGACATACTCGA GTATGTCCAACAAACAGGTTTCTTTTTG (SEQ ID NO: 18) |
| | Nras.445 | CCGGCAGTGCCATGAGAGACCAATACTCGA GTATTGGTCTCTCATGGCACTGTTTTTG (SEQ ID NO: 19) |
| | Nras.501 | CCGGCCATCAATAATAGCAAGTCATCTCGA GATGACTTGCTATTATTGATGGTTTTTG (SEQ ID NO: 20) |
| | Nras.655 | CCGGCAAGAGTTACGGGATTCCATTCTCGA GAATGGAATCCCGTAACTCTTGTTTTTG (SEQ ID NO: 21) |
| KRAS | Kras.269 | CCGGGACGAATATGATCCAACAATACTCGA GTATTGTTGGATCATATTCGTCTTTTTG (SEQ ID NO: 22) |
| | Kras.407 | CCGGGAGGGCTTTCTTTGTGTATTTCTCGA GAAATACACAAAGAAAGCCCTCTTTTTG (SEQ ID NO: 23) |
| | Kras.509 | CCGGCCTATGGTCCTAGTAGGAAATCTCGA GATTTCCTACTAGGACCATAGGTTTTTG (SEQ ID NO: 24) |
| | Kras.667 | CCGGGATCCGACAATACAGATTGAACTCGA GTTCAATCTGTATTGTCGGATCTTTTTG (SEQ ID NO: 25) |
| | Kras.1160 | CCGGTAGTTGGAGCTGGTGGCGTAGCTCGA GCTACGCCACCAGCTCCAACTATTTTTG (SEQ ID NO: 26) |
| BRAF | iBRAF-1 | CCGGGAGTTCAGGAGAGTAGCAATTCAAGA GATTGCTACTCTCCTGAACTCTTTTTG (SEQ ID NO: 27) |
| | iBRAF exon 5 | |

CITED LITERATURE

All documents cited, herein, including those cited below are incorporated by reference as if recited in full herein.

1. Shawver, L. K., Slamon, D. & Ullrich, A. Smart drugs: tyrosine kinase inhibitors in cancer therapy. *Cancer Cell.* 1: 117-23. (2002).
2. Capdeville, R., Buchdunger, E., Zimmermann, J. & Matter, A. Glivec (STI571, imatinib), a rationally developed, targeted anticancer drug. *Nat Rev Drug Discov.* 1: 493-502. (2002).
3. Mokbel, K. & Hassanally, D. From HER2 to herceptin. *Curr Med Res Opin.* 17: 51-9. (2001).
4. Downward, J. Targeting RAS signalling pathways in cancer therapy. *Nat Rev Cancer.* 3: 11-22 (2003).
5. Kaelin, W. G., Jr. The concept of synthetic lethality in the context of anticancer therapy. *Nat Rev Cancer.* 5: 689-98 (2005).
6. Shi, Y. et al. Enhanced sensitivity of multiple myeloma cells containing PTEN mutations to CCI-779. *Cancer Res.* 62: 5027-34. (2002).
7. Druker, B. J. et al. Effects of a selective inhibitor of the Abl tyrosine kinase on the growth of Bcr-Abl positive cells. *Nat. Med.* 2: 561-6. (1996).
8. Dolma, S., Lessnick, S. L., Hahn, W. C. & Stockwell, B. R. Identification of genotype-selective antitumor agents using synthetic lethal chemical screening in engineered human tumor cells. *Cancer Cell.* 3: 285-96 (2003).
9. Stockwell, B. R., Haggarty, S. J. & Schreiber, S. L. High-throughput screening of small molecules in miniaturized mammalian cell-based assays involving post-translational modifications. *Chem Biol.* 6: 71-83. (1999).
10. Bailey, S, N., Sabatini, D. M. & Stockwell, B. R. Microarrays of Small Molecules Embedded in Biodegradable Polymers for Use in Mammalian Cell-Based Screens. *Proc Natl Acad Sci USA.* 101: 16144-16149 (2004).
11. Torrance, C. J., Agrawal, V., Vogelstein, B. & Kinzler, K. W. Use of isogenic human cancer cells for high-throughput screening and drug discovery. *Nat Biotechnol.* 19: 940-5. (2001).
12. Colicelli, J. Human RAS superfamily proteins and related GTPases. *Sci STKE.* 2004: RE13 (2004).

13. Walker, K. & Olson, M. F. Targeting Ras and Rho GTPases as opportunities for cancer therapeutics. *Curr Opin Genet Dev.* 15: 62-8 (2005).
14. Schreiber, S. L. Chemical genetics resulting from a passion for synthetic organic chemistry. *Bioorg. Med. Chem.* 6: 1127-1152 (1998).
15. Schreiber, S. L. Target-oriented and diversity-oriented organic synthesis in drug discovery. *Science.* 287: 1964-9. (2000).
16. Schreiber, S. L. The small-molecule approach to biology: Chemical genetics and diversity-oriented organic synthesis make possible the systematic exploration of biology. *Chem. & Eng. News.* 81: 51-61 (2003).
17. Stockwell, B. R. Chemical genetics: ligand-based discovery of gene function. *Nat Rev Genet.* 1: 116-25. (2000).
18. Stockwell, B. R. Frontiers in chemical genetics. *Trends Biotechnol.* 18: 449-55. (2000).
19. Stockwell, B. R. Chemical genetic screening approaches to neurobiology. *Neuron.* 36: 559-62 (2002).
20. Stockwell, B. R. Exploring biology with small organic molecules. *Nature.* 432: 846-54 (2004).
21. Smukste, I. & Stockwell, B. R. Advances in chemical genetics. *Annu Rev Genomics Hum Genet.* 6: 261-86 (2005).
22. Brown, E. J., et al. & Schreiber, S. L. A mammalian protein targeted by Gi-arresting rapamycin-receptor complex. *Nature.* 369: 756-758 (1994).
23. Sabatini, D. M., Erdjument-Bromage, H., Lui, M., Tempst, P. & Snyder, S. H. RAFT1: a mammalian protein that binds to FKBP12 in a rapamycin-dependent fashion and is homologous to yeast TORs. *Cell.* 78: 35-43. (1994).
24. Khersonsky, S. M. et al. Facilitated forward chemical genetics using a tagged triazine library and zebrafish embryo screening. *J Am Chem Soc.* 125: 11804-5 (2003).
25. Williams, a et al. Identification of compounds that bind mitochondrial FIFO ATPase by screening a triazine library for correction of albinism. *Chem. Biol.* 11: 1251-9 (2004).
26. Wan, Y. et al. Synthesis and target identification of hymenialdisine analogs. *Chem. Biol.* 11: 247-59 (2004).
27. Oda, Y. et al. Quantitative chemical proteomics for identifying candidate drug targets. *Anal Chem.* 75: 2159-65 (2003).
28. Parsons, A. B. et al. Integration of chemical-genetic and genetic interaction data links bioactive compounds to cellular target pathways. *Nat Biotechnol.* 22: 62-69 (2003).
29. Hsiang, Y. H. & Liu, L. F. Identification of mammalian DNA topoisomerase I as an intracellular target of the anticancer drug camptothecin. *Cancer Res.* 48: 1722-6. (1988).
30. Eng, W. K., Faucette, L., Johnson, R. K. & Sternglanz, R. Evidence that DNA topoisomerase I is necessary for the cytotoxic effects of camptothecin. *Mol Pharmacol.* 34: 755-60. (1988).
31. Madden, K. R. & Champoux, J. J. Overexpression of human topoisomerase I in baby hamster kidney cells: hypersensitivity of clonal isolates to camptothecin. *Cancer Res.* 52: 525-32. (1992).
32. Andoh, T. et al. Characterization of a mammalian mutant with a camptothecin-resistant DNA topoisomerase I. *Proc Natl Acad Sci USA.* 84: 5565-9. (1987).
33. Bjornsti, M. A., Benedetti, P., Viglianti, G. A. & Wang, J. C. Expression of human DNA topoisomerase I in yeast cells lacking yeast DNA topoisomerase I: restoration of sensitivity of the cells to the antitumor drug camptothecin. *Cancer Res.* 49: 6318-23. (1989).
34. Champoux, J. J. Structure-based analysis of the effects of camptothecin on the activities of human topoisomerase I. *Ann NY Acad Sci.* 922: 56-64. (2000).
35. Liu, L. F. et al. Mechanism of action of camptothecin. *Ann NY Acad Sci.* 922: 1-10. (2000).
36. D'Arpa, P., Beardmore, C. & Liu, L. F. Involvement of nucleic acid synthesis in cell killing mechanisms of topoisomerase poisons. *Cancer Res.* 50: 6919-24. (1990).
37. Hsiang, Y. H., Lihou, M. G. & Liu, L. F. Arrest of replication forks by drug-stabilized topoisomerase I-DNA cleavable complexes as a mechanism of cell killing by camptothecin. *Cancer Res.* 49: 5077-82. (1989).
38. Tsao, Y. P., Russo, A., Nyamuswa, G., Silber, R. & Liu, L. F. Interaction between replication forks and topoisomerase I-DNA cleavable complexes: studies in a cell-free SV40 DNA replication system. *Cancer Res.* 53: 5908-14. (1993).
39. Traganos, F., Seiter, K., Feldman, E., Halicka, H. D. & Darzynkiewicz, Z. Induction of apoptosis by camptothecin and topotecan. *Ann NY Acad Sci.* 803: 101-10. (1996).
40. Prestwich, G. D., Dorman, G., Elliott, J. T., Marecak, D. M. & Chaudhary, A. Benzophenone photoprobes for phosphoinositides, peptides and drugs. *Photochem Photobiol.* 65: 222-34 (1997).
41. Olszewski, J. D. et al. Tethered benzophenone reagents for the synthesis of photoactivatable ligands. *Bioconjug Chem.* 6: 395-400 (1995).
42. Dorman, G. & Prestwich, G. D. Benzophenone photophores in biochemistry. *Biochemistry.* 33: 5661-73 (1994).
43. Chen, J., Zheng, X. F., Brown, E. J. & Schreiber, S. L. Identification of an 11-kDa FKBP12-rapamycin-binding domain within the 289-kDa FKBP12-rapamycin-associated protein and characterization of a critical serine residue. *Proc Natl Acad Sci USA.* 92: 4947-51 (1995).
44. Stan, R. et al. Interaction between FKBP12-rapamycin and TOR involves a conserved serine residue. *J. Biol. Chem.* 269: 32027-32030 (1994).
45. Harvey, J. J. An Unidentified Virus Which Causes The Rapid Production Of Tumours In Mice. *Nature.* 204: 1104-5 (1964).
46. Kirsten, W. H. & Mayer, L. A. Morphological responses to a murine erythroblastosis virus. *J. Natl. Cancer Inst.* 39: 311-335 (1967).
47. Barbacid, M. ras genes. *Annu Rev Biochem.* 56: 779-827 (1987).
48. Bos, J. L. ras oncogenes in human cancer: a review. *Cancer Res.* 49: 4682-9 (1989).
49. Guerra, C. et al. Tumor induction by an endogenous K-ras oncogene is highly dependent on cellular context. *Cancer Cell.* 4: 111-20 (2003).
50. Jackson, E. L. et al. Analysis of lung tumor initiation and progression using conditional expression of oncogenic K-ras. *Genes Dev.* 15: 3243-8 (2001).
51. Johnson, L. et al. Somatic activation of the K-ras oncogene causes early onset lung cancer in mice. *Nature.* 410: 1111-6 (2001).
52. Meuwissen, R., Linn, S. C., van der Valk, M., Mooi, W. J. & Bems, A. Mouse model for lung tumorigenesis through Cre/lox controlled sporadic activation of the K-Ras oncogene. *Oncogene.* 20: 6551-8 (2001).
53. Malumbres, M. & Barbacid, M. RAS oncogenes: the first 30 years. *Nat Rev Cancer.* 3: 459-65 (2003).
54. Coleman, M. L., Marshall, C. J. & Olson, M. F. RAS and RHO GTPases in GI-phase cell-cycle regulation. *Nat Rev Mol Cell Biol.* 5: 355-66 (2004).
55. Hahn, W. C. Immortalization and transformation of human cells. *Mol Cells.* 13: 351-61. (2002).

56. Hahn, W. C. et al. Creation of human tumour cells with defined genetic elements. *Nature.* 400: 464-8. (1999).
57. Hahn, W. C. et al. Enumeration of the simian virus 40 early region elements necessary for human cell transformation. *Mol Cell Biol.* 22: 2111-23. (2002).
58. Hahn, W. C. & Weinberg, R. A. Modelling the molecular circuitry of cancer. *Nat Rev Cancer.* 2: 331-41. (2002).
59. Hahn, W. C. & Weinberg, R. A. Rules for making human tumor cells. *N Engl J Med.* 347: 1593-603. (2002).
60. Lessnick, S. L., Dacwag, C. S. & Golub, T. R. The Ewing's sarcoma oncoprotein EWS/FLI induces a p53-dependent growth arrest in primary human fibroblasts. *Cancer Cell.* 1: 393-401. (2002).
61. Rostovtseva, T. K., Tan, W. & Colombini, M. On the Role of VDAC in Apoptosis: Fact and Fiction. *J Bioenerg Biomembr.* 37: 129-42 (2005).
62. Rahmani, Z., Maunoury, C. & Siddiqui, A. Isolation of a novel human voltage-dependent anion channel gene. *Eur J Hum Genet.* 6: 337-40 (1998).
63. Graham, B. H. & Craigen, W. J. Genetic approaches to analyzing mitochondrial outer membrane permeability. *Curr Top Dev Biol.* 59: 87-118 (2004).
64. Anflous, K., Armstrong, D. D. & Craigen, W. J. Altered mitochondrial sensitivity for ADP and maintenance of creatine-stimulated respiration in oxidative striated muscles from VDAC1-deficient mice. *J Biol Chem.* 276: 1954-60 (2001).
65. Sampson, M. J. et al. Immotile sperm and infertility in mice lacking mitochondrial voltage-dependent anion channel type 3. *J Biol Chem.* 276: 39206-12 (2001).
66. Forte, M., Guy, H. R. & Mannella, C. A. Molecular genetics of the VDAC ion channel: structural model and sequence analysis. *J Bioenerg Biomembr.* 19: 341-50 (1987).
67. Shao, L., Kinnally, K. W. & Mannella, C. A. Circular dichroism studies of the mitochondrial channel, VDAC, from *Neurospora crassa. Biophys J.* 71: 778-86 (1996).
68. Kmita, H., Budzinska, M. & Stobienia, O. Modulation of the voltage-dependent anion-selective channel by cytoplasmic proteins from wild type and the channel depleted cells of *Saccharomyces cerevisiae. Acta Biochim Pol.* 50: 415-24 (2003).
69. Mannella, C. A. Minireview: on the structure and gating mechanism of the mitochondrial channel, VDAC. *J Bioenerg Biomembr.* 29: 525-31 (1997).
70. Thomas, L., Blachly-Dyson, E., Colombini, M. & Forte, M. Mapping of residues forming the voltage sensor of the voltage-dependent anion-selective channel. *Proc Natl Acad Sci USA.* 90: 5446-9 (1993).
71. Stanley, S., Dias, J. A., D'Arcangelis, D. & Mannella, C. A. Peptide-specific antibodies as probes of the topography of the voltage-gated channel in the mitochondrial outer membrane of *Neurospora crassa. J Biol Chem.* 270: 16694-700 (1995).
72. Casadio, R., Jacoboni, I., Messina, A. & De Pinto, V. A 3D model of the voltage-dependent anion channel (VDAC). *FEBS Lett.* 520:1-7 (2002).
73. Chandra, D., Choy, G., Daniel, P. T. & Tang, D. G. Bax-dependent regulation of Bak by voltage-dependent anion channel 2. *J Biol Chem.* 280: 19051-61 (2005).
74. Baker, M. A., Lane, D. J., Ly, J. D., De Pinto, V. & Lawen, A. VDAC1 is a transplasma membrane NADH-ferricyanide reductase. *J Biol Chem.* 279: 4811-9 (2004).
75. Thinnes, F. P. Evidence for extra-mitochondrial localization of the VDAC/porin channel in eucaryotic cells. *J Bioenerg Biomembr.* 24: 71-5 (1992).
76. Dermietzel, R. et al. Cloning and in situ localization of a brain-derived porin that constitutes a large-conductance anion channel in astrocytic plasma membranes. *Proc Natl Acad Sci USA.* 91: 499-503 (1994).
77. Thinnes, F. P. et al. Studies on human porin XXI: gadolinium opens Up cell membrane standing porin channels making way for the osmolytes chloride or taurine-A putative approach to activate the alternate chloride channel in cystic fibrosis. *Mol Genet Metab.* 69: 240-51 (2000).
78. Buettner, R., Papoutsoglou, G., Scemes, E., Spray, D. C. & Dermietzel, R. Evidence for secretory pathway localization of a voltage-dependent anion channel isoform. *Proc Natl Acad Sci USA.* 97: 3201-6 (2000).
79. Gonzalez-Gronow, M., Kalfa, T., Johnson, C. E., Gawdi, G. & Pizzo, S. V. The voltage-dependent anion channel is a receptor for plasminogen kringle 5 on human endothelial cells. *J Biol Chem.* 278: 27312-8 (2003).
80. Bahamonde, M. I., Fernandez-Fernandez, J. M., Guix, F. X., Vazquez, E. & Valverde, M. A. Plasma membrane voltage-dependent anion channel mediates antiestrogen-activated maxi Cl-currents in C1300 neuroblastoma cells. *J Biol Chem.* 278: 33284-9 (2003).
81. Bahamonde, M. I. & Valverde, M. A. Voltage-dependent anion channel localises to the plasma membrane and peripheral but not perinuclear mitochondria. *Pflugers Arch.* 446: 309-13 (2003).
82. Fiek, C., Benz, R., Roos, N. & Brdiczka, D. Evidence for identity between the hexokinase-binding protein and the mitochondrial porin in the outer membrane of rat liver mitochondria. *Biochim Biophys Acta.* 688: 429-40 (1982).
83. Crompton, M. The mitochondrial permeability transition pore and its role in cell death. *Biochem J.* 341 (Pt 2): 233-49 (1999).
84. Brdiczka, D. Contact sites between mitochondrial envelope membranes. Structure and function in energy- and protein-transfer. *Biochim Biophys Acta.* 1071: 291-312 (1991).
85. Krimmer, T. et al. Biogenesis of porin of the outer mitochondrial membrane involves an import pathway via receptors and the general import pore of the TOM complex. *J Cell Biol.* 152: 289-300 (2001).
86. Linden, M. & Karlsson, G. Identification of porin as a binding site for MAP2. *Biochem Biophys Res Commun.* 218: 833-6 (1996).
87. Madesh, M. & Hajnoczky, G. VDAC-dependent permeabilization of the outer mitochondrial membrane by superoxide induces rapid and massive cytochrome c release. *J Cell Biol.* 155: 1003-15 (2001).
88. Tsujimoto, Y. & Shimizu, S. VDAC regulation by the Bcl-2 family of proteins. *Cell Death Differ.* 7: 1174-81 (2000).
89. Shimizu, S., Narita, M. & Tsujimoto, Y. Bcl-2 family proteins regulate the release of apoptogenic cytochrome c by the mitochondrial channel VDAC. *Nature.* 399: 483-7 (1999).
90. Averet, N., Aguilaniu, H., Bunoust, O., Gustafsson, L. & Rigoulet, M. NADH is specifically channeled through the mitochondrial porin channel in *Saccharomyces cerevisiae. J Bioenerg Biomembr.* 34: 499-506 (2002).
91. Vander Heiden, M. G. et al. Outer mitochondrial membrane permeability can regulate coupled respiration and cell survival. *Proc Natl Acad Sci USA.* 97: 4666-71 (2000).
92. Leist, M. & Jaattela, M. Four deaths and a funeral: from caspases to alternative mechanisms. *Nat Rev Mol Cell Biol.* 2: 589-98 (2001).
93. Majno, G. & Joris, I. Apoptosis, oncosis, and necrosis. An overview of cell death. *Am J Pathol.* 146: 3-15. (1995).

94. Kerr, J. F., Wyllie, A. H. & Currie, A. R. Apoptosis: a basic biological phenomenon with wide-ranging implications in tissue kinetics. *Br J Cancer.* 26: 239-57 (1972).
95. Baehrecke, E. H. Autophagic programmed cell death in *Drosophila. Cell Death Differ.* 10: 940-5 (2003).
96. Syntichaki, P. & Tavernarakis, N. The biochemistry of neuronal necrosis: rogue biology? *Nat Rev Neurosci.* 4: 672-84 (2003).
97. Jagtap, P. & Szabo, C. Poly(ADP-ribose) polymerase and the therapeutic effects of its inhibitors. *Nat Rev Drug Discov.* 4: 421-40 (2005).
98. Blankenberg, F. G. Recent advances in the imaging of programmed cell death. *Curr Pharm Des.* 10: 1457-67 (2004).
99. Danial, N. N. & Korsmeyer, S. J. Cell death: critical control points. *Cell.* 116: 205-19 (2004).
100. Sgonc, R. & Gruber, J. Apoptosis detection: an overview. *Exp Gerontol.* 33: 525-33 (1998).
101. Walker, N. I., Harmon, B. V., Gobe, G. C. & Kerr, J. F. Patterns of cell death. *Methods Achiev Exp Pathol.* 13: 18-54 (1988).
102. Boyce, M., Degterev, A. & Yuan, J. Caspases: an ancient cellular sword of Damocles. *Cell Death Differ.* 11: 29-37 (2004).
103. Zhivotovsky, B. Apoptosis, necrosis and between. *Cell Cycle.* 3: 64-6 (2004).
104. Ohsumi, Y. Molecular dissection of autophagy: two ubiquitin-like systems. *Nat Rev Mol Cell Biol.* 2: 211-6. (2001).
105. Abeliovich, H., Zhang, C., Dunn, W. A., Jr., Shokat, K. M. & Klionsky, D. J. Chemical genetic analysis of Apg1 reveals a non-kinase role in the induction of autophagy. *Mol Biol Cell.* 14: 477-90 (2003).
106. Broker, L. E., Kruyt, F. A. & Giaccone, G. Cell death independent of caspases: a review. *Clin Cancer Res.* 11: 3155-62 (2005).
107. Chen, Y. et al. Living T9 glioma cells expressing membrane macrophage colony-stimulating factor produce immediate tumor destruction by polymorphonuclear leukocytes and macrophages via a "paraptosis"-induced pathway that promotes systemic immunity against intracranial T9 gliomas. *Blood.* 100: 1373-80 (2002).
108. Fombonne, J., Padron, L., Enjalbert, A., Krantic, S. & Torriglia, A. A novel paraptosis pathway involving LEI/L-DNaseII for EGF-induced cell death in somato-lactotrope pituitary cells. *Apoptosis.* (2006).
109. Franklin, D. J. & Berges, J. A. Mortality in cultures of the dinoflagellate *Amphidinium carterae* during culture senescence and darkness. *Proc Biol Sci.* 271: 2099-107 (2004).
110. Jadus, M. R. et al. Human U251MG glioma cells expressing the membrane form of macrophage colony-stimulating factor (mM-CSF) are killed by human monocytes in vitro and are rejected within immunodeficient mice via paraptosis that is associated with increased expression of three different heat shock proteins. *Cancer Gene Ther.* 10: 411-20 (2003).
111. Schneider, D. et al. Intracellular acidification by inhibition of the Na+/H+-exchanger leads to caspase-independent death of cerebellar granule neurons resembling paraptosis. *Cell Death Differ.* 11: 760-70 (2004).
112. Sperandio, S. et al. Paraptosis: mediation by MAP kinases and inhibition by AIP-1/Alix. *Cell Death Differ.* 11: 1066-75 (2004).
113. Wang, Y. et al. An alternative form of paraptosis-like cell death, triggered by TAJ/TROY and enhanced by PDCD5 overexpression. *J Cell Sci.* 117: 1525-32 (2004).
114. Root, D. E., Flaherty, S. P., Kelley, B. P. & Stockwell, B. R. Biological mechanism profiling using an annotated compound library. *Chem Biol.* 10: 881-92 (2003).
115. Blanchard, B. J., Stockwell, B. R. & Ingram, V. M. Eliminating membrane depolarization caused by the Alzheimer peptide Abeta(1-42, aggr.). *Biochem Biophys Res Commun.* 293: 1204-8 (2002).
116. Lunn, M. R. et al. Indoprofen upregulates the survival motor neuron protein through a cyclooxygenase-independent mechanism. *Chemistry & Biology.* 11: 1489-1493 (2004).
117. Stegmaier, K. et al. Gene expression-based high-throughput screening(GE-HTS) and application to leukemia differentiation. *Nat. Genet.* 36: 257-63 (2004).
118. Pollitt, S. K. et al. A rapid cellular FRET assay of polyglutamine aggregation identifies a novel inhibitor. *Neuron.* 40: 685-94 (2003).
119. Blanchard, B. J. et al. Efficient reversal of Alzheimer's disease fibril formation and elimination of neurotoxicity by a small molecule. *Proc Natl Acad Sci USA.* 101: 14326-32 (2004).
120. Root, D. E., Kelley, B. P. & Stockwell, B. R. Detecting spatial patterns in biological array experiments. *J Biomol Screen.* 8: 393-8 (2003).
121. Root, D. E., Kelley, B. P. & Stockwell, B. R. Global analysis of large-scale chemical and biological experiments. *Curr Opin Drug Discov Devel.* 5: 355-60 (2002).
122. Kelley, B. P. et al. PathBLAST: a tool for alignment of protein interaction networks. *Nucleic Acids Res.* 32: W83-8 (2004).
123. Kelley, B. P. et al. Conserved pathways within bacteria and yeast as revealed by global protein network alignment. *Proc Natl Acad Sci USA.* 100: 11394-9 (2003).
124. Kelley, B. P. et al. A Flexible Data Analysis Tool for Chemical Genetic Screens. *Chemistry & Biology.* 11: 1495-1503 (2004).
125. Moffat, J. et al. A lentiviral RNAi library for human and mouse genes applied to an arrayed viral high-content screen. *Cell.* 124: 1283-98 (2006).
126. Lunn, M. R. et al. Indoprofen upregulates the survival motor neuron protein through a cyclooxygenase-independent mechanism. *Chem. Biol.* 11: 1489-93 (2004).
127. Kelley, B. P. et al. A flexible data analysis tool for chemical genetic screens. *Chem. Biol.* 11: 1495-503 (2004).
128. Smukste, I., Bhalala, O., Persico, M. & Stockwell, B. R. Using small molecules to overcome drug resistance induced by a viral oncogene. *Cancer Cell.* 9: 133-46 (2006).
129. Dorman, G. & Prestwich, G. D. Using photolabile ligands in drug discovery and development. *Trends Biotechnol.* 18: 64-77 (2000).
130. Weber, P. J. & Beck-Sickinger, A. G. Comparison of the photochemical behavior of four different photoactivatable probes. *J Pept Res.* 49: 375-83 (1997).
131. Pestic-Dragovich, L. et al. A myosin I isoform in the nucleus. *Science.* 290: 337-41 (2000).
132. Nociari, M. M., Shalev, A., Benias, P. & Russo, C. A novel one-step, highly sensitive fluorometric assay to evaluate cell-mediated cytotoxicity. *J. Immunol. Methods.* 13: 157-167 (1998).
133. Wang, X. M. et al. A new microcellular cytotoxicity test based on calcein AM release. *Hum. Immunol.* 37: 264-270 (1993).
134. Testa, J. R. & Giordano, A. SV40 and cell cycle perturbations in malignant mesothelioma. *Semin Cancer Biol.* 11: 31-8. (2001).

135. Bosch, F. X. et al. Prevalence of human papillomavirus in cervical cancer: a worldwide perspective. International biological study on cervical cancer (IBSCC) Study Group. *J Natl Cancer Inst.* 87: 796-802 (1995).
136. Elenbaas, B. et al. Human breast cancer cells generated by oncogenic transformation of primary mammary epithelial cells. *Genes Dev.* 15: 50-65. (2001).
137. Perez-Stable, C., Altman, N. H., Mehta, P. P., Deftos, L. J. & Roos, B. A. Prostate cancer progression, metastasis, and gene expression in transgenic mice. *Cancer Res.* 57: 900-6. (1997).
138. Rich, J. N. et al. A genetically tractable model of human glioma formation. *Cancer Res.* 61: 3556-60. (2001).
139. Chan, Y. M., Wu, W., Yip, H. K., So, K. F. & Oppenheim, R. W. Caspase inhibitors promote the survival of avulsed spinal motoneurons in neonatal rats. *Neuroreport.* 12: 541-545 (2001).
140. Makin, G. Targeting apoptosis in cancer chemotherapy. *Expert Opin Ther Targets.* 6: 73-84. (2002).
141. Ho, S. H., Das Gupta, U. & Rieske, J. S. Detection of antimycin-binding subunits of complex III by photoaffinity-labeling with an azido derivative of antimycin. *J Bioenerg Biomembr.* 17: 269-82 (1985).
142. G, V. O, N. J. & Bohrer, C. Inhibition of electron transfer from ferrocytochrome b to ubiquinone, cytochrome c1 and duroquinone by antimycin. *Biochim Biophys Acta.* 387: 409-24 (1975).
143. Huang, P., Feng, L., Oldham, E. A., Keating, M. J. & Plunkett, W. Superoxide dismutase as a target for the selective killing of cancer cells. *Nature.* 407: 390-5 (2000).
144. Wood, L. et al. Inhibition of superoxide dismutase by 2-methoxyoestradiol analogues and oestrogen derivatives: structure-activity relationships. *Anticancer Drug Des.* 16: 209-15 (2001).
145. Gilad, E., Cuzzocrea, S., Zingarelli, B., Salzman, A. L. & Szabo, C. Melatonin is a scavenger of peroxynitrite. *Life Sci.* 60: PL169-74 (1997).
146. Plattner, R. et al. Differential contribution of the ERK and JNK mitogen-activated protein kinase cascades to Ras transformation of HT1080 fibrosarcoma and DLD-1 colon carcinoma cells. *Oncogene.* 18: 1807-17 (1999).
147. Davies, H. et al. Mutations of the BRAF gene in human cancer. *Nature.* 417: 949-54 (2002).
148. Patton, S. E. et al. Activation of the ras-mitogen-activated protein kinase pathway and phosphorylation of ets-2 at position threonine 72 in human ovarian cancer cell lines. *Cancer Res.* 58: 2253-9 (1998).
149. Beck, W. T. & Danks, M. K. Mechanisms of resistance to drugs that inhibit DNA topoisomerases. *Semin Cancer Biol.* 2: 235-44 (1991).
150. Shimizu, S., Konishi, A., Kodama, T. & Tsujimoto, Y. BH4 domain of antiapoptotic Bcl-2 family members closes voltage-dependent anion channel and inhibits apoptotic mitochondrial changes and cell death. *Proc Natl Acad Sci U S A.* 97: 3100-5 (2000).
151. Rahmani, Z., Huh, K. W., Lasher, R. & Siddiqui, A. Hepatitis B virus X protein colocalizes to mitochondria with a human voltage-dependent anion channel, HVDAC3, and alters its transmembrane potential. *J Virol.* 74: 2840-6 (2000).
152. Koppel, D. A. et al. Bacterial expression and characterization of the mitochondrial outer membrane channel. Effects of n-terminal modifications. *J Biol Chem.* 273: 13794-800 (1998).
153. Xu, X., Decker, W., Sampson, M. J., Craigen, W. J. & Colombini, M. Mouse VDAC isoforms expressed in yeast: channel properties and their roles in mitochondrial outer membrane permeability. *J Membr Biol.* 170: 89-102 (1999).
154. Navratilova, I., Sodroski, J. & Myszka, D. G. Solubilization, stabilization, and purification of chemokine receptors using biosensor technology. *Anal Biochem.* 339: 271-81 (2005).
155. Stenlund, P., Babcock, G. J., Sodroski, J. & Myszka, D. G. Capture and reconstitution of G protein-coupled receptors on a biosensor surface. *Anal Biochem.* 316: 243-50 (2003).
156. Cliff, M. J., Gutierrez, A. & Ladbury, J. E. A survey of the year 2003 literature on applications of isothermal titration calorimetry. *J Mol Recognit.* 17: 513-23 (2004).
157. Leavitt, S. & Freire, E. Direct measurement of protein binding energetics by isothermal titration calorimetry. *Curr Opin Struct Biol.* 11: 560-6 (2001).
158. Rostovtseva, T. & Colombini, M. VDAC channels mediate and gate the flow of ATP: implications for the regulation of mitochondrial function. *Biophys J.* 72: 1954-62 (1997).
159. Montal, M. & Mueller, P. Formation of bimolecular membranes from lipid monolayers and a study of their electrical properties. *Proc Natl Acad Sci USA.* 69: 3561-6 (1972).
160. Stewart, S. A. et al. Lentivirus-delivered stable gene silencing by RNAi in primary cells. *Rna.* 9: 493-501 (2003).
161. Lee, A. C., Zizi, M. & Colombini, M. Beta-NADH decreases the permeability of the mitochondrial outer membrane to ADP by a factor of 6. *J Biol Chem.* 269: 30974-80 (1994).
162. Zizi, M., Forte, M., Blachly-Dyson, E. & Colombini, M. NADH regulates the gating of VDAC, the mitochondrial outer membrane channel. *J Biol Chem.* 269: 1614-6 (1994).
163. Mannella, C. A. Conformational changes in the mitochondrial channel protein, VDAC, and their functional implications. *J Struct Biol.* 121: 207-18 (1998).
164. Giepmans, B. N., Adams, S. R., Ellisman, M. H. & Tsien, R. Y. The fluorescent toolbox for assessing protein location and function. *Science.* 312: 217-24 (2006).
165. Mannella, C. A. Structural analysis of mitochondrial pores. *Experientia.* 46: 137-45 (1990).
166. Peng, S., Blachly-Dyson, E., Forte, M. & Colombini, M. Large scale rearrangement of protein domains is associated with voltage gating of the VDAC channel. *Biophys J.* 62: 123-31; discussion 131-5 (1992).
167. Peng, S., Blachly-Dyson, E., Colombini, M. & Forte, M. Determination of the number of polypeptide subunits in a functional VDAC channel from *Saccharomyces cerevisiae*. *J Bioenerg Biomembr.* 24: 27-31 (1992).
168. Johnson, G. L. & Lapadat, R. Mitogen-activated protein kinase pathways mediated by ERK, JNK, and p38 protein kinases. *Science.* 298: 1911-2 (2002).
169. Inoue, K. et al. Isolation and characterization of mitochondrial DNA-less lines from various mammalian cell lines by application of an anticancer drug, ditercalinium. *Biochem Biophys Res Commun.* 239: 257-60 (1997).
170. Inoue, K. et al. Isolation of mitochondrial DNA-less mouse cell lines and their application for trapping mouse synaptosomal mitochondrial DNA with deletion mutations. *J Biol Chem.* 272: 15510-5 (1997).
171. Chrzanowska-Lightowlers, Z. M., Turnbull, D. M. & Lightowlers, R. N. A microtiter plate assay for cytochrome c oxidase in permeabilized whole cells. *Anal Biochem.* 214: 45-9 (1993).

172. Schriner, S. E. et al. Extension of murine life span by overexpression of catalase targeted to mitochondria. *Science*. 308: 1909-11 (2005).
173. Levi, S. & Arosio, P. Mitochondrial ferritin. *Int J Biochem Cell Biol*. 36: 1887-9 (2004).
174. He, H. et al. Identification of potent water soluble purine-scaffold inhibitors of the heat shock protein 90. *J Med Chem*. 49: 381-90 (2006).
175. Fury, M. G. et al. A phase I clinical pharmacologic study of pralatrexate in combination with probenecid in adults with advanced solid tumors. *Cancer Chemother Pharmacol*. 57: 671-7 (2006).
176. Frost, J. A. et al. Simian virus 40 small t antigen cooperates with mitogen-activated kinases to stimulate AP-1 activity. Mol Cell Biol 14, 6244-52 (1994).
177. Cheng, E. H., Sheiko, T. V., Fisher, J. K., Craigen, W. J. & Korsmeyer, S. J. VDAC2 inhibits BAK activation and mitochondrial apoptosis. Science 301, 513-7 (2003).
178. Poyurovsky, M. V. et al. Nucleotide binding by the Mdm2 RING domain facilitates Arf-independent Mdm2 nucleolar localization. Mol Cell 12, 875-87 (2003).
179. Koppel, D. A. et al. Bacterial expression and characterization of the mitochondrial outer membrane channel. Effects of n-terminal modifications. J Biol Chem 273, 13794-800 (1998).
180. Zhen, Y. et al. Development of an LC-MALDI method for the analysis of protein complexes. J Am Soc Mass Spectrom 15, 803-22 (2004).
181. Sage, J., Miller, A. L., Perez-Mancera, P. A., Wysocki, J. M. & Jacks, T. Acute mutation of retinoblastoma gene function is sufficient for cell cycle re-entry. Nature 424, 223-8 (2003).

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for identifying an agent, which induces RAS-RAF-MEK-dependent oxidative non-apoptotic cell death of a tumor cell, the method comprising:
   (a) detecting increasing VDAC level in the tumor cell, wherein the VDAC is selected from the group consisting of VDAC1, VDAC2, VDAC3, and combinations thereof,
   (b) contacting the tumor cell with the agent, and
   (c) determining whether the tumor cell dies via oxidative non-apoptotic cell death, comprising:
      (I) detecting an increased level of oxidative species in the tumor cell; and
      (II) identifying one or more of: (i) a lack of caspase 3 cleavage or activation; (ii) a lack of cytochrome C release; (iii) a lack of PARP cleavage or activation; (iv) a lack of Annexin V staining; (v) lack of alterations in chromatin morphology; (vi) a lack of nuclear DNA laddering; (vii) a lack of TUNEL staining of nuclear DNA; and (viii) a lack of depletion of ATP levels,
   wherein if the tumor cell dies via oxidative nonapoptotic cell death, then the agent induces RAS-RAF-MEK-dependent oxidative non-apoptotic cell death.

2. The method according to claim 1, further comprising (d) determining whether mitochondrial morphology of the tumor cell is altered, wherein altered mitochondrial morphology of the tumor cell is further indicative that the agent induced the oxidative non-apoptotic cell death.

3. The method according to claim 1, wherein the oxidative non-apoptotic cell death is iron-dependent.

4. The method according to claim 1, wherein step (c)(II) comprises identifying all of: (i) a lack of caspase 3 cleavage or activation; (ii) a lack of cytochrome C release; (iii) a lack of PARP cleavage or activation; (iv) a lack of Annexin V staining; (v) lack of alterations in chromatin morphology; (vi) a lack of nuclear DNA laddering; (vii) a lack of TUNEL staining of nuclear DNA; and (viii) a lack of depletion of ATP levels.

5. A method for identifying a first agent, which induces RAS-RAF-MEK-dependent oxidative non-apoptotic cell death of a tumor cell, the method comprising:
   (a) detecting increasing VDAC level in the tumor cell, wherein the VDAC is selected from the group consisting of VDAC1, VDAC2, VDAC3, and combinations thereof,
   (b) contacting the tumor cell with the first agent in the presence and absence of a second agent selected from the group consisting of an iron chelator, an anti-oxidant, and an inhibitor of mitochondria-generated oxidative species, and
   (c) determining whether the tumor cell dies via oxidative non-apoptotic cell death in the absence of the second agent, comprising:
      (I) detecting an increased level of oxidative species in the tumor cell; and
      (II) identifying one or more of: (i) a lack of caspase 3 cleavage or activation; (ii) a lack of cytochrome C release; (iii) a lack of PARP cleavage or activation; (iv) a lack of Annexin V staining; (v) lack of alterations in chromatin morphology; (vi) a lack of nuclear DNA laddering; (vii) a lack of TUNEL staining of nuclear DNA; and (viii) a lack of depletion of ATP levels,
   wherein if the tumor cell dies via oxidative nonapoptotic cell death in the absence of the second agent, but is viable in the presence of the second agent, then the first agent induces RAS-RAF-MEK-dependent oxidative non-apoptotic cell death.

6. The method according to claim 5, wherein step (c)(II) comprises identifying all of: (i) a lack of caspase 3 cleavage or activation; (ii) a lack of cytochrome C release; (iii) a lack of PARP cleavage or activation; (iv) a lack of Annexin V staining; (v) lack of alterations in chromatin morphology; (vi) a lack of nuclear DNA laddering; (vii) a lack of TUNEL staining of nuclear DNA; and (viii) a lack of depletion of ATP levels.

7. The method according to claim 2, wherein the tumor cell expresses a fluorescently labeled VDAC protein, and the method further comprises:
   (d) measuring the fluorescent signal due to the fluorescently labeled VDAC protein,
   wherein if the tumor cell dies via oxidative nonapoptotic cell death, and if the fluorescence due to the fluorescently labeled VDAC protein decreases, then the agent induces RAS-RAF-MEK-dependent non-apoptotic oxidative cell death.

8. The method according to claim 2, wherein the tumor cell expresses a fluorescence resonance energy transfer (FRET) system comprising a VDAC protein with two different fluorescent labels, wherein the labeled VDAC protein exhibits fluorescent emission at a first and second wavelength when VDAC is open, or a first, second and third (FRET) wavelength when VDAC is closed;, and the method further comprises:
- (d) measuring a fluorescent signal due to the fluorescently labeled VDAC protein, wherein if the tumor cell dies via oxidative nonapoptotic cell death, and if the fluorescence due to FRET in the labeled VDAC protein decreases, then the agent induces RAS-RAF-MEK-dependent non-apoptotic oxidative cell death.

9. The method according to claim 2, further comprising:
- (d) providing a non-tumor cell that is syngeneic to the tumor cell, and
- (e) measuring a level of VDAC in the non-tumor cell, wherein if the level of VDAC in the tumor cell is increased compared to the VDAC level in the syngeneic non-tumor cell and if the tumor cell dies via oxidative non-apoptotic cell death, then the tumor cell is susceptible to the agent which induces RAS-RAF-MEK-dependent non-apoptotic oxidative cell death.

10. The method according to claim 9, wherein VDAC protein level is measured in step (e).

11. The method according to claim 9, wherein VDAC mRNA level is measured in step (e).

12. The method according to claim 9, wherein the tumor cell and the syngeneic cell are derived from a subject having a tumor.

* * * * *

```
                              SEQUENCE LISTING

<160> NUMBER OF SEQ ID NOS: 39

<210> SEQ ID NO 1
<211> LENGTH: 57
<212> TYPE: DNA
<213> ORGANISM: Artificial
<220> FEATURE:
<223> OTHER INFORMATION: synthetic construct; shRNA V1.161

<400> SEQUENCE: 1
ccgggctatg gatttggctt aataactcga gttattaagc caaatccata gcttttt         57

<210> SEQ ID NO 2
<211> LENGTH: 57
<212> TYPE: DNA
<213> ORGANISM: Artificial
<220> FEATURE:
<223> OTHER INFORMATION: synthetic construct; shRNA V1.279

<400> SEQUENCE: 2
ccggcaagta cagatggact gagtactcga gtactcagtc catctgtact tgttttt         57

<210> SEQ ID NO 3
<211> LENGTH: 57
<212> TYPE: DNA
<213> ORGANISM: Artificial
<220> FEATURE:
<223> OTHER INFORMATION: synthetic construct; shRNA V1.396

<400> SEQUENCE: 3
ccggcgattc atccttctca cctaactcga gttaggtgag aaggatgaat cgttttt         57

<210> SEQ ID NO 4
<211> LENGTH: 57
<212> TYPE: DNA
<213> ORGANISM: Artificial
<220> FEATURE:
<223> OTHER INFORMATION: synthetic construct; shRNA V1.607

<400> SEQUENCE: 4
ccgggcagtt ggctacaaga ctgatctcga gatcagtctt gtagccaact gcttttt         57

<210> SEQ ID NO 5
<211> LENGTH: 57
```

-continued

```
<212> TYPE: DNA
<213> ORGANISM: Artificial
<220> FEATURE:
<223> OTHER INFORMATION: synthetic construct; shRNA V1.921

<400> SEQUENCE: 5
ccgggcttgg tctaggactg gaattctcga gaattccagt cctagaccaa gcttttt        57

<210> SEQ ID NO 6
<211> LENGTH: 58
<212> TYPE: DNA
<213> ORGANISM: Artificial
<220> FEATURE:
<223> OTHER INFORMATION: synthetic construct; shRNA V2.A8(A7)

<400> SEQUENCE: 6
ccgggcagct aaatatcagt tggatctcga gatccaactg atatttagct gcttttg        58

<210> SEQ ID NO 7
<211> LENGTH: 58
<212> TYPE: DNA
<213> ORGANISM: Artificial
<220> FEATURE:
<223> OTHER INFORMATION: synthetic construct; shRNA V2.A9

<400> SEQUENCE: 7
ccggcaaggt ttgaaactga catttctcga gaaatgtcag tttcaaacct tgttttg        58

<210> SEQ ID NO 8
<211> LENGTH: 58
<212> TYPE: DNA
<213> ORGANISM: Artificial
<220> FEATURE:
<223> OTHER INFORMATION: synthetic construct; shRNA V2.A10

<400> SEQUENCE: 8
ccggcactgc ttccatttct gcaaactcga gtttgcagaa atggaagcag tgttttg        58

<210> SEQ ID NO 9
<211> LENGTH: 58
<212> TYPE: DNA
<213> ORGANISM: Artificial
<220> FEATURE:
<223> OTHER INFORMATION: synthetic construct; shRNA V2.A11

<400> SEQUENCE: 9
ccgggtgtga gtatggtctg actttctcga gaaagtcaga ccatactcac acttttg        58

<210> SEQ ID NO 10
<211> LENGTH: 58
<212> TYPE: DNA
<213> ORGANISM: Artificial
<220> FEATURE:
<223> OTHER INFORMATION: synthetic construct; shRNA V2.A12

<400> SEQUENCE: 10
ccgggtcaac aactctagct taattctcga gaattaagct agagttgttg acttttg        58

<210> SEQ ID NO 11
<211> LENGTH: 58
<212> TYPE: DNA
<213> ORGANISM: Artificial
<220> FEATURE:
<223> OTHER INFORMATION: synthetic construct; shRNA V3.B1

<400> SEQUENCE: 11
ccgggcaacc tagaaaccaa atatactcga gtatatttgg tttctaggtt gcttttg        58
```

```
<210> SEQ ID NO 12
<211> LENGTH: 58
<212> TYPE: DNA
<213> ORGANISM: Artificial
<220> FEATURE:
<223> OTHER INFORMATION: synthetic construct; shRNA V3.B2

<400> SEQUENCE: 12
ccggccagga gtcaaattga ctttactcga gtaaagtcaa tttgactcct ggttttttg      58

<210> SEQ ID NO 13
<211> LENGTH: 58
<212> TYPE: DNA
<213> ORGANISM: Artificial
<220> FEATURE:
<223> OTHER INFORMATION: synthetic construct; shRNA V3.B3

<400> SEQUENCE: 13
ccggccaaac tgtcacagaa taattctcga gaattattct gtgacagttt ggttttttg      58

<210> SEQ ID NO 14
<211> LENGTH: 58
<212> TYPE: DNA
<213> ORGANISM: Artificial
<220> FEATURE:
<223> OTHER INFORMATION: synthetic construct; shRNA V3.B4

<400> SEQUENCE: 14
ccggccagaa ttggaacaca gacaactcga gttgtctgtg ttccatttct ggttttttg      58

<210> SEQ ID NO 15
<211> LENGTH: 58
<212> TYPE: DNA
<213> ORGANISM: Artificial
<220> FEATURE:
<223> OTHER INFORMATION: synthetic construct; shRNA V3.B5

<400> SEQUENCE: 15
ccggcaggag tcaaattgac tttatctcga gataaagtca atttgactcc tgttttttg      58

<210> SEQ ID NO 16
<211> LENGTH: 58
<212> TYPE: DNA
<213> ORGANISM: Artificial
<220> FEATURE:
<223> OTHER INFORMATION: synthetic construct; shRNA V3.B6

<400> SEQUENCE: 16
ccggccagaa ggtgaatgag aagatctcga gatcttctca ttcaccttct ggttttttg      58

<210> SEQ ID NO 17
<211> LENGTH: 58
<212> TYPE: DNA
<213> ORGANISM: Artificial
<220> FEATURE:
<223> OTHER INFORMATION: synthetic construct; shRNA Nras.304

<400> SEQUENCE: 17
ccggcgcact gacaatccag ctaatctcga gattagctgg attgtcagtg cgttttttg      58

<210> SEQ ID NO 18
<211> LENGTH: 58
<212> TYPE: DNA
<213> ORGANISM: Artificial
<220> FEATURE:
<223> OTHER INFORMATION: synthetic construct; shRNA Nras.398
```

<400> SEQUENCE: 18
ccgggaaacc tgtttgttgg acatactcga gtatgtccaa caaacaggtt tcttttg     58

<210> SEQ ID NO 19
<211> LENGTH: 58
<212> TYPE: DNA
<213> ORGANISM: Artificial
<220> FEATURE:
<223> OTHER INFORMATION: synthetic construct; shRNA Nras.445

<400> SEQUENCE: 19
ccggcagtgc catgagagac caatactcga gtattggtct ctcatggcac tgttttg     58

<210> SEQ ID NO 20
<211> LENGTH: 58
<212> TYPE: DNA
<213> ORGANISM: Artificial
<220> FEATURE:
<223> OTHER INFORMATION: synthetic construct; shRNA Nras.501

<400> SEQUENCE: 20
ccggccatca ataatagcaa gtcatctcga gatgacttgc tattattgat ggttttg     58

<210> SEQ ID NO 21
<211> LENGTH: 58
<212> TYPE: DNA
<213> ORGANISM: Artificial
<220> FEATURE:
<223> OTHER INFORMATION: synthetic construct; shRNA Nras.655

<400> SEQUENCE: 21
ccggcaagag ttacgggatt ccattctcga gaatggaatc cgtaactct tgttttg      58

<210> SEQ ID NO 22
<211> LENGTH: 58
<212> TYPE: DNA
<213> ORGANISM: Artificial
<220> FEATURE:
<223> OTHER INFORMATION: synthetic construct; shRNA Kras.269

<400> SEQUENCE: 22
ccgggacgaa tatgatccaa caatactcga gtattgttgg atcatattcg tcttttg     58

<210> SEQ ID NO 23
<211> LENGTH: 58
<212> TYPE: DNA
<213> ORGANISM: Artificial
<220> FEATURE:
<223> OTHER INFORMATION: synthetic construct; shRNA Kras.407

<400> SEQUENCE: 23
ccgggagggc tttctttgtg tatttctcga gaaatacaca agaaagccc tcttttg      58

<210> SEQ ID NO 24
<211> LENGTH: 58
<212> TYPE: DNA
<213> ORGANISM: Artificial
<220> FEATURE:
<223> OTHER INFORMATION: synthetic construct; shRNA Kras.509

<400> SEQUENCE: 24
ccggcctatg gtcctagtag gaaatctcga gatttcctac taggaccata ggttttg     58

<210> SEQ ID NO 25
<211> LENGTH: 58

```
<212> TYPE: DNA
<213> ORGANISM: Artificial
<220> FEATURE:
<223> OTHER INFORMATION: synthetic construct; shRNA Kras.667

<400> SEQUENCE: 25
ccgggatccg acaatacaga ttgaactcga gttcaatctg tattgtcgga tcttttg        58

<210> SEQ ID NO 26
<211> LENGTH: 58
<212> TYPE: DNA
<213> ORGANISM: Artificial
<220> FEATURE:
<223> OTHER INFORMATION: synthetic construct; shRNA Kras.1160

<400> SEQUENCE: 26
ccggtagttg gagctggtgg cgtagctcga gctacgccac cagctccaac tattttg        58

<210> SEQ ID NO 27
<211> LENGTH: 57
<212> TYPE: DNA
<213> ORGANISM: Artificial
<220> FEATURE:
<223> OTHER INFORMATION: synthetic construct; shRNA iBRAF-1

<400> SEQUENCE: 27
ccgggagttc aggagagtag caattcaaga gattgctact ctcctgaact cttttg         57

<210> SEQ ID NO 28
<211> LENGTH: 64
<212> TYPE: DNA
<213> ORGANISM: Artificial
<220> FEATURE:
<223> OTHER INFORMATION: synthetic construct; shRNA BRAF

<400> SEQUENCE: 28
gatccccgtg ttggagaatg ttccacttca agagagtgga acattctcca cactttttg     60 gaaa                                                                  64

<210> SEQ ID NO 29
<211> LENGTH: 64
<212> TYPE: DNA
<213> ORGANISM: Artificial
<220> FEATURE:
<223> OTHER INFORMATION: synthetic construct; shRNA Luciferase

<400> SEQUENCE: 29 gatcccccctt acgctgagta cttcgattca agagatcgaa gtactcagcg taagttttg    60 gaaa                                                                  64

<210> SEQ ID NO 30
<211> LENGTH: 23
<212> TYPE: DNA
<213> ORGANISM: Artificial
<220> FEATURE:
<223> OTHER INFORMATION: VDAC1 forward primer

<400> SEQUENCE: 30
cctggacagc aggaaacagt aac                                             23

<210> SEQ ID NO 31
<211> LENGTH: 20
<212> TYPE: DNA
<213> ORGANISM: Artificial
<220> FEATURE:
<223> OTHER INFORMATION: VDAC2 forward primer
```

<400> SEQUENCE: 31
tgattttgct ggacctgcaa                                          20

<210> SEQ ID NO 32
<211> LENGTH: 20
<212> TYPE: DNA
<213> ORGANISM: Artificial
<220> FEATURE:
<223> OTHER INFORMATION: VDAC3 forward primer

<400> SEQUENCE: 32
aatttcgccc tgggttacaa                                          20

<210> SEQ ID NO 33
<211> LENGTH: 20
<212> TYPE: DNA
<213> ORGANISM: Artificial
<220> FEATURE:
<223> OTHER INFORMATION: RPLPO.1 forward primer

<400> SEQUENCE: 33
acgggtacaa acgagtcctg                                          20

<210> SEQ ID NO 34
<211> LENGTH: 20
<212> TYPE: DNA
<213> ORGANISM: Artificial
<220> FEATURE:
<223> OTHER INFORMATION: RPLPO.2 forward primer

<400> SEQUENCE: 34
acgggtacaa acgagtcctg                                          20

<210> SEQ ID NO 35
<211> LENGTH: 20
<212> TYPE: DNA
<213> ORGANISM: Artificial
<220> FEATURE:
<223> OTHER INFORMATION: VDAC1 reverse primer

<400> SEQUENCE: 35
aggcgtcagg gtcaatctga                                          20

<210> SEQ ID NO 36
<211> LENGTH: 18
<212> TYPE: DNA
<213> ORGANISM: Artificial
<220> FEATURE:
<223> OTHER INFORMATION: VDAC2 reverse primer

<400> SEQUENCE: 36
cagcaagcca gccctcat                                            18

<210> SEQ ID NO 37
<211> LENGTH: 21
<212> TYPE: DNA
<213> ORGANISM: Artificial
<220> FEATURE:
<223> OTHER INFORMATION: VDAC3 reverse primer

<400> SEQUENCE: 37
tcagtgccat cgttcacatg t                                        21

<210> SEQ ID NO 38
<211> LENGTH: 20

-continued

```
<212> TYPE: DNA
<213> ORGANISM: Artificial
<220> FEATURE:
<223> OTHER INFORMATION: RPLP0.1 reverse primer

<400> SEQUENCE: 38
gccttgacct tttcagcaag                                              20

<210> SEQ ID NO 39
<211> LENGTH: 19
<212> TYPE: DNA
<213> ORGANISM: Artificial
<220> FEATURE:
<223> OTHER INFORMATION: RPLP0.2 reverse primer

<400> SEQUENCE: 39
atctgctgca tctgcttgg                                               19
```